(12) United States Patent
Fox et al.

(10) Patent No.: US 7,507,580 B2
(45) Date of Patent: Mar. 24, 2009

(54) ZTNFR14, A TUMOR NECROSIS FACTOR RECEPTOR

(75) Inventors: Brian A. Fox, Seattle, WA (US); James L. Holloway, Seattle, WA (US); Paul O. Sheppard, Granite Falls, WA (US); Stacey R. Dillon, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 285 days.

(21) Appl. No.: 10/967,527

(22) Filed: Oct. 18, 2004

(65) Prior Publication Data

US 2005/0256041 A1    Nov. 17, 2005

Related U.S. Application Data

(60) Provisional application No. 60/511,698, filed on Oct. 16, 2003.

(51) Int. Cl.
C07K 14/705    (2006.01)
C12N 5/10    (2006.01)
C12N 15/11    (2006.01)

(52) U.S. Cl. ............ 435/325; 536/23.1; 536/23.5; 435/69.1; 435/320.1; 435/252.3; 435/254.11; 530/350

(58) Field of Classification Search ................ None
See application file for complete search history.

(56) References Cited

U.S. PATENT DOCUMENTS

2007/0015271 A1*    1/2007    Rosen et al.

FOREIGN PATENT DOCUMENTS

WO    WO 0198353 A2 * 12/2001
WO    WO 0202634 A2 * 1/2002
WO    WO 0244340 A2 * 6/2002

OTHER PUBLICATIONS

GenBank Database, Accession # AL390719, version 47, Human DNA sequence from clone RP11-465B22 on chromosome 1, (6 pages) May 23, 2003, accessed May 8, 2007.*
GenBank Database, Accession # BC008788, version 1, "*Homo sapiens* hypothetical protein FLJ20584", Jun. 18, 2003, accessed May 8, 2007.*
Strausberg et al., Generation and initial analysis of more than 15,000 full-length human and mouse cDNA sequences, Proc. Nat'l Acad. Sci., 99(26):16899-16903, published online Dec. 11, 2002.*
Mammalian Gene Collection Database, Image Id:3627081, accession BCV08788, "C1orf159", accessed May 8, 2007.*
Clark et al., Inferring nonneutroal evoution from human-chimp-mouse orthologous gene trios, Science 302(5652):1960-1963, Dec. 12, 2003.*
Database EMBL, Sep. 16, 2003, XP002317141 retrieved from EBI, Database accession No. AK000591, abstract.
Database UniProt, Oct. 1, 2000, XP002317142 retrieved from EBI, Database accession No. Q9NWVO, abstract.
Database UniProt, Dec. 1, 2001, XP002317185 retrieved from EBI, Database accession No. Q96HA4, abstract.
Database EMBL, Jun. 7, 2002, XP002317186 retrieved from EBI, Database accession No. AX402506, abstract.

* cited by examiner

*Primary Examiner*—Lorraine Spector
*Assistant Examiner*—Claire Kaufman
(74) *Attorney, Agent, or Firm*—Michelle L. Lewis

(57) ABSTRACT

Novel tumor necrosis factor receptor (TNFR) polypeptides, polynucleotides encoding the polypeptides, antibodies and related compositions and methods are disclosed. The polypeptides may be used for detecting ligand, as well as agonists and antagonists. The polypeptides, polynucleotides and antibodies may also be used in methods that modulate tumor growth, metastasis, and immunity such as separating resting from stimulated immune cells.

13 Claims, 9 Drawing Sheets

```
HUZTNFR12    MRRGPRSLRGRDA-----------------------------------PAPT
MUZTNFR12    MGARRLRVRSQRS-----------------------------RDSSVPT
HU_BCMA      MLQMA--------------------------------------------G
MU_BCMA      MAQ-----------------------------------------------
HU_ZTNFR14   MALRHLALLAGLLVGVAS-KSMENTAQLPECCVDVVGVNASCPGASLCGP
MU_ZTNFR14   MALQCLLLLTGLLTGGVC-KSTESQAQQPECCMDVVDFNATCLGTGLCGP
MU_TWEAKR    MAPGWPRSLPQILVLGFGLVLMRAAA---------------GEQAPGTS
HU_tweakr    MARGSLRRLLRLLVLGLWLALLRSVA---------------GEQAPGTA
MU_EDAR      MAHVGDCKWMSWLPVLVVSLMCSA--------------------KAEDS
HU_EDAR      MAHVGDCQTPWLPVLVVSLMCSA---------------------RAEYS
HU_XEDAR     M-------------------------------------------------
HU_TACI      MSGLGRSRRGGRSRVDQEERF-----------------PQGLWTGVAMR
MU_TACI      MAMA----------------------------------------------
HU_MK61      MGPGRCLLTALLLLALAPP--------------------------PEASQ
MU_MK61      MGPSWLLWTVAVAVLLLTR-----------------------AASMEASS HUZTNFR12    PCVPAECFDLLVRHCVACGLLR----------------------------
MUZTNFR12    QCNQTECFDPLVRNCVSCELFH----------------------------
HU_BCMA      QCSQNEYFDSLLHACIPCQLRC----SSNTPPLTC-------QRYCNASV
MU_BCMA      QCFHSEYFDSLLHACKPCHLRC------SNPPATC-------QPYCDPSV
HU_ZTNFR14   GCYRRWNAD-GSASCVRCGNG------TLPAYN-------GSECRSFA-
MU_ZTNFR14   GCYRHWNAD-GSASCVRCWNG------TLPTYN-------DSECRILT-
MU_TWEAKR    PCSSGSSWSADLDKCMDCA-SC----PARPHSDFC--------LGC----
HU_tweakr    PCSRGSSWSADLDKCMDCA-SC----RARPHSDFC--------LGC----
MU_EDAR      NCGENEYHNQTTGLCQQCP-PCRPG---EEPYMSCGYGTKDDDYGCVP--
HU_EDAR      NCGENEYYNQTTGLCQECP-PCGPG---EEPYLSCGYGTKDEDYGCVP--
HU_XEDAR     DCQENEYWD-QWGRCVTCQ-RCGPG---QELSKDCGYGEGGDAY-CTA--
HU_TACI      SCPEEQYWDPLLGTCMSCKTIC-----NHQSQRTC-------AAFCRSL-
MU_TACI      FCPKDQYWDSSRKSCVSCALTC-----SQRSQRTC-------TDFCKFI-
HU_MK61      YCGRLEYWNPDNKCCSSCLQRF----------------------------
MU_MK61      FCGHLEYWNSDKRCCSRCLQRF----------------------------

HUZTNFR12    --------------------------------------------------
MUZTNFR12    --------------------------------------------------
HU_BCMA      TNSVKGT-------------------------------------------
MU_BCMA      TSSVKGT-------------------------------------------
HU_ZTNFR14   --------------------------------------------------
MU_ZTNFR14   --------------------------------------------------
MU_TWEAKR    --------------------------------------------------
HU_tweakr    --------------------------------------------------
MU_EDAR      -----------CPAEKFSKGGYQICRRHKDCEGFFRATVLTPGDMENDA
HU_EDAR      -----------CPAEKFSKGGYQICRRHKDCEGFFRATVLTPGDMENDA
HU_XEDAR     -----------CPPRRYKSSWGHHRCQSCITCAVINRVQKVNCTATSNA
HU_TACI      ----------------SCRKEQGKFYDHLLRDCISCASICGQ
MU_TACI      ----------------NCRKEQGRYYDHLLGACVSCDSTCTQ
HU_MK61      --------GPPPCPDYEFRENCGLNDHGDFVTPPFRKCSS-GQCNP----
MU_MK61      --------GPPACPDHEFTENCGLNDFGDTVAHPFKKCSP-GYCNP----
```

Figure 1A

```
HUZTNFR12    ------------------------------------------------
MUZTNFR12    ------------------------------------------------
HU_BCMA      ------------------------------------------------
MU_BCMA      ------------------------------------------------
HU_ZTNFR14   ------------------------------------------------
MU_ZTNFR14   ------------------------------------------------
MU_TWEAKR    ------------------------------------------------
HU_tweakr    ------------------------------------------------
MU_EDAR      ECGPCLPGYYMLENRPRNIYGMVCYSCL-LAPPNTKECVGATSGVSAHSS
HU_EDAR      ECGPCLPGYYMLENRPRNIYGMVCYSCL-LAPPNTKECVGATSGASANFP
HU_XEDAR     VCGDCLPRFY-RKTRIGGLQDQECIPCTKQTPTSEVQCAFQLSL------
HU_TACI      HPKQCAYFCENKLRSPVNLPPELRRQRSGEVENNSDNSGRYQGLEH----
MU_TACI      HPQQCAHFCEKRPRSQANLQPELGRPQAGEVEVRSDNSGRHQGSEH----
HU_MK61      --------DGAELCSPCGGGAVTP-TPAAGGGRTPWRCRE-RPVPAKGHC
MU_MK61      --------NGTELCSQCSSGAAAAPAHVESPGRTHKQCRK--PVPPKDVC HUZTNFR12    TPRPKP-AGASSPAPRTALQPQESVGAGAGEAALPLPGLLFGAPALLGLA
MUZTNFR12    TPDTG---HTSSLEPGTALQPQEGS------ALRPDVALLVGAPALLGLI
HU_BCMA      ----------------------------------NAILWTCLGLS
MU_BCMA      ----------------------------------YTVLWIFLGLT
HU_ZTNFR14   ------------GPGAPFPMNRSSGTPGRPHPGAPRVAASLFLGTFFIS
MU_ZTNFR14   ------------GRGMQLPMNRSTGTPGQPHFGGPHVAASLFLGTLFIS
MU_TWEAKR    --------------------------AAAPPAHFRLLWPILGGALS
HU_tweakr    --------------------------AAAPPAPFRLLWPILGGALS
MU_EDAR      -------------STSGGSTLSPFQHAHKELSGQGHLATALIIAMSTIFI
HU_EDAR      -------------GTSGSSTLSPFQHAHKELSGQGHLATALIIAMSTIFI
HU_XEDAR     -------------------------VEADAPTVPPQEATLVALVSSLLV
HU_TACI      -------------------RGSEASPALPGLKLSADQVALVYSTLGLCLC
MU_TACI      --------------------------GPGLRLSSDQ-LTLYCTLGVCLC
HU_MK61      PLTPGNPGAPSSQERSSPASSIAWRTPEPVPQQAWPNFLPLVVLVLLLTL
MU_MK61      PLKP-EDAGASSSPGRWSLGQTTKNEVSSQPGFVSASVLPLAVLPLLLVL HUZTNFR12    LVLALVLVG-LVSWRRRQRR----------------------
MUZTNFR12    LALTLVGLVSLVSWRWRQ-Q-----------------------
HU_BCMA      LIISLAVFVLMFLLRKISSEPLKDEFKNTGS------------------
MU_BCMA      LVLSLALFTISFLLRKMNPEALKDEPQSPGQ------------------
HU_ZTNFR14   SGLILSVAGFFYLKRSSKLPRACYRRNKA--------------------
MU_ZTNFR14   TGLILSVAGFFYLKRSSKLPEVFYRRDRA--------------------
MU_TWEAKR    LVLVLALVSSFLVWRRCRRR-----------------------------
HU_tweakr    LTFVLGLLSGFLVWRRCRRR-----------------------------
MU_EDAR      MAIAIVLIIMFYIMKTKPSAPACCS----------SPPGKSAEAPANTHE
HU_EDAR      MAIAIVLIIMFYILKTKPSAPACCT----------SHPGKSVEAQVSKDE
HU_XEDAR     VFTLAFLGLFFLYCKQFFN---------------RHCQRGGLLQFEADK
HU_TACI      AVLCCFLVAVACFLKKR-------------------------------GD
MU_TACI      AIFCCFLVALASFLRRR-----------------------------GEPL
HU_MK61      AVIAILLFILLWHLCWPKEKADPYPYPGLVCG-------------VPN
MU_MK61      LLILAVVLLSLFKRKVRSRPSSSSAFGDPSTS-------------LHY
```

Figure 1B

```
HUZTNFR12    ----LRGASSAEAPDGDKDAPEPLDKVIILSPGISDATAPAWPPPGEDPG
MUZTNFR12    ----LRTAS---PDTSEGVQQESLENVFVPSSETPHASAPTWPPLKEDAD
HU_BCMA      ----GL----LGMANIDLEKSRTGDEIILPRGLEYTVEECTCEDCIKSKP
MU_BCMA      ----LDGSAQLDKADTELTRIRAGDDRIFPRSLEYTVEECTCEDCVKSKP
HU_ZTNFR14   --------------------------------------------------
MU_ZTNFR14   --------------------------------------------------
MU_TWEAKR    --------------------------------------------------
HU_tweakr    --------------------------------------------------
MU_EDAR      EKKEAPDSVVTFPE--------NGEFQKLTATPTKTPKSENDASSENEQL
HU_EDAR      EKKEAPDNVVMFSE--------KDEFEKLTATPAKPTKSENDASSENEQL
HU_XEDAR     TAKEESLFPVPPSKETSAESQ--------------VSENIFQTQPLNPIL
HU_TACI      PCSCQP-RSRPRQSPAKSSQDHAMEAGSPVSTSPEPVETCSFCFPECR--
MU_TACI      PSQPAGPRGSQANSPHARPVTEACDEVTASPQPVETCSFCFPERS----
HU_MK61      THTPSSSHLSSPGALETGDTWKEASLLPLLSRELSSLASQPLSRLLDELE
MU_MK61      WPCPGTL------EVLESRNRGKANLLQLSSWELQGLASQPLSLLLDELE HUZTNFR12    TTPPGHSVPVPATELGSTELV--------------TTKTAGPEQQ----
MUZTNFR12    SALPRHSVPVPATELGSTELV--------------TTKTAGPEQ-----
HU_BCMA      KVDSDHCFPLPAMEEGATILV--------------TTKTNDYCKS----
MU_BCMA      KGDSDHFFPLPAMEEGATILV--------------TTKTGDYGKS----
HU_ZTNFR14   ------PALQPGEAAAMIPPP--------------QSSVRKPRYVRRERPL
MU_ZTNFR14   ------PVLQPGETAAMVPLP--------------QSSVRKPRYIRREQHP
MU_TWEAKR    -----EKFTTPIEETGGEGCPGVALIQ1----------------------
HU_tweakr    -----EKFTTPIEETGGEGCPAVALIQ-----------------------
MU_EDAR      LSRSVDSDEEPAPDKQGSPELCLLSLVHLAREKSVTSNKSAGIQSRRKKI
HU_EDAR      LSRSVDSDEEPAPDKQGSPELCLLSLVHLAREKSATSNKSAGIQSRRKKI
HU_XEDAR     EDDCSSTSGFPTQESFTMASCTSESHSHWVHSPIECTELDQKFSSSASY
HU_TACI      ---------APTQESAVTPGT--------------PDPTCAGRWGCHTRT
MU_TACI      ---------SPTQESAPRSLG--------------------IHGFAGT
HU_MK61      VLEELIVLLDPEPGPGGGMAH--GTTRHLAARYGLPAAWSTFAYSLRPSR
MU_MK61      VLEELIMLLDPEPGPSGSTAY--GTTRHLAARYGLPATWSTFAYSLRPSR HUZTNFR12    --------------------------------------------------
MUZTNFR12    --------------------------------------------------
HU_BCMA      ---LPAALSATEIEKSISAR1-----------------------------
MU_BCMA      -SVPTALQSVMGMEKPTHTR1-----------------------------
HU_ZTNFR14   DRATDPAAF-PGEARISNV1------------------------------
MU_ZTNFR14   DKNRDPSAFSTVEAHISNV1------------------------------
MU_TWEAKR    --------------------------------------------------
HU_tweakr    --------------------------------------------------
MU_EDAR      LDVYANVCGVVEGLSPTELPFDCLEKTSRMLSSTYNSEKAVVKTWRHLAE
HU_EDAR      LDVYANVCGVVEGLSPTELPFDCLEKTSRMLSSTYNSEKAVVKTWRHLAE
HU_XEDAR     TGAETLGGNTVESTGDRLELNPFEVPSP----------------------
HU_TACI      TVLQPCPHIPDSGLGIVCVPAQEGGPGA1---------------------
MU_TACI      AAPQPCMRA--TVGGLGVLRASTGDARPAT1-------------------
HU_MK61      SPLRALIEMVVAREPSASLGQLGTHLAQLGRADALRVLSKLGSSGVCWA-
MU_MK61      SPLRALIEMVVAREPSATLGQFGTYLAQLGRTDALQVLSKLG--------
```

Figure 1C

| | |
|---|---|
| HUZTNFR12 | ------------------------------------------------- |
| MUZTNFR12 | ------------------------------------------------- |
| HU_BCMA | ------------------------------------------------- |
| MU_BCMA | ------------------------------------------------- |
| HU_ZTNFR14 | ------------------------------------------------- |
| MU_ZTNFR14 | ------------------------------------------------- |
| MU_TWEAKR | ------------------------------------------------- |
| HU_tweakr | ------------------------------------------------- |
| MU_EDAR | SFGLKRDEIGGMTDGMQLFDRISTAGYSIPELLTKLVQIERLDAVESLCA |
| HU_EDAR | SFGLKRDEIGGMTDGMQLFDRISTAGYSIPELLTKLVQIERLDAVESLCA |
| HU_XEDAR | ------------------------------------------------- |
| HU_TACI | ------------------------------------------------- |
| MU_TACI | ------------------------------------------------- |
| HU_MK61 | ------------------------------------------------- |
| MU_MK61 | ------------------------------------------------- |
| | |
| HUZTNFR12 | ------------------ |
| MUZTNFR12 | ------------------ |
| HU_BCMA | ------------------ |
| MU_BCMA | ------------------ |
| HU_ZTNFR14 | ------------------ |
| MU_ZTNFR14 | ------------------ |
| MU_TWEAKR | ------------------ |
| HU_tweakr | ------------------ |
| MU_EDAR | DILEWAGVVPPASPPPAAS |
| HU_EDAR | DILEWAGVVPPASQPHAAS |
| HU_XEDAR | ------------------ |
| HU_TACI | ------------------ |
| MU_TACI | ------------------ |
| HU_MK61 | ------------------ |
| MU_MK61 | ------------------ |

Figure 1D

```
                    10        20        30        40        50
HUZTNFR12   -------PAPTPCVPAECFDLLVRHCVACGLLR-----------------------
HU_BCMA     ----------GQCSQNEYFDSLLHACIPCQLRC-SSNTPPLTC-------QRYCNASV
HU_ZTNFR14  ASCPGASLCGPGCYRRWNAD-GSASCVRCGNG----TLPAYN--------GSECRSFA
MU_ZTNFR14  ATCLGTGLCGPGCYRHWNAD-GSASCVRCWNG----TLPTYN--------DSECRILT
HU_tweakr   ---GEQAPGTAPCSRGSSWSADLDKCMDCA-SC-RARPHSDFC--------LGC----
HU_EDAR     ------RAEYSNCGENEYYNQTTGLCQECP-PCGPGEEPYLSCGYGTKDEDYGCVP--
HU_XEDAR    ----------DCQENEYWD-QWGRCVTCQ-RCGPGQELSKDCGYGEGGDAY-CTA--
HU_TACI     PQGLWTGVAMRSCPEEQYWDPLLGTCMSCKTIC--NHQSQRTC-------AAFCRSL-
HU_MK61     ------PEASQYCGRLEYWNPDNKCCSSCLQRF-------------------------
Cons        --c-----c---C-------------C--C---c---------c----------C----
```

Figure 2

```
              10        20        30        40        50        60
human    MALRHLALLAGLLVGVASKSMENTAQLPECCVDVVGVNASCPGASLCGPGCYRRWNADGSA
mouse    MALQCLLLLTGLLTGGVCKSTESQAQQPECCMDVVDFNATCLGTGLCGPGCYRHWNADGSA
rat      MALQCLMLLTGLVVGGMSKSTESKAQQPECCMDVVDVNATCLGTGLCGPGCYRHWNADGSA
cow      MALRRAVFLAGLLVEVASRASGTAGQQPECCVDAGNINATCPGTSLCGPGCYGRPAEDGSV
chicken  MEVPYVLLLTRLVAEVASKSTESSVSETECCVDMLESNSSCPVANQCSPGCYRRWNEDGS-
xenopus  MAVPCAIFLGRFIADTVSILSVVN----DCCSER-DLNGSCPISHRCSPGCFRLWSEDGSS
Cons     M-------L-------------------CC------N--C-----C-PGC------DGS- Num              70        80        90       100       110       120
human    SCVRCGNGT--LPAYNGSECRSFAGPGAPFPMNRSSGTPGRPHPGAPRVAASLFLGTFFIS
mouse    SCVRCWNGT--LPTYNDSECRILTGRGMQLPMNRSTGTPGQPHFGGPHVAASLFLGTLFIS
rat      SCVRCWNGT--LPTYNGSECRILTGRGMQFPMNRSTGTPGQPHFGGPHVAASLFLGTLFIS
cow      SCVQCRNG-----THNSSECRGLAGRGAQFPVNKSAGMPGWQSVGGPQVAASLFLGTFLIS
chicken  SCIKCKNET--L-PYNLTDCRNTGIRGMNFQMNISTVTPFIQNIGGPEVAASLILGTFFIS
xenopus  TCIKCKNETGSEVIHNVTECRNFSSSTLDVNLNASITPSVSHNLGSPGIAASLLLGILFIS
Cons     -C--C-N--------N---CR-----------N-S---------G-P--AASL-LG---IS Num             130       140       150       160       170       180
human    SGLILSVAGFFYLKRSSKLPRACYRRNKAPALQPGEAAAMIPPPQSSVRKPRYVRRERPLD
mouse    TGLILSVAGFFYLKRSSKLPEVFYRRDRAPVLQPGETAAMVPLPQSSVRKPRYIRREQHPD
rat      TGLILSVAGFFYLKRSSKLPEVFYRRDRAPVLQPGETAAMVPLPQSSVRKPRYIRREQHPE
cow      SGLILSVAAFFYLKRASKLPKVFYGRNRAPALQPGEAAVMIPPPQSSVRKPRYVRRERPLD
chicken  LFLILSVASFFYLKRANKLPNVFYRRNKAPALQPGEAAAMIPPPQSSVRKPRYVRRERPLD
xenopus  LFLILSVASFFYLKRSQKLPEIFYRRNKASIFQPSEMASMIPNPNSSVRKPRYVRRERTRT
Cons     --LILSVA-FFYLKR--KLP---Y-R--A---QP-E-A-M-P-P-SSVRKPRY-RRE----

Num             190
human    RATDPAAFPG-EARISNV--
mouse    KNRDPSAFSTVEAHISNV--
rat      KNRDPSAFSTVEAHISNV--
cow      RDVGPTTVSSVEARVSNV--
chicken  RATDPAAFPG-EARISNV--
xenopus  TAVPESSVDT---RVSNV--
Cons     ---------------SNV--
```

Figure 3

SEQUENCE LISTING

<160> NUMBER OF SEQ ID NOS: 51

<210> SEQ ID NO 1
<211> LENGTH: 1853
<212> TYPE: DNA
<213> ORGANISM: homo sapiens

<400> SEQUENCE: 1

```
gtgtacgaaa gagaaacccg gagggcgccg gggactgggc cggggtctgc agggctcagc        60
tgagcccatg agctcccaga gctaacccct gaacacccag gcgggcaaag ggctgatgtc       120
ggtagtcccc atcctggagg ggcaggctct gcgcatctgc tcctggcatg gcgctgcggc       180
acctcgccct cctggctggc cttctcgtgg gagtcgccag caagtccatg gagaacacgg       240
cccagctgcc cgagtgctgt gtggatgtgg tgggcgtcaa cgccagctgc ccaggcgcaa       300
gtctgtgtgg tccaggctgt tacaggcgct ggaacgcgga cgggagcgcc agctgcgtcc       360
gctgtgggaa cggaaccctc ccagcctaca acggctccga gtgtagaagc tttgctggcc       420
cgggtgcgcc attccccatg aacagaagct cagggacccc cgggcggcca catcctgggg       480
ctccgcgcgt ggccgcctcc ctcttcctgg gcacgttctt cattagctcc ggcctcatcc       540
tctccgtagc tgggttcttc tacctcaagc gctccagtaa actccccagg gcctgctaca       600
gaagaaacaa agctccggcc ctgcagcctg gcgaagccgc tgcaatgatc cccccgccac       660
agtcctcagt acggaagccg cgctacgtca ggcgggagcg gccctggac agggccacgg       720 atcccgctgc cttcccgggg gaggcccgta tcagcaatgt ctgacctgga ggccgagacc       780
acgccacgca cttggcggca gggaccccga ggccgacccc ttggcgggaa ccagcacaaa       840
```

-continued

```
gtgttggcat cgcccggcgc ccgggacagt cctgggcaca gcctcggctc tgggtccctc    900
cgcctcccag cgacggacgc caaagggtcc cgggccgcct gaggctcctc cccaccacag    960
ccatctcgtt tatcggacca ggagcaggca tccatgagac ctcagagctt cagatcgagg   1020
ccttgggggg tccgggcccc cccaggaaac acggtgaggc cccagcgcct gcagccaaag   1080
ctggcacgat ctatgggca ggtgccgctc tgcctagaaa agccaggggc tctgctgccg    1140
tgccctccag agcccacagc gggcaggact cctccagcac caccacaccc agtggcccga   1200
gacccctctg agaacagtga ggctggtcct cgtgccgttc cagccggtgc ccggccagtg   1260
gggaggacac agcctaggaa ccagctgcct gagaccaggg tgcctctggg ctgtcctccc   1320
gcgtggcgga accccaagc acgcagccac ccatttccgg agctgcagga tagagcttcc    1380
tcttgatctc tgttttaag cagaaattca ttgtgctgaa aagtcctcca gagctctgtg    1440
gccccgctcg gatccgctgg accccatgc ctggctgatc cctgcccacg tggggcaggc    1500
ccacatctaa cccccacaag tcactgcctc actgcacctg ccaaggctgc cctggcgctg   1560
agtcctgggg tccctcccgg agttcctggg agaaaggcgc cgtcgtggcc gcctcccgca   1620
cgccaggccc gggctccacc gtgggtctca gacgccctgc ggcaccggca ccgtctgctt   1680
tagcatggga cccccatctg aggggtggcc tggccttcgg ggtccccacg ctcctttgcg   1740
aagtccactg tgggtgccat catggtctcc gggacctggg ccagcgggaa cgtgggggca   1800
ctgggtgtgc tgatataaag tcggcattac tcaaaaaaaa aaaaaaaaa aaa          1853
```

<210> SEQ ID NO 2
<211> LENGTH: 198
<212> TYPE: PRT
<213> ORGANISM: homo sapiens

<400> SEQUENCE: 2

```
Met Ala Leu Arg His Leu Ala Leu Leu Ala Gly Leu Leu Val Gly Val
 1               5                  10                  15

Ala Ser Lys Ser Met Glu Asn Thr Ala Gln Leu Pro Glu Cys Cys Val
            20                  25                  30

Asp Val Gly Val Asn Ala Ser Cys Pro Gly Ala Ser Leu Cys Gly
        35                  40                  45

Pro Gly Cys Tyr Arg Arg Trp Asn Ala Asp Gly Ser Ala Ser Cys Val
     50                  55                  60

Arg Cys Gly Asn Gly Thr Leu Pro Ala Tyr Asn Gly Ser Glu Cys Arg
 65                  70                  75                  80

Ser Phe Ala Gly Pro Gly Ala Pro Phe Pro Met Asn Arg Ser Ser Gly
                85                  90                  95

Thr Pro Gly Arg Pro His Pro Gly Ala Pro Arg Val Ala Ala Ser Leu
            100                 105                 110

Phe Leu Gly Thr Phe Phe Ile Ser Ser Gly Leu Ile Leu Ser Val Ala
        115                 120                 125

Gly Phe Phe Tyr Leu Lys Arg Ser Ser Lys Leu Pro Arg Ala Cys Tyr
    130                 135                 140

Arg Arg Asn Lys Ala Pro Ala Leu Gln Pro Gly Glu Ala Ala Ala Met
145                 150                 155                 160

Ile Pro Pro Pro Gln Ser Ser Val Arg Lys Pro Arg Tyr Val Arg Arg
                165                 170                 175

Glu Arg Pro Leu Asp Arg Ala Thr Asp Pro Ala Ala Phe Pro Gly Glu
            180                 185                 190

Ala Arg Ile Ser Asn Val
```

```
                195

<210> SEQ ID NO 3
<211> LENGTH: 2541
<212> TYPE: DNA
<213> ORGANISM: mus musculus

<400> SEQUENCE: 3
cccacgcgtc cggcggccgg tacgaaagga gctcggctgg cgagtgaatt cctctatcta      60
ggaagctcag actactattg ttccagaatt ggaaatgccc agcttgcctg ctccttcaat     120
gcttcggggg ccgctgctaa gtaaaaagtc ttcatagaga tctccttgtc agctccccag     180
catggcactg cagtgtctcc tgctcctgac tggccttctg acaggaggcg tgtgcaagtc     240
cacagaaagc caggcccagc aacctgagtg ttgcatggat gtggtagact caatgctac      300 ctgcctcggt acaggtctct gtggcccagg ttgctacagg cactggaatg cagatgggag     360
cgctagctgt gtccggtgct ggaatgggac cctcccgaca tacaatgact ctgagtgtag     420
aattctcact ggccggggca tgcagcttcc catgaacagg agcacgggga cacctggaca     480
gccacatttt gggggtcctc atgtggcagc ttctctcttc ctggggacac tcttcatcag     540
cacaggcctc atcctctctg tggctggatt cttctacctc aagcgctcca gcaaacttcc     600
tgaggttttc tacaggagag acagagcccc tgtcctgcag cctggtgaga cagctgccat     660 ggtcccctg ccacagtctt cagtgaggaa gccaagatac atccggcgtg agcagcaccc      720
agacaagaat agggaccctt ctgccttctc tacagtggag gcccacatca gcaacgtctg     780
atctagaggt caactgagac ttcacagtac agcagtggag acccaaggcc cctccagtg      840 agctcactac acaaagggcc tgggccttaa gatatgccag aatggactcc caatggcaga     900
catgcacgaa tgctagggg atgctaacgt ccatgccatg agatcgtcac tgtgtggttt      960
aacaggagca accatctgtg agactgagga ctcaagagca agtcatgtgg ggtctgtgcc    1020
ccttaagagt aacagcatct atagcagcta taacacagac ctgatccaaa cggtcaaaac    1080
ttctggagcc cacccactgg agcccatagt agacaggact ccattcccac cgagctaaga    1140
agatgaaacc aaggttccaa cagtggagaa aacacagcct ggatactggt tccagagata    1200
ggttgctcta gtgtcagcct gctagtttag ctgctgacct ctcaaggccc atgtttctca    1260
gagttgcaga attgagtatc cttggttttc tgattccaga agccagcaga gccttgtctt    1320
ccagggacag actccaccag ctaccttcag gctgggcact cagagcaaaa tgtttacccg    1380
tggggcctcc atctctgaac actcaggtca cttgtcccct tgggcttgtg agctcatgct    1440
ggttagcagt cctgtctttg ctctcccaag actccagaag cctgtgagct gctagtgtgg    1500
ctggtggtgt tggccatgtg ttcctataga aggaggtggc ctgatgacca gtgccatcct    1560
ccgtctagca tcttctttga cgtcaagcac acatctgatg ttatgcacag tgttaggagt    1620
ttgctttccc agagttgagc cagtgactca ggtagcagca gcaattccaa gctggaccaa    1680
ttcaattaga ctagatcttc tctcctcaag ctttgttgtc ccaaggtctc gtattcagtg    1740
tggtgtgtgg gagcgaacta ccccattgcc atgtccaggg gacaagtagg gaggggaaga    1800
agaagccctc agccggactc agagcctact gttgtctggt ggaactggca gtgcagcaca    1860
acccatcccc tcatctttcc ctggccatgt agccctcccc atttcaggac accatcttgc    1920
atgaagaggt gaccccgctc cttaggactt gaggtagaaa gtgccagtca agcacggcat    1980
ggttttcaga taagactaca tgcatcacta ggctttgagg gggccactgg cagtttatgg    2040
atctaattga cccttgggga aagcagaacc ctcgacctgg ccaccggagt tcattttagt    2100
```

```
ggtcccctc aaagcccatg tgtagacgta cagatgtgtg tctgctgact agaggcagaa    2160
ccggataaag agagccaaat gagagcttag ggattctaga agtcctgcca ggtagtttga    2220
taagaatgcc tacccagtgc ccccaggctt acatacttga attgctgagt catcagggat    2280
tacgggagag gcttaggagg tgtggctttta ttggaggaag tgtgtctctg gggatgggca    2340
ttgggtctca aaagctcaag ccaggcccag tggctttcat ttcctgctgc ctgtggattt    2400
ggatgtagag ctctcagctc ctcgtccagc accatgtccg cctatgctac catgcttcct    2460
gccgttccga taatggacta aacctctgaa acagtagaca agccccaatt aaatactttg    2520
ttttataaaa aaaaaaaaa a                                               2541
```

<210> SEQ ID NO 4
<211> LENGTH: 199
<212> TYPE: PRT
<213> ORGANISM: mus musculus

<400> SEQUENCE: 4

```
Met Ala Leu Gln Cys Leu Leu Leu Thr Gly Leu Leu Thr Gly Gly
1               5                   10                  15

Val Cys Lys Ser Thr Glu Ser Gln Ala Gln Gln Pro Glu Cys Cys Met
                20                  25                  30

Asp Val Val Asp Phe Asn Ala Thr Cys Leu Gly Thr Gly Leu Cys Gly
                35                  40                  45

Pro Gly Cys Tyr Arg His Trp Asn Ala Asp Gly Ser Ala Ser Cys Val
        50                  55                  60

Arg Cys Trp Asn Gly Thr Leu Pro Thr Tyr Asn Asp Ser Glu Cys Arg
65                  70                  75                  80

Ile Leu Thr Gly Arg Gly Met Gln Leu Pro Met Asn Arg Ser Thr Gly
                85                  90                  95

Thr Pro Gly Gln Pro His Phe Gly Gly Pro His Val Ala Ala Ser Leu
            100                 105                 110

Phe Leu Gly Thr Leu Phe Ile Ser Thr Gly Leu Ile Leu Ser Val Ala
        115                 120                 125

Gly Phe Phe Tyr Leu Lys Arg Ser Ser Lys Leu Pro Glu Val Phe Tyr
    130                 135                 140

Arg Arg Asp Arg Ala Pro Val Leu Gln Pro Gly Glu Thr Ala Ala Met
145                 150                 155                 160

Val Pro Leu Pro Gln Ser Ser Val Arg Lys Pro Arg Tyr Ile Arg Arg
                165                 170                 175

Glu Gln His Pro Asp Lys Asn Arg Asp Pro Ser Ala Phe Ser Thr Val
            180                 185                 190

Glu Ala His Ile Ser Asn Val
        195
```

<210> SEQ ID NO 5
<211> LENGTH: 184
<212> TYPE: PRT
<213> ORGANISM: homo sapiens

<400> SEQUENCE: 5

```
Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
                20                  25                  30

Val Ala Cys Gly Leu Leu Arg Thr Pro Arg Pro Lys Pro Ala Gly Ala
```

-continued

```
                    35                  40                  45
Ser Ser Pro Ala Pro Arg Thr Ala Leu Gln Pro Gln Glu Ser Val Gly
 50                  55                  60

Ala Gly Ala Gly Glu Ala Ala Leu Pro Leu Pro Gly Leu Leu Phe Gly
 65                  70                  75                  80

Ala Pro Ala Leu Leu Gly Leu Ala Leu Val Leu Ala Leu Val Leu Val
                 85                  90                  95

Gly Leu Val Ser Trp Arg Arg Gln Arg Arg Leu Arg Gly Ala Ser
                100                 105                 110

Ser Ala Glu Ala Pro Asp Gly Asp Lys Asp Ala Pro Glu Pro Leu Asp
                115                 120                 125

Lys Val Ile Ile Leu Ser Pro Gly Ile Ser Asp Ala Thr Ala Pro Ala
130                 135                 140

Trp Pro Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175

Lys Thr Ala Gly Pro Glu Gln Gln
                180

<210> SEQ ID NO 6
<211> LENGTH: 26
<212> TYPE: PRT
<213> ORGANISM: homo sapiens
<220> FEATURE:
<221> NAME/KEY: DOMAIN
<222> LOCATION: (1)...(26)
<223> OTHER INFORMATION: cysteine rich

<400> SEQUENCE: 6

Pro Ala Pro Thr Pro Cys Val Pro Ala Glu Cys Phe Asp Leu Leu Val
 1               5                  10                  15

Arg His Cys Val Ala Cys Gly Leu Leu Arg
                20                  25

<210> SEQ ID NO 7
<211> LENGTH: 175
<212> TYPE: PRT
<213> ORGANISM: mus musculus

<400> SEQUENCE: 7

Met Gly Ala Arg Arg Leu Arg Val Arg Ser Gln Arg Ser Arg Asp Ser
 1               5                  10                  15

Ser Val Pro Thr Gln Cys Asn Gln Thr Glu Cys Phe Asp Pro Leu Val
                20                  25                  30

Arg Asn Cys Val Ser Cys Glu Leu Phe His Thr Pro Asp Thr Gly His
                35                  40                  45

Thr Ser Ser Leu Glu Pro Gly Thr Ala Leu Gln Pro Gln Glu Gly Ser
 50                  55                  60

Ala Leu Arg Pro Asp Val Ala Leu Leu Val Gly Ala Pro Ala Leu Leu
 65                  70                  75                  80

Gly Leu Ile Leu Ala Leu Thr Leu Val Gly Leu Val Ser Leu Val Ser
                 85                  90                  95

Trp Arg Trp Arg Gln Gln Leu Arg Thr Ala Ser Pro Asp Thr Ser Glu
                100                 105                 110

Gly Val Gln Gln Glu Ser Leu Glu Asn Val Phe Val Pro Ser Ser Glu
                115                 120                 125
```

```
Thr Pro His Ala Ser Ala Pro Thr Trp Pro Pro Leu Lys Glu Asp Ala
    130                 135                 140

Asp Ser Ala Leu Pro Arg His Ser Val Pro Val Pro Ala Thr Glu Leu
145                 150                 155                 160

Gly Ser Thr Glu Leu Val Thr Thr Lys Thr Ala Gly Pro Glu Gln
                165                 170                 175

<210> SEQ ID NO 8
<211> LENGTH: 184
<212> TYPE: PRT
<213> ORGANISM: homo sapiens

<400> SEQUENCE: 8

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
        50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 9
<211> LENGTH: 40
<212> TYPE: PRT
<213> ORGANISM: homo sapiens
<220> FEATURE:
<221> NAME/KEY: DOMAIN
<222> LOCATION: (1)...(40)
<223> OTHER INFORMATION: cysteine rich

<400> SEQUENCE: 9

Gly Gln Cys Ser Gln Asn Glu Tyr Phe Asp Ser Leu Leu His Ala Cys
1               5                   10                  15

Ile Pro Cys Gln Leu Arg Cys Ser Ser Asn Thr Pro Pro Leu Thr Cys
                20                  25                  30

Gln Arg Tyr Cys Asn Ala Ser Val
            35                  40

<210> SEQ ID NO 10
<211> LENGTH: 185
<212> TYPE: PRT
<213> ORGANISM: mus musculus
```

-continued

```
<400> SEQUENCE: 10

Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Pro Ala Thr Cys
            20                  25                  30

Gln Pro Tyr Cys Asp Pro Ser Val Thr Ser Ser Val Lys Gly Thr Asn
        35                  40                  45

Ala Ile Leu Trp Thr Cys Leu Gly Leu Ser Leu Val Leu Ser Leu Ala
    50                  55                  60

Leu Phe Thr Ile Ser Phe Leu Leu Arg Lys Met Asn Pro Glu Ala Leu
65              70                  75                  80

Lys Asp Glu Pro Gln Ser Pro Gly Gln Leu Asp Gly Ser Ala Gln Leu
            85                  90                  95

Asp Lys Ala Asp Thr Glu Leu Thr Arg Ile Arg Ala Gly Asp Asp Arg
        100                 105                 110

Ile Phe Pro Arg Ser Leu Glu Tyr Thr Val Glu Glu Cys Thr Cys Glu
    115                 120                 125

Asp Cys Val Lys Ser Lys Pro Lys Gly Asp Ser Asp His Phe Phe Pro
        130                 135                 140

Leu Pro Ala Met Glu Glu Gly Ala Thr Ile Leu Val Thr Thr Lys Thr
145                 150                 155                 160

Gly Asp Tyr Gly Lys Ser Ser Val Pro Thr Ala Leu Gln Ser Val Met
                165                 170                 175

Gly Met Glu Lys Pro Thr His Thr Arg
                180                 185

<210> SEQ ID NO 11
<211> LENGTH: 129
<212> TYPE: PRT
<213> ORGANISM: homo sapiens

<400> SEQUENCE: 11

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
    50                  55                  60

Leu Gly Cys Ala Ala Ala Pro Pro Ala Pro Phe Arg Leu Leu Trp Pro
65              70                  75                  80

Ile Leu Gly Gly Ala Leu Ser Leu Thr Phe Val Leu Gly Leu Leu Ser
            85                  90                  95

Gly Phe Leu Val Trp Arg Arg Cys Arg Arg Arg Glu Lys Phe Thr Thr
        100                 105                 110

Pro Ile Glu Glu Thr Gly Gly Glu Gly Cys Pro Ala Val Ala Leu Ile
    115                 120                 125

Gln

<210> SEQ ID NO 12
<211> LENGTH: 41
<212> TYPE: PRT
<213> ORGANISM: homo sapiens
<220> FEATURE:
```

```
<221> NAME/KEY: DOMAIN
<222> LOCATION: (1)...(41)
<223> OTHER INFORMATION: cysteine rich

<400> SEQUENCE: 12

Gly Glu Gln Ala Pro Gly Thr Ala Pro Cys Ser Arg Gly Ser Ser Trp
  1               5                  10                  15

Ser Ala Asp Leu Asp Lys Cys Met Asp Cys Ala Ser Cys Arg Ala Arg
             20                  25                  30

Pro His Ser Asp Phe Cys Leu Gly Cys
         35                  40

<210> SEQ ID NO 13
<211> LENGTH: 129
<212> TYPE: PRT
<213> ORGANISM: mus musculus

<400> SEQUENCE: 13

Met Ala Pro Gly Trp Pro Arg Ser Leu Pro Gln Ile Leu Val Leu Gly
  1               5                  10                  15

Phe Gly Leu Val Leu Met Arg Ala Ala Ala Gly Glu Gln Ala Pro Gly
             20                  25                  30

Thr Ser Pro Cys Ser Ser Gly Ser Ser Trp Ser Ala Asp Leu Asp Lys
         35                  40                  45

Cys Met Asp Cys Ala Ser Cys Pro Ala Arg Pro His Ser Asp Phe Cys
 50                  55                  60

Leu Gly Cys Ala Ala Ala Pro Pro Ala His Phe Arg Leu Leu Trp Pro
 65                  70                  75                  80

Ile Leu Gly Gly Ala Leu Ser Leu Val Leu Val Leu Ala Leu Val Ser
                 85                  90                  95

Ser Phe Leu Val Trp Arg Arg Cys Arg Arg Arg Glu Lys Phe Thr Thr
                100                 105                 110

Pro Ile Glu Glu Thr Gly Gly Glu Gly Cys Pro Gly Val Ala Leu Ile
                115                 120                 125

Gln

<210> SEQ ID NO 14
<211> LENGTH: 447
<212> TYPE: PRT
<213> ORGANISM: homo sapiens

<400> SEQUENCE: 14

Met Ala His Val Gly Asp Cys Thr Gln Thr Pro Trp Leu Pro Val Leu
  1               5                  10                  15

Val Val Ser Leu Met Cys Ser Ala Arg Ala Glu Tyr Ser Asn Cys Gly
             20                  25                  30

Glu Asn Glu Tyr Tyr Asn Gln Thr Thr Gly Leu Cys Gln Glu Cys Pro
         35                  40                  45

Pro Cys Gly Pro Gly Glu Glu Pro Tyr Leu Ser Cys Gly Tyr Gly Thr
 50                  55                  60

Lys Asp Glu Asp Tyr Gly Cys Val Pro Cys Pro Ala Glu Lys Phe Ser
 65                  70                  75                  80

Lys Gly Gly Tyr Gln Ile Cys Arg Arg His Lys Asp Cys Glu Gly Phe
                 85                  90                  95

Phe Arg Ala Thr Val Leu Thr Pro Gly Asp Met Glu Asn Asp Ala Glu
                100                 105                 110

Cys Gly Pro Cys Leu Pro Gly Tyr Tyr Met Leu Glu Asn Arg Pro Arg
```

-continued

```
                115                 120                 125
Asn Ile Tyr Gly Met Val Cys Tyr Ser Cys Leu Leu Ala Pro Pro Asn
            130                 135                 140

Thr Lys Glu Cys Val Gly Ala Thr Ser Gly Ser Ala Asn Phe Pro
145                 150                 155                 160

Gly Thr Ser Gly Ser Ser Thr Leu Ser Pro Phe Gln His Ala His Lys
                165                 170                 175

Glu Leu Ser Gly Gln Gly His Leu Ala Thr Ala Leu Ile Ile Ala Met
            180                 185                 190

Ser Thr Ile Phe Ile Met Ala Ile Ala Ile Val Leu Ile Ile Met Phe
        195                 200                 205

Tyr Ile Leu Lys Thr Lys Pro Ser Ala Pro Ala Cys Cys Thr Ser His
    210                 215                 220

Pro Gly Lys Ser Val Glu Ala Gln Val Ser Lys Asp Glu Lys Lys
225                 230                 235                 240

Glu Ala Pro Asp Asn Val Val Met Phe Ser Lys Asp Glu Phe Glu
                245                 250                 255

Lys Leu Thr Ala Thr Pro Ala Lys Pro Thr Lys Ser Glu Asn Asp Ala
            260                 265                 270

Ser Ser Glu Asn Glu Gln Leu Leu Ser Arg Ser Val Asp Ser Asp Glu
        275                 280                 285

Glu Pro Ala Pro Asp Lys Gln Gly Ser Pro Glu Leu Cys Leu Leu Ser
    290                 295                 300

Leu Val His Leu Ala Arg Glu Lys Ser Ala Thr Ser Asn Lys Ser Ala
305                 310                 315                 320

Gly Ile Gln Ser Arg Arg Lys Lys Ile Leu Asp Val Tyr Ala Asn Val
                325                 330                 335

Cys Gly Val Val Glu Gly Leu Ser Pro Thr Glu Leu Pro Phe Asp Cys
            340                 345                 350

Leu Glu Lys Thr Ser Arg Met Leu Ser Ser Thr Tyr Asn Ser Glu Lys
        355                 360                 365

Ala Val Val Lys Thr Trp Arg His Leu Ala Glu Ser Phe Gly Leu Lys
    370                 375                 380

Arg Asp Glu Ile Gly Gly Met Thr Asp Gly Met Gln Leu Phe Asp Arg
385                 390                 395                 400

Ile Ser Thr Ala Gly Tyr Ser Ile Pro Glu Leu Leu Lys Leu Val Gln
                405                 410                 415

Ile Glu Arg Leu Asp Ala Val Glu Ser Leu Cys Ala Asp Ile Leu Glu
            420                 425                 430

Trp Ala Gly Val Val Pro Pro Ala Ser Gln Pro His Ala Ala Ser
        435                 440                 445

<210> SEQ ID NO 15
<211> LENGTH: 49
<212> TYPE: PRT
<213> ORGANISM: homo sapiens
<220> FEATURE:
<221> NAME/KEY: DOMAIN
<222> LOCATION: (1)...(49)
<223> OTHER INFORMATION: cysteine rich

<400> SEQUENCE: 15

Arg Ala Glu Tyr Ser Asn Cys Gly Glu Asn Glu Tyr Tyr Asn Gln Thr
1               5                   10                  15

Thr Gly Leu Cys Gln Glu Cys Pro Pro Cys Gly Pro Gly Glu Glu Pro
            20                  25                  30
```

Tyr Leu Ser Cys Gly Tyr Gly Thr Lys Asp Glu Asp Tyr Gly Cys Val
            35                  40                  45

Pro

<210> SEQ ID NO 16
<211> LENGTH: 448
<212> TYPE: PRT
<213> ORGANISM: mus musculus

<400> SEQUENCE: 16

Met Ala His Val Gly Asp Cys Lys Trp Met Ser Trp Leu Pro Val Leu
  1               5                  10                  15

Val Val Ser Leu Met Cys Ser Ala Lys Ala Glu Asp Ser Asn Cys Gly
                20                  25                  30

Glu Asn Glu Tyr His Asn Gln Thr Gly Leu Cys Gln Gln Cys Pro
            35                  40                  45

Pro Cys Arg Pro Gly Glu Glu Pro Tyr Met Ser Cys Gly Tyr Gly Thr
        50                  55                  60

Lys Asp Asp Tyr Gly Cys Val Pro Cys Pro Ala Glu Lys Phe Ser
65                  70                  75                  80

Lys Gly Gly Tyr Gln Ile Cys Arg Arg His Lys Asp Cys Glu Gly Phe
                85                  90                  95

Phe Arg Ala Thr Val Leu Thr Pro Gly Asp Met Glu Asn Asp Ala Glu
            100                 105                 110

Cys Gly Pro Cys Leu Pro Gly Tyr Tyr Met Leu Glu Asn Arg Pro Arg
        115                 120                 125

Asn Ile Tyr Gly Met Val Cys Tyr Ser Cys Leu Leu Ala Pro Pro Asn
    130                 135                 140

Thr Lys Glu Cys Val Gly Ala Thr Ser Gly Val Ser Ala His Ser Ser
145                 150                 155                 160

Ser Thr Ser Gly Gly Ser Thr Leu Ser Pro Phe Gln His Ala His Lys
                165                 170                 175

Glu Leu Ser Gly Gln Gly His Leu Ala Thr Ala Leu Ile Ile Ala Met
            180                 185                 190

Ser Thr Ile Phe Ile Met Ala Ile Ala Ile Val Leu Ile Ile Met Phe
        195                 200                 205

Tyr Ile Met Lys Thr Lys Pro Ser Ala Pro Ala Cys Cys Ser Ser Pro
    210                 215                 220

Pro Gly Lys Ser Ala Glu Ala Pro Ala Asn Thr His Glu Glu Lys Lys
225                 230                 235                 240

Glu Ala Pro Asp Ser Val Val Thr Phe Pro Glu Asn Gly Glu Phe Gln
                245                 250                 255

Lys Leu Thr Ala Thr Pro Thr Lys Thr Pro Lys Ser Glu Asn Asp Ala
            260                 265                 270

Ser Ser Glu Asn Glu Gln Leu Leu Ser Arg Ser Val Asp Ser Asp Glu
        275                 280                 285

Glu Pro Ala Pro Asp Lys Gln Gly Ser Pro Glu Leu Cys Leu Leu Ser
    290                 295                 300

Leu Val His Leu Ala Arg Glu Lys Ser Val Thr Ser Asn Lys Ser Ala
305                 310                 315                 320

Gly Ile Gln Ser Arg Arg Lys Lys Ile Leu Asp Val Tyr Ala Asn Val
                325                 330                 335

Cys Gly Val Val Glu Gly Leu Ser Pro Thr Glu Leu Pro Phe Asp Cys
            340                 345                 350

-continued

```
Leu Glu Lys Thr Ser Arg Met Leu Ser Ser Thr Tyr Asn Ser Glu Lys
            355                 360                 365

Ala Val Val Lys Thr Trp Arg His Leu Ala Glu Ser Phe Gly Leu Lys
            370                 375                 380

Arg Asp Glu Ile Gly Gly Met Thr Asp Gly Met Gln Leu Phe Asp Arg
385                 390                 395                 400

Ile Ser Thr Ala Gly Tyr Ser Ile Pro Glu Leu Leu Thr Lys Leu Val
                405                 410                 415

Gln Ile Glu Arg Leu Asp Ala Val Glu Ser Leu Cys Ala Asp Ile Leu
            420                 425                 430

Glu Trp Ala Gly Val Val Pro Pro Ala Ser Pro Pro Ala Ala Ser
            435                 440                 445

<210> SEQ ID NO 17
<211> LENGTH: 297
<212> TYPE: PRT
<213> ORGANISM: homo sapiens

<400> SEQUENCE: 17

Met Asp Cys Gln Glu Asn Glu Tyr Trp Asp Gln Trp Gly Arg Cys Val
1               5                   10                  15

Thr Cys Gln Arg Cys Gly Pro Gly Gln Glu Leu Ser Lys Asp Cys Gly
            20                  25                  30

Tyr Gly Glu Gly Gly Asp Ala Tyr Cys Thr Ala Cys Pro Pro Arg Arg
        35                  40                  45

Tyr Lys Ser Ser Trp Gly His His Arg Cys Gln Ser Cys Ile Thr Cys
    50                  55                  60

Ala Val Ile Asn Arg Val Gln Lys Val Asn Cys Thr Ala Thr Ser Asn
65                  70                  75                  80

Ala Val Cys Gly Asp Cys Leu Pro Arg Phe Tyr Arg Lys Thr Arg Ile
                85                  90                  95

Gly Gly Leu Gln Asp Gln Glu Cys Ile Pro Cys Thr Lys Gln Thr Pro
            100                 105                 110

Thr Ser Glu Val Gln Cys Ala Phe Gln Leu Ser Leu Val Glu Ala Asp
            115                 120                 125

Ala Pro Thr Val Pro Pro Gln Glu Ala Thr Leu Val Ala Leu Val Ser
130                 135                 140

Ser Leu Leu Val Val Phe Thr Leu Ala Phe Leu Gly Leu Phe Phe Leu
145                 150                 155                 160

Tyr Cys Lys Gln Phe Phe Asn Arg His Cys Gln Arg Gly Gly Leu Leu
                165                 170                 175

Gln Phe Glu Ala Asp Lys Thr Ala Lys Glu Glu Ser Leu Phe Pro Val
            180                 185                 190

Pro Pro Ser Lys Glu Thr Ser Ala Glu Ser Gln Val Ser Glu Asn Ile
            195                 200                 205

Phe Gln Thr Gln Pro Leu Asn Pro Ile Leu Glu Asp Asp Cys Ser Ser
        210                 215                 220

Thr Ser Gly Phe Pro Thr Gln Glu Ser Phe Thr Met Ala Ser Cys Thr
225                 230                 235                 240

Ser Glu Ser His Ser His Trp Val His Ser Pro Ile Glu Cys Thr Glu
                245                 250                 255

Leu Asp Leu Gln Lys Phe Ser Ser Ser Ala Ser Tyr Thr Gly Ala Glu
            260                 265                 270

Thr Leu Gly Gly Asn Thr Val Glu Ser Thr Gly Asp Arg Leu Glu Leu
```

```
                    275                 280                 285

Asn Val Pro Phe Glu Val Pro Ser Pro
    290                 295

<210> SEQ ID NO 18
<211> LENGTH: 42
<212> TYPE: PRT
<213> ORGANISM: homo sapiens

<400> SEQUENCE: 18

Asp Cys Gln Glu Asn Glu Tyr Trp Asp Gln Trp Gly Arg Cys Val Thr
  1               5                  10                  15

Cys Gln Arg Cys Gly Pro Gly Gln Glu Leu Ser Lys Asp Cys Gly Tyr
                 20                  25                  30

Gly Glu Gly Gly Asp Ala Tyr Cys Thr Ala
             35                  40

<210> SEQ ID NO 19
<211> LENGTH: 292
<212> TYPE: PRT
<213> ORGANISM: homo sapiens

<400> SEQUENCE: 19

Met Ser Gly Leu Gly Arg Ser Arg Arg Gly Gly Arg Ser Arg Val Asp
  1               5                  10                  15

Gln Glu Glu Arg Phe Pro Gln Gly Leu Trp Thr Gly Val Ala Met Arg
                 20                  25                  30

Ser Cys Pro Glu Glu Gln Tyr Trp Asp Pro Leu Leu Gly Thr Cys Met
             35                  40                  45

Ser Cys Lys Thr Ile Cys Asn His Gln Ser Gln Arg Thr Cys Ala Ala
         50                  55                  60

Phe Cys Arg Ser Leu Ser Cys Arg Lys Glu Gln Gly Lys Phe Tyr Asp
 65                  70                  75                  80

His Leu Leu Arg Asp Cys Ile Ser Cys Ala Ser Ile Cys Gly Gln His
                 85                  90                  95

Pro Lys Gln Cys Ala Tyr Phe Cys Glu Asn Lys Leu Arg Ser Pro Val
                100                 105                 110

Asn Leu Pro Pro Glu Leu Arg Arg Gln Arg Ser Gly Glu Val Glu Asn
            115                 120                 125

Asn Ser Asp Asn Ser Gly Arg Tyr Gln Gly Leu Glu His Arg Gly Ser
        130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Cys Arg Ala Pro Thr
225                 230                 235                 240

Gln Glu Ser Ala Val Thr Pro Gly Thr Pro Asp Pro Thr Cys Ala Gly
                245                 250                 255

Arg Trp Gly Cys His Thr Arg Thr Thr Val Leu Gln Pro Cys Pro His
```

```
                    260                 265                 270
Ile Pro Asp Ser Gly Leu Gly Ile Val Cys Val Pro Ala Gln Glu Gly
            275                 280                 285

Gly Pro Gly Ala
        290

<210> SEQ ID NO 20
<211> LENGTH: 48
<212> TYPE: PRT
<213> ORGANISM: homo sapiens
<220> FEATURE:
<221> NAME/KEY: DOMAIN
<222> LOCATION: (1)...(48)
<223> OTHER INFORMATION: cysteine rich

<400> SEQUENCE: 20

Pro Gln Gly Leu Trp Thr Gly Val Ala Met Arg Ser Cys Pro Glu Glu
  1               5                  10                  15

Gln Tyr Trp Asp Pro Leu Leu Gly Thr Cys Met Ser Cys Lys Thr Ile
                 20                  25                  30

Cys Asn His Gln Ser Gln Arg Thr Cys Ala Ala Phe Cys Arg Ser Leu
             35                  40                  45

<210> SEQ ID NO 21
<211> LENGTH: 249
<212> TYPE: PRT
<213> ORGANISM: mus musculus

<400> SEQUENCE: 21

Met Ala Met Ala Phe Cys Pro Lys Asp Gln Tyr Trp Asp Ser Ser Arg
  1               5                  10                  15

Lys Ser Cys Val Ser Cys Ala Leu Thr Cys Ser Gln Arg Ser Gln Arg
                 20                  25                  30

Thr Cys Thr Asp Phe Cys Lys Phe Ile Asn Cys Arg Lys Glu Gln Gly
             35                  40                  45

Arg Tyr Tyr Asp His Leu Leu Gly Ala Cys Val Ser Cys Asp Ser Thr
         50                  55                  60

Cys Thr Gln His Pro Gln Gln Cys Ala His Phe Cys Glu Lys Arg Pro
 65                  70                  75                  80

Arg Ser Gln Ala Asn Leu Gln Pro Glu Leu Gly Arg Pro Gln Ala Gly
                 85                  90                  95

Glu Val Glu Val Arg Ser Asp Asn Ser Gly Arg His Gln Gly Ser Glu
            100                 105                 110

His Gly Pro Gly Leu Arg Leu Ser Ser Asp Gln Leu Thr Leu Tyr Cys
            115                 120                 125

Thr Leu Gly Val Cys Leu Cys Ala Ile Phe Cys Cys Phe Leu Val Ala
        130                 135                 140

Leu Ala Ser Phe Leu Arg Arg Arg Gly Glu Pro Leu Pro Ser Gln Pro
145                 150                 155                 160

Ala Gly Pro Arg Gly Ser Gln Ala Asn Ser Pro His Ala His Arg Pro
                165                 170                 175

Val Thr Glu Ala Cys Asp Glu Val Thr Ala Ser Pro Gln Pro Val Glu
            180                 185                 190

Thr Cys Ser Phe Cys Phe Pro Glu Arg Ser Ser Pro Thr Gln Glu Ser
            195                 200                 205

Ala Pro Arg Ser Leu Gly Ile His Gly Phe Ala Gly Thr Ala Ala Pro
        210                 215                 220
```

```
Gln Pro Cys Met Arg Ala Thr Val Gly Gly Leu Gly Val Leu Arg Ala
225                 230                 235                 240

Ser Thr Gly Asp Ala Arg Pro Ala Thr
                245

<210> SEQ ID NO 22
<211> LENGTH: 355
<212> TYPE: PRT
<213> ORGANISM: homo sapiens

<400> SEQUENCE: 22

Met Gly Pro Gly Arg Cys Leu Leu Thr Ala Leu Leu Leu Ala Leu
  1               5                  10                  15

Ala Pro Pro Pro Glu Ala Ser Gln Tyr Cys Gly Arg Leu Glu Tyr Trp
                 20                  25                  30

Asn Pro Asp Asn Lys Cys Cys Ser Ser Cys Leu Gln Arg Phe Gly Pro
                 35                  40                  45

Pro Pro Cys Pro Asp Tyr Glu Phe Arg Glu Asn Cys Gly Leu Asn Asp
 50                  55                  60

His Gly Asp Phe Val Thr Pro Pro Phe Arg Lys Cys Ser Ser Gly Gln
 65                  70                  75                  80

Cys Asn Pro Asp Gly Ala Glu Leu Cys Ser Pro Cys Gly Gly Gly Ala
                 85                  90                  95

Val Thr Pro Thr Pro Ala Ala Gly Gly Arg Thr Pro Trp Arg Cys
                100                 105                 110

Arg Glu Arg Pro Val Pro Ala Lys Gly His Cys Pro Leu Thr Pro Gly
            115                 120                 125

Asn Pro Gly Ala Pro Ser Ser Gln Glu Arg Ser Ser Pro Ala Ser Ser
130                 135                 140

Ile Ala Trp Arg Thr Pro Glu Pro Val Pro Gln Gln Ala Trp Pro Asn
145                 150                 155                 160

Phe Leu Pro Leu Val Val Leu Val Leu Leu Thr Leu Ala Val Ile
                165                 170                 175

Ala Ile Leu Leu Phe Ile Leu Leu Trp His Leu Cys Trp Pro Lys Glu
            180                 185                 190

Lys Ala Asp Pro Tyr Pro Tyr Pro Gly Leu Val Cys Gly Val Pro Asn
            195                 200                 205

Thr His Thr Pro Ser Ser Ser His Leu Ser Ser Pro Gly Ala Leu Glu
210                 215                 220

Thr Gly Asp Thr Trp Lys Glu Ala Ser Leu Leu Pro Leu Leu Ser Arg
225                 230                 235                 240

Glu Leu Ser Ser Leu Ala Ser Gln Pro Leu Ser Arg Leu Leu Asp Glu
                245                 250                 255

Leu Glu Val Leu Glu Glu Leu Ile Val Leu Leu Asp Pro Glu Pro Gly
                260                 265                 270

Pro Gly Gly Gly Met Ala His Gly Thr Thr Arg His Leu Ala Ala Arg
            275                 280                 285

Tyr Gly Leu Pro Ala Ala Trp Ser Thr Phe Ala Tyr Ser Leu Arg Pro
290                 295                 300

Ser Arg Ser Pro Leu Arg Ala Leu Ile Glu Met Val Ala Arg Glu
305                 310                 315                 320

Pro Ser Ala Ser Leu Gly Gln Leu Gly Thr His Leu Ala Gln Leu Gly
                325                 330                 335

Arg Ala Asp Ala Leu Arg Val Leu Ser Lys Leu Gly Ser Gly Val
                340                 345                 350
```

```
Cys Trp Ala
        355

<210> SEQ ID NO 23
<211> LENGTH: 27
<212> TYPE: PRT
<213> ORGANISM: homo sapiens
<220> FEATURE:
<221> NAME/KEY: DOMAIN
<222> LOCATION: (1)...(27)
<223> OTHER INFORMATION: cysteine rich

<400> SEQUENCE: 23

Pro Glu Ala Ser Gln Tyr Cys Gly Arg Leu Glu Tyr Trp Asn Pro Asp
 1               5                  10                  15

Asn Lys Cys Cys Ser Ser Cys Leu Gln Arg Phe
            20                  25

<210> SEQ ID NO 24
<211> LENGTH: 344
<212> TYPE: PRT
<213> ORGANISM: mus musculus

<400> SEQUENCE: 24

Met Gly Pro Ser Trp Leu Leu Trp Thr Val Ala Val Ala Val Leu Leu
 1               5                  10                  15

Leu Thr Arg Ala Ala Ser Met Glu Ala Ser Ser Phe Cys Gly His Leu
                20                  25                  30

Glu Tyr Trp Asn Ser Asp Lys Arg Cys Cys Ser Arg Cys Leu Gln Arg
            35                  40                  45

Phe Gly Pro Pro Ala Cys Pro Asp His Glu Phe Thr Glu Asn Cys Gly
    50                  55                  60

Leu Asn Asp Phe Gly Asp Thr Val Ala His Pro Phe Lys Lys Cys Ser
65                  70                  75                  80

Pro Gly Tyr Cys Asn Pro Asn Gly Thr Glu Leu Cys Ser Gln Cys Ser
                85                  90                  95

Ser Gly Ala Ala Ala Pro Ala His Val Glu Ser Pro Gly Arg Thr
                100                 105                 110

His Lys Gln Cys Arg Lys Pro Val Pro Pro Lys Asp Val Cys Pro Leu
            115                 120                 125

Lys Pro Glu Asp Ala Gly Ala Ser Ser Pro Gly Arg Trp Ser Leu
    130                 135                 140

Gly Gln Thr Thr Lys Asn Glu Val Ser Ser Gln Pro Gly Phe Val Ser
145                 150                 155                 160

Ala Ser Val Leu Pro Leu Ala Val Leu Pro Leu Leu Val Leu Leu
                165                 170                 175

Leu Ile Leu Ala Val Val Leu Leu Ser Leu Phe Lys Arg Lys Val Arg
            180                 185                 190

Ser Arg Pro Ser Ser Ser Ser Ala Phe Gly Asp Pro Ser Thr Ser Leu
    195                 200                 205

His Tyr Trp Pro Cys Pro Gly Thr Leu Glu Val Leu Glu Ser Arg Asn
            210                 215                 220

Arg Gly Lys Ala Asn Leu Leu Gln Leu Ser Ser Trp Glu Leu Gln Gly
225                 230                 235                 240

Leu Ala Ser Gln Pro Leu Ser Leu Leu Asp Glu Leu Glu Val Leu
                245                 250                 255

Glu Glu Leu Ile Met Leu Leu Asp Pro Glu Pro Gly Pro Ser Gly Ser
```

-continued

```
                260                 265                 270
Thr Ala Tyr Gly Thr Thr Arg His Leu Ala Ala Arg Tyr Gly Leu Pro
            275                 280                 285
Ala Thr Trp Ser Thr Phe Ala Tyr Ser Leu Arg Pro Ser Arg Ser Pro
        290                 295                 300
Leu Arg Ala Leu Ile Glu Met Val Val Ala Arg Glu Pro Ser Ala Thr
305                 310                 315                 320
Leu Gly Gln Phe Gly Thr Tyr Leu Ala Gln Leu Gly Arg Thr Asp Ala
                325                 330                 335
Leu Gln Val Leu Ser Lys Leu Gly
            340

<210> SEQ ID NO 25
<211> LENGTH: 199
<212> TYPE: PRT
<213> ORGANISM: rat norvegicus

<400> SEQUENCE: 25

Met Ala Leu Gln Cys Leu Met Leu Leu Thr Gly Leu Val Gly Gly
1               5                   10                  15
Met Ser Lys Ser Thr Glu Ser Lys Ala Gln Gln Pro Glu Cys Cys Met
                20                  25                  30
Asp Val Val Asp Val Asn Ala Thr Cys Leu Gly Thr Gly Leu Cys Gly
            35                  40                  45
Pro Gly Cys Tyr Arg His Trp Asn Ala Asp Gly Ser Ala Ser Cys Val
        50                  55                  60
Arg Cys Trp Asn Gly Thr Leu Pro Thr Tyr Asn Gly Ser Glu Cys Arg
65                  70                  75                  80
Ile Leu Thr Gly Arg Gly Met Gln Phe Pro Met Asn Arg Ser Thr Gly
                85                  90                  95
Thr Pro Gly Gln Pro His Phe Gly Gly Pro His Val Ala Ala Ser Leu
            100                 105                 110
Phe Leu Gly Thr Leu Phe Ile Ser Thr Gly Leu Ile Leu Ser Val Ala
        115                 120                 125
Gly Phe Phe Tyr Leu Lys Arg Ser Ser Lys Leu Pro Glu Val Phe Tyr
    130                 135                 140
Arg Arg Asp Arg Ala Pro Val Leu Gln Pro Gly Glu Thr Ala Ala Met
145                 150                 155                 160
Val Pro Leu Pro Gln Ser Ser Val Arg Lys Pro Arg Tyr Ile Arg Arg
                165                 170                 175
Glu Gln His Pro Glu Lys Asn Arg Asp Pro Ser Ala Phe Ser Thr Val
            180                 185                 190
Glu Ala His Ile Ser Asn Val
        195

<210> SEQ ID NO 26
<211> LENGTH: 196
<212> TYPE: PRT
<213> ORGANISM: bos taurus

<400> SEQUENCE: 26

Met Ala Leu Arg Arg Ala Val Phe Leu Ala Gly Leu Leu Val Glu Val
1               5                   10                  15
Ala Ser Arg Ala Ser Gly Thr Ala Gly Gln Gln Pro Glu Cys Cys Val
                20                  25                  30
Asp Ala Gly Asn Ile Asn Ala Thr Cys Pro Gly Thr Ser Leu Cys Gly
```

-continued

```
                 35                  40                  45
Pro Gly Cys Tyr Gly Arg Pro Ala Glu Asp Gly Ser Val Ser Cys Val
        50                  55                  60

Gln Cys Arg Asn Gly Thr His Asn Ser Ser Glu Cys Arg Gly Leu Ala
 65                  70                  75                  80

Gly Arg Gly Ala Gln Phe Pro Val Asn Lys Ser Ala Gly Met Pro Gly
                85                  90                  95

Trp Gln Ser Val Gly Gly Pro Gln Val Ala Ala Ser Leu Phe Leu Gly
               100                 105                 110

Thr Phe Leu Ile Ser Ser Gly Leu Ile Leu Ser Val Ala Ala Phe Phe
               115                 120                 125

Tyr Leu Lys Arg Ala Ser Lys Leu Pro Lys Val Phe Tyr Gly Arg Asn
               130                 135                 140

Arg Ala Pro Ala Leu Gln Pro Gly Glu Ala Ala Val Met Ile Pro Pro
145                 150                 155                 160

Pro Gln Ser Ser Arg Asp Val Gly Pro Thr Thr Val Ser Val Glu
               165                 170                 175

Ala Arg Val Ser Asn Val Val Arg Lys Pro Arg Tyr Val Arg Arg Glu
               180                 185                 190

Arg Pro Leu Asp
       195

<210> SEQ ID NO 27
<211> LENGTH: 196
<212> TYPE: PRT
<213> ORGANISM: gallus gallus

<400> SEQUENCE: 27

Met Glu Val Pro Tyr Val Leu Leu Leu Thr Arg Leu Val Ala Glu Val
  1               5                  10                  15

Ala Ser Lys Ser Thr Glu Ser Ser Val Ser Ser Cys Ile Lys Cys Lys
                 20                  25                  30

Asn Glu Thr Leu Pro Tyr Asn Leu Thr Asp Cys Arg Asn Thr Gly Ile
                 35                  40                  45

Arg Gly Met Asn Phe Gln Met Asn Ile Ser Thr Val Thr Pro Phe Ile
         50                  55                  60

Gln Asn Ile Gly Gly Pro Glu Val Ala Ala Ser Leu Ile Leu Gly Thr
 65                  70                  75                  80

Phe Phe Ile Ser Glu Thr Glu Cys Cys Val Asp Met Leu Glu Ser Asn
                 85                  90                  95

Ser Ser Cys Pro Val Ala Asn Gln Cys Ser Pro Gly Cys Tyr Arg Arg
                100                 105                 110

Trp Asn Glu Asp Gly Ser Leu Phe Leu Ile Leu Ser Val Ala Ser Phe
               115                 120                 125

Phe Tyr Leu Lys Arg Ala Asn Lys Leu Pro Asn Val Phe Tyr Arg Arg
               130                 135                 140

Asn Lys Ala Pro Ala Leu Gln Pro Gly Glu Ala Ala Met Ile Pro
145                 150                 155                 160

Pro Pro Gln Ser Ser Val Arg Lys Pro Arg Arg Ala Thr Asp Pro Ala
               165                 170                 175

Ala Phe Pro Gly Glu Ala Arg Ile Ser Asn Val Tyr Val Arg Arg Glu
               180                 185                 190

Arg Pro Leu Asp
       195
```

<210> SEQ ID NO 28
<211> LENGTH: 193
<212> TYPE: PRT
<213> ORGANISM: xenopus laevis

<400> SEQUENCE: 28

Met Ala Val Pro Cys Ala Ile Phe Leu Gly Arg Phe Ile Ala Asp Thr
1               5                   10                  15

Val Ser Ile Leu Ser Val Val Asn Asp Cys Cys Ser Glu Arg Asp Leu
            20                  25                  30

Asn Gly Ser Cys Pro Ile Ser His Arg Cys Ser Pro Gly Cys Phe Arg
        35                  40                  45

Leu Trp Ser Glu Asp Gly Ser Ser Thr Cys Ile Lys Cys Lys Asn Glu
    50                  55                  60

Thr Gly Ser Glu Val Ile His Asn Val Thr Glu Cys Arg Asn Phe Ser
65                  70                  75                  80

Ser Ser Thr Leu Asp Val Asn Leu Asn Ala Ser Ile Thr Pro Ser Val
                85                  90                  95

Ser His Asn Leu Gly Ser Pro Gly Ile Ala Ala Ser Leu Leu Leu Gly
            100                 105                 110

Ile Leu Phe Ile Ser Leu Phe Leu Ile Leu Ser Val Ala Ser Phe Phe
        115                 120                 125

Tyr Leu Lys Arg Ser Gln Lys Leu Pro Glu Ile Phe Tyr Arg Arg Asn
    130                 135                 140

Lys Ala Ser Ile Phe Gln Pro Ser Glu Met Ala Ser Met Ile Pro Asn
145                 150                 155                 160

Pro Asn Ser Ser Val Arg Lys Pro Arg Tyr Val Arg Arg Glu Arg Thr
                165                 170                 175

Arg Thr Thr Ala Val Pro Glu Ser Ser Val Asp Thr Arg Val Ser Asn
            180                 185                 190

Val

<210> SEQ ID NO 29
<211> LENGTH: 1938
<212> TYPE: DNA
<213> ORGANISM: homo sapiens

<400> SEQUENCE: 29
gaattcggca cgagggggga ctgggccggg gtctgcaggg ctcagctgag cccatgagct    60
cccagagcta acccctgaac acccaggcgg gcaaagggct gatgtcggta gtccccatcc   120
tggaggggca ggctctgcgc atctgctcct ggcatggcgc tgcggcacct cgccctcctg   180
gctggccttc tcgtgggagt cgccagcaag tccatggaga cacggcccag ctgcccgag    240
tgctgtgtgg atgtggtggg cgtcaacgcc agctgcccag gcgcaagtct gtgtggtcca   300
ggctgttaca ggcgctggaa cgcggacggg agcgccagct cgtccgctg tgggaacgga    360
accctcccag cctacaacgg ctccgagtgt agaagctttg ctggcccggg tgcgccattc   420
cccatgaaca gaagctcagg gaccccggg cggccacatc ctggggctcc gcgcgtggcc    480
gcctccctct tcctgggcac gttcttcatt agctccggcc tcatcctctt cgtagctggg   540
ttcttctacc tcaagcgctc cagtaaactc cccaggcct gctacagaag aaacaaagct    600
ccggccctgc agcctggcga agccgctgca atgatccccc cgccacagtc ctcagctcca   660
cccgaggaca gacgcagccg gcctccgcca ggccctcctg agcagccatc gcttcagtgg   720
tgctgggtca ggcggaccca agagtcagcc cgtacggaag ccgcgctacg tcaggcggga   780

```
gcggcccctg  gacagggcca  cggatcccgc  tgccttcccg  ggggaggccc  gtatcagcaa    840
tgtctgacct  ggaggccgag  accacgccac  gcacttggcg  gcagggaccc  ggaggccgac    900
cccttggcgg  gaaccagcac  aaagtgttgg  catcgcccgg  cgcccgggac  agtcctgggc    960
acagcctcgg  ctctgggtcc  ctccgcctcc  cagcgacgga  cgccaaaggg  tcccgggccg   1020
cctgaggctc  ctccccacca  cagccatctc  gtttatcgga  ccaggagcag  gcatccatga   1080
gacctcagag  cttcagatcg  aggccttggg  gggtccgggc  cccccagga   aacacggtga   1140 ggccccagcg  cctgcagcca  aagctggcac  gatctatggg  gcaggtgccg  ctctgcctag   1200
aaaagccagg  ggctctgctg  ccgtgccctc  cagagcccac  agcgggcagg  actcctccag   1260
caccaccaca  cccagtggcc  cgagacccct  ctgagaacag  tgaggctggt  cctcgtgccg   1320
ttccagccgg  tgcccggcca  gtggggagga  cacagcctag  gaaccagctg  cctgagacca   1380
gggtgcctct  gggctgtcct  cccgcgtggc  ggagacccca  agcacgcagc  cacccatttc   1440
cggagctgca  ggatagagct  tcctcttgat  ctctgttttt  aagcagaaat  tcattgtgca   1500
gaaaagtcct  ccagagctct  gtggcccgc   tcggatccgc  tggaccccca  tgcctggctg   1560
atccctgccc  acgtggggca  ggcccacatc  taacccccac  aagtcactgc  ctcactgcac   1620
ctgccaaggc  tgccctggcg  ctgagtcctg  gggtccctcc  cggagttcct  gggagaaagg   1680
cgccgtcgtg  gccgcctccc  gcacgccagg  cccgggctcc  accgtgggtc  tcagacgccc   1740
tgcggcaccg  gcaccgtctg  ctttagcatg  gaccccccat  ctgagggggtg  gcctggcctt   1800 cggggtcccc  acgtcccttt  gcgaagtcca  ctgtgggtgc  catcatggtc  tccgggacct   1860
gggccagcgg  gaacgtgggg  gcactgggtg  tgctgatata  aagtcggcat  tactcaagct   1920
gaaaaaaaaa  aaaaaaaa                                                    1938

<210> SEQ ID NO 30
<211> LENGTH: 308
<212> TYPE: PRT
<213> ORGANISM: homo sapiens

<400> SEQUENCE: 30

Met Ala Leu Arg His Leu Ala Leu Leu Ala Gly Leu Leu Val Gly Val
  1               5                  10                  15

Ala Ser Lys Ser Met Glu Asn Thr Ala Gln Leu Pro Glu Cys Cys Val
                 20                  25                  30

Asp Val Val Gly Val Asn Ala Ser Cys Pro Gly Ala Ser Leu Cys Gly
             35                  40                  45

Pro Gly Cys Tyr Arg Arg Trp Asn Ala Asp Gly Ser Ala Ser Cys Val
     50                  55                  60

Arg Cys Gly Asn Gly Thr Leu Pro Ala Tyr Asn Gly Ser Glu Cys Arg
 65                  70                  75                  80

Ser Phe Ala Gly Pro Gly Ala Pro Phe Pro Met Asn Arg Ser Ser Gly
                 85                  90                  95

Thr Pro Gly Arg Pro His Pro Gly Ala Pro Arg Val Ala Ala Ser Leu
            100                 105                 110

Phe Leu Gly Thr Phe Phe Ile Ser Ser Gly Leu Ile Leu Phe Val Ala
        115                 120                 125

Gly Phe Phe Tyr Leu Lys Arg Ser Ser Lys Leu Pro Arg Ala Cys Tyr
    130                 135                 140

Arg Arg Asn Lys Ala Pro Ala Leu Gln Pro Gly Glu Ala Ala Ala Met
145                 150                 155                 160
```

-continued

```
Ile Pro Pro Pro Gln Ser Ser Ala Pro Pro Glu Asp Arg Arg Ser Arg
            165                 170                 175

Pro Pro Pro Gly Pro Pro Glu Gln Pro Ser Leu Gln Trp Cys Trp Val
        180                 185                 190

Arg Arg Thr Gln Glu Ser Ala Arg Thr Glu Ala Ala Leu Arg Gln Ala
    195                 200                 205

Gly Ala Ala Pro Gly Gln Gly His Gly Ser Arg Cys Leu Pro Gly Gly
210                 215                 220

Gly Tyr Gln Gln Cys Leu Thr Trp Arg Pro Arg Pro His Ala
225                 230                 235                 240

Leu Gly Gly Arg Asp Pro Glu Ala Asp Pro Leu Ala Gly Thr Ser Thr
                245                 250                 255

Lys Cys Trp His Arg Pro Ala Pro Gly Thr Val Leu Gly Thr Ala Ser
                260                 265                 270

Ala Leu Gly Pro Ser Ala Ser Gln Arg Arg Thr Pro Lys Gly Pro Gly
            275                 280                 285

Pro Pro Glu Ala Pro Pro His His Ser His Leu Val Tyr Arg Thr Arg
    290                 295                 300

Ser Arg His Pro
305
```

```
<210> SEQ ID NO 31
<211> LENGTH: 1979
<212> TYPE: DNA
<213> ORGANISM: homo sapiens

<400> SEQUENCE: 31
```

| | | | | | |
|---|---|---|---|---|---|
| ctgagcccat | gagctcccag | agctaacccc | tgaacaccca | ggcgggcaaa | gggctgatgt | 60 |
| cggtagtccc | catcctggag | gggcaggctc | tgcgcatctg | ctcctggcat | ggcgctgcgg | 120 |
| cacctcgccc | tcctggctgg | ccttctcgtg | ggagtcgcca | gcaagtccat | ggagaacacg | 180 |
| gcccagctgc | ccgagtgctg | tgtggatgtg | gtgggcgtca | acgccagctg | cccaggcgca | 240 |
| agtctgtgtg | gtccaggctg | ttacaggcgc | tggaacgcgg | acgggagcgc | cagctgcgtc | 300 |
| cgctgtggga | acggaaccct | cccagcctac | aacggctccg | agtgtagaag | ctttgctggc | 360 |
| ccgggtgcgc | cattccccat | gaacagaagc | tcagggaccc | ccgggcggcc | acatcctggg | 420 |
| gctccgcgcg | tggccgcctc | cctcttcctg | ggcacgttct | tcatcagctc | cggcctcatc | 480 |
| ctctccgtag | ctgggttctt | ctacctcaag | cgctccagta | aactcccag | ggcctgctac | 540 |
| agaagaaaca | aagggccggc | ccccgcaggg | tccctgccag | gcagatggtc | cagccagcag | 600 |
| ttcggacccc | aagctccggc | cctgcagcct | ggcgaagccg | taagtaaccc | acatcatccg | 660 |
| ggctgagcgt | ccctggccgc | gtgtgcctgt | gccaggccat | cccgagtcct | cactctgcct | 720 |
| ttctctcctt | ttcaaggctg | caatgatccc | cccgccacag | tcctcagtac | ggaagccgcg | 780 |
| ctacgtcagg | cgggagcggc | ccctggacag | ggccacggat | cccgctgcct | tcccggggga | 840 |
| ggcccgtatc | agcaatgtct | gacctggagg | ccgagaccac | gccacgcact | tggcggcagg | 900 |
| gacccggagg | ccgacccctt | ggtgggaacc | agcacaaagt | gttggcatcg | cccggcgccc | 960 |
| gggacagtcc | tgggcacagc | ctcggctctg | agtccctccg | cctcccagcg | acggacgcca | 1020 |
| aagggtcccg | gccgcctga | ggctcctccc | caccacagcc | atctcgttta | tcggaccagc | 1080 |
| agcaggcatc | catgagacct | cagagcttca | gatcgaggcc | ttgggggtc | cgggcccccc | 1140 |
| caggaaacac | ggtgaggccc | cagcgcctgc | agccaaagct | ggcacgatct | atggggcagg | 1200 |
| tgccgctctg | cctagaaaag | ccaggggctc | tgctgccgtg | ccctccagag | cccacagcgg | 1260 |

-continued

```
gcaggactcc tccagcacca ccacacccag tggcccgaga cccctctgag aacagtgagg    1320
ctggtcctcg tgccgttcca gccggtgccc ggccagtggg gaggacacag cctaggaacc    1380
agctgcctga gaccagggtg cctctgggct gtcctcccgc gtggcggaga ccccaagcac    1440
gcagccaccc atttccggag ctgcaggata gagcttcctc ttgatctctg tttttaagca    1500
gaaattcatt gtgcagaaaa gtcctccaga gctctgtggc cccgctcgga tccgctggac    1560
ccccatgcct ggctgatccc tgcccacgtg gggcaggccc acatctaacc cccacaagtc    1620
actgcctcac tgcacctgcc aaggctgccc tggcgctgag tcctggggtc cctcccggag    1680
ttcctgggag aaaggcgccg tcgtggccgc ctcccgcacg ccaggcccgg gctccaccgt    1740
gggtctcaga cgcccgcgg caccggcacc gtctgcttta gcatgggacc cccatctgag     1800
gggtggcctg gccttcgggg tccccacgct cctttgcgaa gtccactgtg ggtgccatca    1860
tggtctccgg gacctgggcc agcgggaacg tgggggcact gggtgtgctg atataaagtc    1920
ggcattactc aaaaaaaaaa aaaaaaaaaa aaaaaaaaaa aaaaaaaaaa aaaaaaaa      1979
```

<210> SEQ ID NO 32
<211> LENGTH: 185
<212> TYPE: PRT
<213> ORGANISM: homo sapiens

<400> SEQUENCE: 32

```
Met Ala Leu Arg His Leu Ala Leu Leu Ala Gly Leu Leu Val Gly Val
  1               5                  10                  15

Ala Ser Lys Ser Met Glu Asn Thr Ala Gln Leu Pro Glu Cys Cys Val
                 20                  25                  30

Asp Val Val Gly Val Asn Ala Ser Cys Pro Gly Ala Ser Leu Cys Gly
             35                  40                  45

Pro Gly Cys Tyr Arg Arg Trp Asn Ala Asp Gly Ser Ala Ser Cys Val
         50                  55                  60

Arg Cys Gly Asn Gly Thr Leu Pro Ala Tyr Asn Gly Ser Glu Cys Arg
 65                  70                  75                  80

Ser Phe Ala Gly Pro Gly Ala Pro Phe Pro Met Asn Arg Ser Ser Gly
                 85                  90                  95

Thr Pro Gly Arg Pro His Pro Gly Ala Pro Arg Val Ala Ala Ser Leu
            100                 105                 110

Phe Leu Gly Thr Phe Phe Ile Ser Ser Gly Leu Ile Leu Ser Val Ala
        115                 120                 125

Gly Phe Phe Tyr Leu Lys Arg Ser Ser Lys Leu Pro Arg Ala Cys Tyr
    130                 135                 140

Arg Arg Asn Lys Gly Pro Ala Pro Ala Gly Ser Leu Pro Gly Arg Trp
145                 150                 155                 160

Ser Ser Gln Gln Phe Gly Pro Gln Ala Pro Ala Leu Gln Pro Gly Glu
                165                 170                 175

Ala Val Ser Asn Pro His His Pro Gly
            180                 185
```

<210> SEQ ID NO 33
<211> LENGTH: 594
<212> TYPE: DNA
<213> ORGANISM: Artificial Sequence
<220> FEATURE:
<223> OTHER INFORMATION: computationally derived degenerate sequence
<220> FEATURE:
<221> NAME/KEY: misc_feature
<222> LOCATION: (1)...(594)

-continued

```
<223> OTHER INFORMATION: N = A,T,C or G; W = A or T; S = G or C; Y = T
      or C; M = A or C; R = G or A; H = A or C or T

<400> SEQUENCE: 33
atggcnytnm gncayytngc nytnytngcn ggnytnytng tnggngtngc nwsnaarwsn     60
atggaraaya cngcncaryt nccngartgy tgygtngayg tngtnggngt naaygcnwsn    120
tgyccnggng cnwsnytntg yggnccnggn tgytaymgnm gntggaaygc ngayggnwsn    180
gcnwsntgyg tnmgntgygg naayggnacn ytnccngcnt ayaayggnws ngartgymgn    240
wsnttygcng gnccnggngc nccnttyccn atgaaymgnw snwsnggnac nccnggnmgn    300
ccncayccng gngcnccnmg ngtngcngcn wsnytnttyy tnggnacntt yttyathwsn    360
wsnggnytna thytnwsngt ngcnggntty ttytayytna armgnwsnws naarytnccn    420
mgngcntgyt aymgnmgnaa yaargcnccn gcnytncarc cnggngargc ngcngcnatg    480
athccnccnc cncarwsnws ngtnmgnaar ccnmgntayg tnmgnmgnga rmgnccnytn    540
gaymgngcna cngayccngc ngcnttyccn ggngargcnm gnathwsnaa ygtn          594

<210> SEQ ID NO 34
<211> LENGTH: 45
<212> TYPE: PRT
<213> ORGANISM: homo sapiens
<220> FEATURE:
<221> NAME/KEY: DOMAIN
<222> LOCATION: (1)...(45)
<223> OTHER INFORMATION: cysteine rich

<400> SEQUENCE: 34

Ala Ser Cys Pro Gly Ala Ser Leu Cys Gly Pro Gly Cys Tyr Arg Arg
 1               5                  10                  15

Trp Asn Ala Asp Gly Ser Ala Ser Cys Val Arg Cys Gly Asn Gly Thr
            20                  25                  30

Leu Pro Ala Tyr Asn Gly Ser Glu Cys Arg Ser Phe Ala
        35                  40                  45

<210> SEQ ID NO 35
<211> LENGTH: 45
<212> TYPE: PRT
<213> ORGANISM: mus musculus
<220> FEATURE:
<221> NAME/KEY: DOMAIN
<222> LOCATION: (1)...(45)
<223> OTHER INFORMATION: cysteine rich

<400> SEQUENCE: 35

Ala Thr Cys Leu Gly Thr Gly Leu Cys Gly Pro Gly Cys Tyr Arg His
 1               5                  10                  15

Trp Asn Ala Asp Gly Ser Ala Ser Cys Val Arg Cys Trp Asn Gly Thr
            20                  25                  30

Leu Pro Thr Tyr Asn Asp Ser Glu Cys Arg Ile Leu Thr
        35                  40                  45

<210> SEQ ID NO 36
<211> LENGTH: 6
<212> TYPE: PRT
<213> ORGANISM: Artificial Sequence
<220> FEATURE:
<223> OTHER INFORMATION: protein tag

<400> SEQUENCE: 36

Glu Tyr Met Pro Met Glu
 1               5
```

<210> SEQ ID NO 37
<211> LENGTH: 693
<212> TYPE: DNA
<213> ORGANISM: Artificial Sequence
<220> FEATURE:
<223> OTHER INFORMATION: Fc4 solublizing domain

<400> SEQUENCE: 37

```
agatcttcag acaaaactca cacatgccca ccgtgcccag cacctgaagc cgagggggca    60
ccgtcagtct tcctcttccc cccaaaaccc aaggacaccc tcatgatctc ccggacccct   120
gaggtcacat gcgtggtggt ggacgtgagc cacgaagacc ctgaggtcaa gttcaactgg   180
tacgtggacg gcgtggaggt gcataatgcc aagacaaagc cgcgggagga gcagtacaac   240
agcacgtacc gtgtggtcag cgtcctcacc gtcctgcacc aggactggct gaatggcaag   300
gagtacaagt gcaaggtctc caacaaagcc ctcccatcct ccatcgagaa aaccatctcc   360
aaagccaaag gcagccccg agaaccacag gtgtacaccc tgcccccatc ccgggatgag   420
ctgaccaaga accaggtcag cctgacctgc ctggtcaaag gcttctatcc cagcgacatc   480
gccgtggagt gggagagcaa tgggcagccg gagaacaact acaagaccac gcctcccgtg   540
ctggactccg acggctcctt cttcctctac agcaagctca ccgtggacaa gagcaggtgg   600
cagcagggga acgtcttctc atgctccgtg atgcatgagg ctctgcacaa ccactacacg   660
cagaagagcc tctccctgtc tccgggtaaa taa                                693
```

<210> SEQ ID NO 38
<211> LENGTH: 657
<212> TYPE: DNA
<213> ORGANISM: mus musculus

<400> SEQUENCE: 38

```
ggtggcatct ctcttccaat tggtctgatt gttggagtga catcactggg tctgctgatg    60
ttaggactgg tgaactgcat catcctggtg cagaggaaaa agaagccctc ctgcctacaa   120
agagatgcca aggtgcctca tgtgcctgat gagaaatccc aggatgcagt aggccttgag   180
cagcagcacc tgttgaccac agcacccagt tccagcagca gctccctaga gagctcagcc   240
agcgctgggg accgaagggc gcccctgggg gccatcccc aagcaagagt catggcggag   300
gcccaagggt tcaggaggc ccgtgccagc tccaggattt cagattcttc ccacggaagc   360
cacgggaccc acgtcaacgt cacctgcatc gtgaacgtct gtagcagctc tgaccacagt   420
tctcagtgct cttcccaagc cagcgccaca gtgggagacc cagatgccaa gccctcagcg   480
tccccaaagg atgagcaggt ccccttctct caggaggagt gtccgtctca gtccccgtgt   540
gagactacag agacactgca gagccatgag aagcccttgc cccttggtgt gccggatatg   600
ggcatgaagc ccagccaagc tggctggttt gatcagattg cagtcaaagt ggcctga      657
```

<210> SEQ ID NO 39
<211> LENGTH: 824
<212> TYPE: DNA
<213> ORGANISM: Artificial Sequence
<220> FEATURE:
<223> OTHER INFORMATION: cDNA of reporter gene

<400> SEQUENCE: 39

```
ggtaccgaat tgtacgcgta tggggacttc ccatatcaat cagggacttt ccgctgggga    60
ctttccggtc tgactcatgc ttctgactca tgcttgggtg acatcatctc gactagtcgt   120
```

-continued

| | |
|---|---|
| accttcccgt aaatccctcc ccttcccgga attacacacg cgtatttccc agaaaaggaa | 180 |
| ctgtagattt ctaggaattc aatccttggc cacgcgttta caccggaagt tttccatatt | 240 |
| aggaattcct tccggtttcc tttctcgagg ccaccgtggt tgagcccgac actcattcat | 300 |
| aaaacgcttg ttataaaagc agtggctgcg gcgccttcgt actccaaccg catctgcagc | 360 |
| gagcaactga aagccaagg atccaggctg aattcatggg tctcaacccc cagctagttg | 420 |
| tcatcctgct cttctttctc gaatgtacca ggagccatat ccacggatgc gacaaaaatc | 480 |
| acttgagaga gatcatcggc attttgaacg aggtcacagg agaagggacg ccatgcacgg | 540 |
| agatggatgt gccaaacgtc ctcacagcaa cgaagaacac cacagagagt gagctcgtct | 600 |
| gtagggcttc caaggtgctt cgcatatttt atttaaaaca tgggaaaact ccatgcttga | 660 |
| agaagaactc tagtgttctc atggagctgc agagactctt tcgggctttt cgatgcctgg | 720 |
| attcatcgat aagctgcacc atgaatgagt ccaagtccac atcactgaaa gacttcctgg | 780 |
| aaagcctaaa gagcatcatg caaatggatt actcgtagtc taga | 824 |

<210> SEQ ID NO 40
<211> LENGTH: 16
<212> TYPE: DNA
<213> ORGANISM: homo sapiens

<400> SEQUENCE: 40
ctggcgaagc cgctgc                                                              16

<210> SEQ ID NO 41
<211> LENGTH: 20
<212> TYPE: DNA
<213> ORGANISM: homo sapiens

<400> SEQUENCE: 41
gatccgtggc cctgtccagg                                                          20

<210> SEQ ID NO 42
<211> LENGTH: 29
<212> TYPE: DNA
<213> ORGANISM: homo sapiens

<400> SEQUENCE: 42
agaagaaaca aagctccggc cctgcagcc                                                29

<210> SEQ ID NO 43
<211> LENGTH: 24
<212> TYPE: DNA
<213> ORGANISM: homo sapiens

<400> SEQUENCE: 43
cccagcacca ctgaagcgat ggct                                                     24

<210> SEQ ID NO 44
<211> LENGTH: 19
<212> TYPE: DNA
<213> ORGANISM: homo sapiens

<400> SEQUENCE: 44
caaagggccg gcccccgca                                                           19

<210> SEQ ID NO 45
<211> LENGTH: 24
<212> TYPE: DNA
<213> ORGANISM: homo sapiens

```
<400> SEQUENCE: 45
gaaaaggaga gaaaggcaga gtga                                              24

<210> SEQ ID NO 46
<211> LENGTH: 18
<212> TYPE: DNA
<213> ORGANISM: homo sapiens

<400> SEQUENCE: 46
agtcctcagt acggaagc                                                     18

<210> SEQ ID NO 47
<211> LENGTH: 23
<212> TYPE: DNA
<213> ORGANISM: homo sapiens

<400> SEQUENCE: 47
ccacccgagg acagacgcag ccg                                               23

<210> SEQ ID NO 48
<211> LENGTH: 23
<212> TYPE: DNA
<213> ORGANISM: homo sapiens

<400> SEQUENCE: 48
ccacccgagg acagacgcag ccg                                               23

<210> SEQ ID NO 49
<211> LENGTH: 22
<212> TYPE: DNA
<213> ORGANISM: homo sapiens

<400> SEQUENCE: 49
ctcatttgga attttgccga tt                                                22

<210> SEQ ID NO 50
<211> LENGTH: 22
<212> TYPE: DNA
<213> ORGANISM: homo sapiens

<400> SEQUENCE: 50
ccgagtgaag atccccttttt ta                                               22

<210> SEQ ID NO 51
<211> LENGTH: 26
<212> TYPE: DNA
<213> ORGANISM: homo sapiens

<400> SEQUENCE: 51
tgaacagtca ccgacgagag tgctgg                                            26
```

ZTNFR14, A TUMOR NECROSIS FACTOR RECEPTOR

REFERENCE TO RELATED APPLICATIONS

This application claims benefit of U.S. Provisional Application Ser. No. 60/511,698, filed on Oct. 16, 2003, and is incorporated by reference herein.

BACKGROUND OF THE INVENTION

The tumor necrosis factor receptor (TNFR) family consists of a number of integral membrane glycoprotein receptors many of which, in conjunction with their respective ligands, are believed to regulate interactions between different hematopoietic cell lineages (Smith et al., *The TNF Receptor Superfamily of Cellular and Viral Proteins: Activation, Costimulation and Death*, 76:959-62, 1994; Cosman, *Stem Cells* 12:440-55, 1994). However, systemic expression of several members of this family suggest that these receptors may also play more general roles in organism development, homeostatsis, tumorigenesis, transplant rejection, septic shock, viral replication, and bone resorption. (Aggarwal, *Nat. Rev. Immunol.* 3:745-56, 2003).

The TNF receptor family is composed primarily of type I integral membrane glycoproteins which exhibit sequence homology, particularly with respect to cysteine-rich repeats in their extracellular domains. The TNF receptor family includes over 29 members (reviewed in Bodmer et al. *TRENDS in Biochem. Sci.* 27:19-26, 2002). A subgroup of this family whose members have particular structural similarities includes BAFF-R (Thompson et al., *Science* 293: 2108-2111, 2001), BCMA (Gross et al., *Nature* 404, 995-9, 2000), TWEAKR (Wiley et al., *Immunity* 15: 837-46, 2001), EDAR (Monreal et al., *Nat. Gen.* 22:315-6, 1999), XEDAR (Yan et al., 290:523-7), TACI (von Bülow and Bram, *Science* 278:138-141, 1997), and MK61 (Theill et al., WO0220762, 14 Mar. 2002), This group of TNFRs are distinguished by having two or fewer cysteine-rich domains along with a more variable cysteine-rich pattern than what is commonly seen.

In general, members of the TNF receptor family are characterized by a multi-domain structure comprising an extracellular region, a transmembrane domain, a linker region between the extracellular ligand-binding region and the transmembrane domain, and a cytoplasmic domain. In several members of this family (TNFR 1, Fas, DR3, DR4, DR5, DR6, NGFR and EDAR) this cytoplasmic domain contains a death domain associated with apoptosis. These members of the TNFR family, as well as others that do not include death domains such as TACI and BCMA, have been shown to bind one or more of the six tumor necrosis factor receptor-associated factors (TRAF1-6). These factors bind to the intracellular domain of the receptor at a short consensus sequence and act to couple the receptor to internal cell signaling pathways.

The extracellular ligand-binding region is characterized by the presence of one to six cysteine-rich motifs each containing about six cysteines and approximately 40 amino acids, although variation in the size and number of these motifs occurs among members of this family. The cysteine-rich regions provide the motif for binding to shared structures in the ligands. The highest degree of homology among the TNFR family members is within this extracellular cysteine-rich region. Among human TNFRs the average homology is in the range of 25% to 30%. Between the last cysteine-rich repeat and the transmembrane domain is a small spacer region of between 8 to 70 amino acid residues. Cell surface TNF receptors are anchored in the cell membrane by a transmembrane domain characterized by a sequence of hydrophobic amino acid residues. On the opposite end of the protein from the extracellular ligand-binding region and separated from it by the transmembrane domain is the cytoplasmic domain. The cytoplasmic domains of TNFR family members are small, from 46 to 221 amino acid residues, which suggests possible differences in the signaling mechanisms among family members. In the TNF receptor for example, activation is triggered by the aggregation of cytoplasmic domains of three receptors when their corresponding extracellular domains bind to trimeric ligand, which may be a common method of activation for the receptor family.

One member of the TNF receptor family, osteoprotegerin (Simonet et al., ibid.), is unique in that it is a secreted protein. Soluble forms of other TNF receptors have been described for TNFR-I, TNFR-II, low-affinity NGFR, FAS, CD27, CD30, CD40 and 4-1BB, but these were generated either by cleaving from the cell membrane or secreted by alternatively spliced mRNA. OPG inhibits osteoclast maturation and it is thought that it might serve to regulate bone density by modulating osteoclast differentiation from hematopoietic precursors. OPG provided protection from normal osteoclast remodeling and ovariectomy-associated bone loss.

The X-ray crystallographic structures have been resolved for human TNF (Jones et al., *Nature* 338:225-28, 1989), LT-a (Eck et al., *J. Biol. Chem.* 267:2119-122, 1992) and the LT-a/TNFR complex (Banner et al., *Cell* 73:431-45, 1993). This complex features three receptor molecules bound symmetrically to one LT-a trimer. A model of trimeric ligand binding through receptor oligomerization has been proposed to initiate signal transduction pathways. The identification of biological activity of several TNF members has been facilitated through use of monoclonal antibodies specific for the corresponding receptor. These monoclonal antibodies tend to be stimulatory when immobilized and antagonistic in soluble form. This is further evidence that receptor crosslinking is a prerequisite for signal transduction in this receptor family. Importantly, the use of receptor-specific monoclonal antibodies or soluble receptors in the form of multimeric Ig fusion proteins has been useful in determining biological function in vitro and in vivo for several family members. Soluble receptor-Ig fusion proteins have been used successfully in the cloning of the cell surface ligands corresponding to the CD40, CD30, CD27, 4-1BB and Fas receptors.

Ligands for these receptors have been identified, and with one exception (NGF) belong to the TNF ligand family. The members of the TNF ligand family share approximately 20% sequence identity in the extracellular ligand-binding regions, and exist mainly as type II membrane glycoproteins, biologically active as trimeric or multimeric complexes. Although most ligands are synthesized as membrane-bound proteins, soluble forms can be generated by limited proteolysis. For some receptors, solublization is necessary for activity, while for others, their activity is inhibited upon cleavage.

SUMMARY OF THE INVENTION

Within one aspect, the invention provides an isolated polypeptide comprising residues 18 to 108 of SEQ ID NO:2. Within another embodiment, the invention provides an isolated polypeptide comprising residues 1 to 108 of SEQ ID NO:2. Another aspect of the invention is an isolated polypeptide comprising residues 18 to 131 of SEQ ID NO:2, as well as an isolated polypeptide comprising residues 1 to 131 of SEQ ID NO:2. A further aspect of the present invention is an isolated polypeptide comprising residues 18 to 198 of SEQ ID NO:2.

Within another aspect, the invention provides an isolated polypeptide selected from the group consisting of: a) polypeptides comprising residues 1 to 198 of SEQ ID NO:2; b) polypeptides comprising residues 1 to 308 of SEQ ID NO: 30; and c) polypeptides comprising residues 1 to 185 of SEQ ID NO:32.

Within another aspect, is provided an isolated polypeptide comprising residues 18 to X, wherein X is an integer between 80 and 108.

Within another aspect, the invention provides an expression vector comprising the following operably linked elements: a) a transcription promoter; b) a DNA segment wherein the DNA segment is a polynucleotide molecule encoding the polypeptide molecule of comprising residues 18 to 108 of SEQ ID NO:2; and a transcription terminator. Within an embodiment, the DNA segment contains an affinity tag. Within another embodiment, the invention provides a cultured cell into which has been introduced the expression vector, wherein said cell expresses the polypeptide encoded by the DNA segment. Within another embodiment, the invention provides a method of producing a polypeptide comprising culturing the cell, whereby said cell expresses the polypeptide encoded by the DNA segment; and recovering the polypeptide. Within another embodiment, is provided the polypeptide produced by the cell.

The invention also provides a method for detecting a genetic abnormality in a patient, including obtaining a genetic sample from a patient; producing a first reaction product by incubating the genetic sample with a polynucleotide comprising at least 14 contiguous nucleotides of SEQ ID NO:1 or the complement of SEQ ID NO:1, under conditions wherein said polynucleotide will hybridize to complementary polynucleotide sequence; visualizing the first reaction product; and comparing the first reaction product to a control reaction product from a wild type patient, wherein a difference between said first reaction product and said control reaction product is indicative of a genetic abnormality in the patient.

A further method of the present invention is for detecting a cancer in a patient obtaining a tissue or biological sample from a patient incubating the tissue or biological sample with an antibody that specifically binds a polypeptide selected from the group consisting of: residues 18 to X of SEQ ID NO:2, wherein x is an integer from 80 to 108, a polypeptide comprising residues 18 to 108 of SEQ ID NO:2, a polypeptide comprising residues 30 to 80 of SEQ ID NO:2, a polypeptide comprising residues 50 to 80 of SEQ ID NO:2, and a polypeptide comprising residues 131 to 198 of SEQ ID NO:2 under conditions wherein the antibody binds to its complementary polypeptide in the tissue or biological sample visualizing the antibody bound in the tissue or biological sample; and comparing levels of antibody bound in the tissue or biological sample from the patient to a normal control tissue or biological sample, where an increase or decrease in the level of antibody bound to the patient tissue or biological sample relative to the normal control tissue or biological sample is indicative of a cancer in the patient.

A second method for detecting a cancer in a patient is also provided involving obtaining a tissue or biological sample from a patient, labeling a polynucleotide comprising at least 14 contiguous nucleotides of SEQ ID NO:1 or the complement of SEQ ID NO:1, incubating the tissue or biological sample with under conditions wherein the polynucleotide will hybridize to complementary polynucleotide sequence, visualizing the labeled polynucleotide in the tissue or biological sample; and comparing the level of labeled polynucleotide hybridization in the tissue or biological sample from the patient to a normal control tissue or biological sample, where an increase or decrease in the labeled polynucleotide hybridization to the patient tissue or biological sample relative to the normal control tissue or biological sample is indicative of a cancer in the patient.

A further aspect of the present invention is a method of killing cancer cells comprising, obtaining ex vivo a tissue or biological sample containing cancer cells from a patient, or identifying cancer cells in vivo; producing a polypeptide by recombinant means, formulating the polypeptide in a pharmaceutically acceptable vehicle; and administering to the patient or exposing the cancer cells to the polypeptide; wherein the polypeptide kills the cells. This method can also be done where the polypeptide is conjugated to a toxin.

Within another aspect, the invention provides a method of detecting neuroblastoma, melanoma, or lymphoma, particularly T-cell lymphoma, comprising, contacting said neuroblastoma, melanoma, or lymphoma with a polynucleotide consisting of the polynucleotide sequence as shown in SEQ ID NOS: 1, 3, 29 or 31, wherein the polynucleotide hybridizes to the mRNA in the neuroblastoma, melanoma, or lymphoma. Within an embodiment the polynucleotide is selected from the group consisting of: a polynucleotide consisting of at least 16 contiguous nucleotides as shown in SEQ ID NO:1; a polynucleotide consisting of from 17 to 25 contiguous nucleotides as shown in SEQ ID NO:1; a polynucleotide consisting of 40 contiguous nucleotides as shown in SEQ ID NO:1; a polynucleotide consisting of 60 contiguous nucleotides as shown in SEQ ID NO:1; a polynucleotide consisting of at least 16 contiguous nucleotides as shown in SEQ ID NO:29; a polynucleotide consisting of from 17 to 25 contiguous nucleotides as shown in SEQ ID NO:29; a polynucleotide consisting of 40 contiguous nucleotides as shown in SEQ ID NO:29; a polynucleotide consisting of 60 contiguous nucleotides as shown in SEQ ID NO:29; a polynucleotide consisting of at least 16 contiguous nucleotides as shown in SEQ ID NO:31; a polynucleotide consisting of from 17 to 25 contiguous nucleotides as shown in SEQ ID NO:31; a polynucleotide consisting of 40 contiguous nucleotides as shown in SEQ ID NO:31; a polynucleotide consisting of 60 contiguous nucleotides as shown in SEQ ID NO:31.

Within another embodiment is method of detecting cancerous cells, particularly neuroblastoma, melanoma, or lymphoma with an antibody to the polypeptide comprising residues 18 to X wherein x is an integer from 80 to 108. Within an embodiment, the antibody is generated to a polypeptide selected from the group consisting of: a polypeptide comprising residues 18 to 108 of SEQ ID NO:2; a polypeptide comprising residues 30 to 80 of SEQ ID NO:2; a polypeptide comprising residues 50 to 80 of SEQ ID NO:2; and a polypeptide comprising residues 131 to 198 of SEQ ID NO:2.

Within another aspect of the invention, is provided a method of inhibiting the quantity of lung carcinoma, breast carcinoma, melanoma, osteosarcoma, or lymphoma cells expressing a polypeptide selected from the group consisting of: an isolated polypeptide as shown in SEQ ID NO:2; an isolated polypeptide as shown in SEQ ID NO:29; and an isolated polypeptide as shown in SEQ ID NO:3; comprising administering to the cells an isolated polypeptide wherein the isolated polypeptide consists of residues 18 to X of SEQ ID NO:2, wherein X is an integer between 80 and 108.

Another aspect of the present invention is a method of detection and, additionally, a method of separation of activated immune cells from those that are in the resting state. These methods involve the detection of expression of ztnfr14, either at the RNA or protein level, then the separation of those cells expressing high levels from those with lower levels. Such a separation results in an immune cell population that is enriched for activated cells. Immune cells that are preferred embodiments for this method include B cells, NK cells, and certain types of T cells.

Within another aspect, the invention provides an expression vector comprising the following operably linked elements: a transcription promoter; a DNA segment wherein the DNA segment is a polynucleotide molecule encoding the polypeptide molecule of claim 1; and a transcription terminator. Within an embodiment, the expression vector according contains an affinity tag. Within another embodiment, is provided a cultured cell into which has been introduced the expression vector according, and the cell expresses the polypeptide encoded by the DNA segment. Within a further embodiment, the invention provides a method of producing a polypeptide comprising culturing the cell, whereby said cell expresses the polypeptide encoded by the DNA segment; and recovering the polypeptide.

Within another aspect, the invention provides a method of producing an antibody comprising the following steps in order: inoculating an animal with a polypeptide selected from the group consisting of: a polypeptide molecule consisting of a polypeptide comprising residues 18 to 108 of SEQ ID NO:2; a polypeptide comprising residues 30 to 80 of SEQ ID NO:2; a polypeptide comprising residues 50 to 80 of SEQ ID NO:2; or a polypeptide comprising residues 131 to 198 of SEQ ID NO: 2, wherein the polypeptide elicits an immune response in the animal to produce the antibody; and isolating the antibody from the animal. Within an embodiment, the antibody produced by the method binds to a residues 1 to 269 of SEQ ID NO:2. Within an embodiment, the antibody is a monoclonal antibody. Within an embodiment, the antibody specifically binds to the polypeptide.

Within another aspect, the invention provides a method of producing an antibody comprising the following steps in order: inoculating an animal with an epitope bearing portion of a polypeptide wherein the epitope bearing portion is selected from the group consisting of: a polypeptide molecule consisting of a polypeptide comprising residues 18 to 108 of SEQ ID NO:2; a polypeptide comprising residues 30 to 80 of SEQ ID NO:2; a polypeptide comprising residues 50 to 80 of SEQ ID NO:2; or a polypeptide comprising residues 131 to 198 of SEQ ID NO: 2 wherein the polypeptide elicits an immune response in the animal to produce the antibody; and isolating the antibody from the animal. Within an embodiment, the antibody produced by the method binds to a residues 1 to 269 of SEQ ID NO:2. Within an embodiment, the antibody is a monoclonal antibody. Within an embodiment, the antibody specifically binds to the polypeptide.

Within another aspect, the invention provides a method of forming a reversible peptide-receptor complex comprising; providing a receptor wherein the receptor comprises residues 18 to 108 of SEQ ID NO:2; and contacting the receptor with a peptide; wherein the receptor binds the peptide.

Within another aspect, the invention provides an isolated polypeptide molecule selected from the groups consisting of: a polypeptide molecule comprising residues 18 to 198 of SEQ ID NO:2; a polypeptide molecule comprising residues 18 to 308 of SEQ ID NO:29; and a polypeptide comprising residues 1 to 185 of SEQ ID NO:31. Within an embodiment, the invention provides a polynucleotide encoding the isolated polypeptide.

Within another aspect, the invention provides a method of detecting carcinoma in neural tissue, skin tissue, or cells of the hematopoetic lineage comprising, contacting said carcinoma with an antibody to the polypeptide as shown in SEQ ID NO:2. Within an embodiment, the antibody is generated to a polypeptide selected from the group consisting of: 18 to 108 of SEQ ID NO:2; a polypeptide comprising residues 30 to 80 of SEQ ID NO:2; a polypeptide comprising residues 50 to 80 of SEQ ID NO:2; or a polypeptide comprising residues 131 to 198 of SEQ ID NO: 2.

Within another aspect, the invention provides a method of modulating receptor activation in cells comprising administering to the cells an isolated polypeptide, wherein the isolated polypeptide comprises an amino acid as shown in SEQ ID NO:2 from residue 18 to residue X, wherein X is an integer from 80 to 108. Within an embodiment, the cells express a polypeptide sequence comprising the amino acid sequence of SEQ ID NO:1. Within another embodiment, the isolated polypeptide consists of an amino acid as shown in SEQ ID NO:2 from residue 1 to residue X, wherein X is an integer from 80 to 108.

Within another aspect of the invention is provided a method of modulating proliferation of carcinoma cells comprising administering to the cells an isolated polypeptide wherein the isolated polypeptide comprises an amino acid as shown in SEQ ID NO:2 from residue 18 to X, wherein X is an integer from 80 to 108. Within an embodiment, the carcinoma cells are neuroblastoma, melanoma, or lymphoma cells.

These and other aspects of the invention will become evident upon reference to the following detailed description of the invention and attached drawings.

DESCRIPTION OF THE FIGURES

FIG. 1 shows a comparison of the amino acid sequence of the human and mouse ztnfr14 (SEQ ID NOS:1 and 3, respectively) with related members of the TNFR family. The other listed sequences include: human and mouse ztnfr12 (BAFF-R, SEQ ID NOS: 5 and 7); human and mouse BCMA (SEQ ID NOS: 8 and 10); human and mouse TWEAKR (SEQ ID NOS: 11 and 13); human and mouse EDAR (SEQ ID NOS: 14 and 16); human XEDAR (SEQ ID NO:17); human and mouse TACI (SEQ ID NOS:19 and 21); and human and mouse MK61 (SEQ ID NOS:22 and 24).

FIG. 2 compares a section of the cysteine-rich domain of human and mouse ztnfr14 (SEQ ID NOS:34 and 35) to at least one cysteine-rich domain of each of the following receptors: human ztnfr12 (BAFF-R, SEQ ID NO: 6); human BCMA (SEQ ID NO:9); human TWEAKR (SEQ ID NO:12); human EDAR (SEQ ID NO:15); human XEDAR (SEQ ID NO:18); human TACI (SEQ ID NO:20); and human MK61 (SEQ ID NO:23).

FIG. 3 is a species comparison of the human (SEQ ID NO: 2), mouse (SEQ ID NO:4), rat (SEQ ID NO:25), cow (SEQ ID NO:26), chicken (SEQ ID NO: 27); and *xenopus* (SEQ ID NO:28) ztnfr14 sequences. The line indicated as "Cons" records the amino acids conserved between the species.

DETAILED DESCRIPTION OF THE INVENTION

Figure 4:
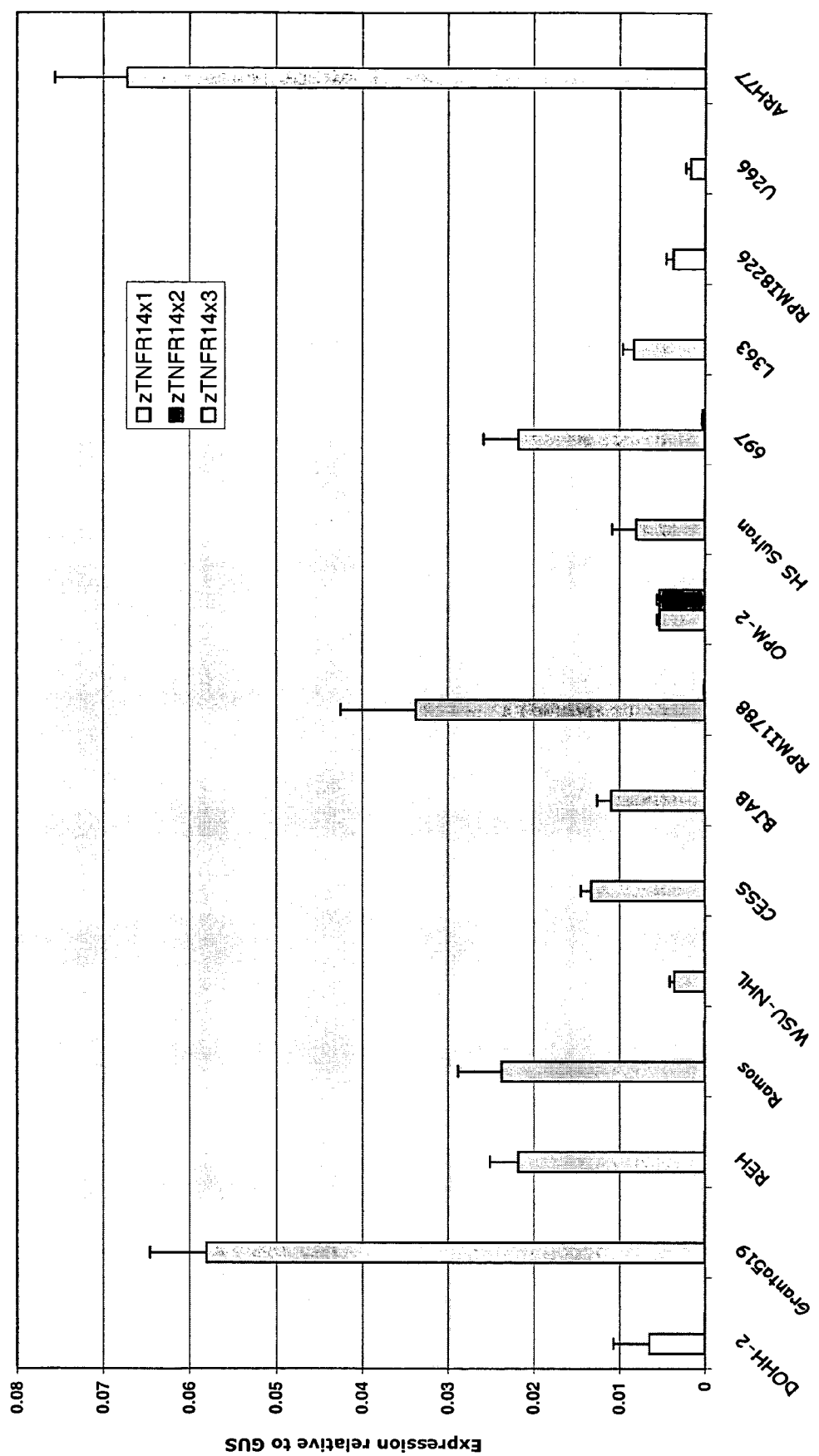
FIG. 4 is a graphic representation of the results of real time PCR analysis to access the expression of ztnrfl4×1, ztnfr14×2, and ztnfr14×3 in various unstimulated B cell lines.

Prior to setting forth the invention in detail, it may be helpful to the understanding thereof to define the following terms:

The term "affinity tag" is used herein to denote a polypeptide segment that can be attached to a second polypeptide to provide for purification of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985) (SEQ ID NO:7), substance P, Flag™ peptide (Hopp et al., *Biotechnology* 6:1204-1210, 1988), streptavidin binding peptide, maltose binding protein (Guan et al., *Gene* 67:21-30, 1987), cellulose binding protein, thioredoxin, ubiquitin, T7 polymerase, or other antigenic epitope or binding domain. See, in general, Ford et al., *Protein Expression and Purification* 2: 95-107, 1991. DNAs encoding affinity tags and other reagents are available from commercial suppliers (e.g., Pharmacia Biotech, Piscataway, N.J.; New England Biolabs, Beverly, Mass.; Eastman Kodak, New Haven, Conn.).

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "corresponding to", when applied to positions of amino acid residues in sequences, means corresponding positions in a plurality of sequences when the sequences are optimally aligned.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function(s) of the sequences are retained.

The term "ortholog" or "species homolog", denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

A "peptide-receptor complex" is formed when a peptide, or ligand, binds to a receptor resulting in a change in the properties of the receptor. This change can result in an initiation of sequences of reactions leading to a change in cellular function, or the inability of the receptor to bind additional peptides. The forming of a peptide-receptor complex can be reversible.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain or multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate. Many cell-surface receptors have naturally occurring, soluble counterparts that are produced by proteolysis or translated from alternatively spliced mRNAs. Receptor polypeptides are said to be substantially free of transmembrane and intracellular polypeptide segments when they lack sufficient portions of these segments to provide membrane anchoring or signal transduction, respectively.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequences (SEQ ID NOs:1) and corresponding polypeptide sequences (SEQ ID NOs:2) which have homology to members of the tumor necrosis factor receptor family. Novel receptor-encoding polynucleotides and polypeptides of the present invention were identified by the discovery of unannotated protein sequence with a transmembrane domain and a non-EGF (epidermal growth factor) cysteine-rich extracellular domain. Alignment of this cysteine-rich domain with other TNFRs revealed the homology of ztnfr14 to tumor necrosis factor receptor family members. An alignment of ztnfr14 with the mouse and human sequences of BAFF-R (ztnfr12), BCMA, TWEAKR, EDAR, XEDAR, TACI, and MK 61 is included as FIG. 1A-D.

Structurally, the TNF receptor family is characterized by an extracellular portion composed of several modules called, historically, "cysteine-rich pseudo-repeats." A prototypical family member has four of these pseudo-repeats, each about 29-43 residues long, one right after the other, although members of the family have been found with as few as one repeat. A typical pseudo-repeat has 6 cysteine residues. They are called pseudo-repeats because, although they appear to originate from a common ancestral module, they may not repeat exactly. The crystal structures of TNF receptors revealed that each pseudo-repeat commonly corresponds to one folding domain, and that generally, multiple copies of pseudo-repeats fold into the same tertiary structure, held together internally by disulfide bonds.

Sequence analysis of a deduced amino acid sequence of ztnfr14 indicates the presence of one extracellular, cysteine-rich pseudo-repeat (comprising generally residues 50 to 80 of SEQ ID NO:2, although cysteines present upstream of this sequence may also be involved in biological function). This type of pseudo-repeat structure is most closely related to those of the TACI/BCMA/BAFF-R/TWEAKR subgroup of TNF receptors. FIG. 2 is an alignment of the cysteine-rich domains for this group of receptors. As illustrated in the Figure, the cysteine-rich domain of ztnfr14 conserves four of the six cysteines typically seen in TNFR cysteine-rich domains (i.e., Cys51, Cys63, Cys66, and Cys79). Additionally, the Asp58 of ztnfr14 conserves the Asp26 of BAFF-R that has been recently shown to be required for activity (Gordon et al. *Biochemistry*, 42: 5977-5983, 2003). Although there are typically twelve residues between the "cysteine 1-2" pair, in both XEDAR and ztnfr14, there are eleven. Additional other cysteines in the general vicinity of this domain (Cys30, Cys31, and Cys41) may also be involved in disulfide bonds important to the protein structure of the ztnfr14 extracellular domain necessary for biological function, i.e., the binding of the ztnfr14 ligand.

The cysteine-rich pseudo-repeats are the known ligand binding sites for TNF ligands. Thus, the amino acid residues of ztnfr14 most likely to be involved in ligand binding are within residues 18 to 80 of SEQ ID NO:2.

The protein further comprises a signal sequence located at approximately residues 1 to 18 of SEQ ID NO:2. Cleavage of the mature protein is believed to be at the amino acids Lys-Ser-Met for the human sequence and Lys-Ser-Thr for the mouse (residues 19-21 of SEQ ID NO: 2 and SEQ ID NO: 4).

The protein also comprises a transmembrane domain (approximately residues 108 to 131 of SEQ ID NO:2) and a cytoplasmic, or signaling, domain (approximately residues 131 to 198 of SEQ ID NO:2). The mature membrane-bound ztnfr14 protein comprises amino acid residue 18 to 198 of SEQ ID NO:2. Those skilled in the art will recognize that these domain boundaries are approximate, and are based on alignments with known proteins and predictions of protein folding. These features indicate that the receptors encoded by the DNA sequences of SEQ ID NO:1 is a member of the TNF receptor family.

The linker region of ztnfr14 (residues 108 to 131 of SEQ ID NO:2) may not be necessary for binding of the receptor to the ligand. Thus, portions of it may be deleted from a construct for the soluble receptor. Therefore, a construct for a soluble receptor would be predicted range between residues 18 to 108 of SEQ ID NO:2 to as long as residues 1 to 131 of SEQ ID NO:2, although shorter molecules that exhibit the desired biological activity, i.e., binding of the ligand of ztnfr14, are also contemplated.

The polynucleotides of the present invention have been seen in EST libraries derived from many tissues, however they are more predominant than average in those of the stomach, uterus, and cancerous tissues. In particular, expression in tumors such as neuroblastomas, melanomas, and lymphomas are over represented. Expression in tumor cells is consistent with other members of the TNFR family that have been found to be associated with growth regulation, differentiation and tumorigenesis.

Chromosomal localization of the human ztnfr14 to genomic clone AL390719 on human chromosome 1 has been determined and localized to 1q36.3. Within 150 kb are two other TNFR genes: OX40 (TNRSF4) and GITR (TNRSF18), and four others (DR3, TNFR2, CD30, and 4-1BB) are within this genomic locus. Similarly, mouse ztnfr14 is located in a syntenic region on chromosome 4 (E region). As in the human genome, the same set of mouse TNFR genes is found in this location.

The present invention provides polynucleotide molecules, including DNA and RNA molecules, that encode the ztnfr14 polypeptides disclosed herein. Those skilled in the art will readily recognize that, in view of the degeneracy of the genetic code, considerable sequence variation is possible among these polynucleotide molecules. SEQ ID NO:33 is a degenerate DNA sequence that encompasses all DNAs that encode the ztnfr14 polypeptide of SEQ ID NO:2. Those skilled in the art will recognize that the degenerate sequence of SEQ ID NO: 33 also provides all RNA sequences encoding SEQ ID NO:2 by substituting U for T. Thus, ztnfr14 polypeptide-encoding polynucleotides comprising nucleotide 1 to nucleotide 1853 of SEQ ID NO:1 and their RNA equivalents are contemplated by the present invention. Table 1 sets forth the one-letter codes used within SEQ ID NO:33 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Nucleotide | Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:33 encompassing all possible codons for a given amino acid, are set forth in Table 2.

TABLE 2

| Amino Acid | One Letter Code | Codons | Degenerate Codon |
|---|---|---|---|
| Cys | C | TGC, TGT | TGY |
| Ser | S | AGC, AGT, TCA, TCC, TCG, TCT | WSN |
| Thr | T | ACA, ACC, ACG, ACT | CAN |
| Pro | P | CCA, CCC, CCG, CCT | CCN |
| Ala | A | GCA, GCC, GCG, GCT | GCN |
| Gly | G | GGA, GGC, GGG, GGT | GGN |
| Asn | N | AAC, AAT | AAY |
| Asp | D | GAC, GAT | GAY |
| Glu | E | GAA, GAG | GAR |
| Gln | Q | CAA, CAG | CAR |
| His | H | CAC, CAT | CAY |
| Arg | R | AGA, AGG, CGA, CGC, CGG, CGT | MGN |
| Lys | K | AAA, AAG | AAR |
| Met | M | ATG | ATG |
| Ile | I | ATA, ATC, ATT | ATH |
| Leu | L | CTA, CTC, CTG, CTT, TTA, TTG | YTN |
| Val | V | GTA, GTC, GTG, GTT | GTN |
| Phe | F | TTC, TTT | TTY |
| Tyr | Y | TAC, TAT | TAY |
| Trp | W | TGG | TGG |
| Ter | . | TAA, TAG, TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences of SEQ ID NO:2, 4, 30 or 32. Variant sequences can be readily tested for functionality as described herein.

The present invention further provides polynucleotide molecules, including DNA and RNA molecules, encoding ztnfr14 proteins. The polynucleotides of the present invention include the sense strand; the anti-sense strand; and the DNA as double-stranded, having both the sense and anti-sense strand annealed together by their respective hydrogen bonds. Representative DNA sequences encoding ztnfr14 proteins are set forth in SEQ ID NOs:1, 3, 29 and 31. DNA sequences encoding other ztnfr14 proteins can be readily generated by those of ordinary skill in the art based on the genetic code.

One of ordinary skill in the art will also appreciate that different species can exhibit "preferential codon usage." Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed in SEQ ID NO:33 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NOs:1, 3, 29, 31, or a sequence complementary thereto under stringent conditions. Polynucleotide hybridization is well known in the art and widely used for many applications, see for example, Sambrook et al., *Molecular Cloning: A Laboratory Manual, Second Edition*, Cold Spring Harbor, N.Y., 1989; Ausubel et al., eds., *Current Protocols in Molecular Biology*, John Wiley and Sons, Inc., NY, 1987; Berger and Kimmel, eds., Guide to Molecular Cloning Techniques, *Methods in Enzymology*, volume 152, 1987 and Wetmur, *Crit. Rev. Biochem. Mol. Biol.* 26:227-59, 1990. Polynucleotide hybridization exploits the ability of single stranded complementary sequences to form a double helix hybrid. Such hybrids include DNA-DNA, RNA-RNA and DNA-RNA.

As an illustration, a nucleic acid molecule encoding a variant ztnfr14 polypeptide can be hybridized with a nucleic acid molecule having the nucleotide sequence of SEQ ID NOs:1, 3, 29 or 31 (or their complements) at 65° C. overnight in ExpressHyb™ Hybridization Solution (CLONTECH Laboratories, Inc., Palo Alto, Calif.). One of skill in the art can devise variations of these hybridization conditions.

Following hybridization, the nucleic acid molecules can be washed to remove non-hybridized nucleic acid molecules under stringent conditions, or under highly stringent conditions. Typical stringent washing conditions include washing in a solution of 0.5×-2×SSC with 0.1% sodium dodecyl sulfate (SDS) at 55-65° C. That is, nucleic acid molecules encoding a variant ztnfr14 polypeptide hybridize with a nucleic acid molecule having the nucleotide sequences of SEQ ID NOs:1, 3, 29 or 31 (or their complements) under stringent washing conditions, in which the wash stringency is equivalent to 0.1×-2×SSC with 0.1% SDS at 55-65° C., including 0.1×SSC with 0.1% SDS at 55° C., or 2×SSC with 0.1% SDS at 65° C.

One of skill in the art can readily devise equivalent conditions, for example, by substituting SSPE for SSC in the wash solution.

The present invention also contemplates ztnfr14 variant nucleic acid molecules that can be identified using two criteria: a determination of the similarity between the encoded polypeptides with the amino acid sequences of SEQ ID NOs: 2, 4, 30 and 32 (as described below), and a hybridization assay, as described above. Such ztnfr14 variants include nucleic acid molecules that hybridize with a nucleic acid molecule having the nucleotide sequence of SEQ ID NOs:1, 3, 29 or 31 (or their complements) under stringent washing conditions, in which the wash stringency is equivalent to 0.1×-2×SSC with 0.1% SDS at 55-65° C., and (2) that encode a polypeptide having at least 80%, preferably 90%, more preferably, 95% or greater than 95% sequence identity to the amino acid sequence of SEQ ID NOs:2, 4, 30 or 32. Alternatively, ztnfr14 variants can be characterized as nucleic acid molecules (1) that hybridize with a nucleic acid molecule having the nucleotide sequence of SEQ ID NOs:1, 3, 29 or 31 (or their complements) under highly stringent washing conditions, in which the wash stringency is equivalent to 0.1×-0.2×SSC with 0.1% SDS at 50-65° C., and (2) that encode a polypeptide having at least 80%, preferably 90%, more preferably 95% or greater than 95% sequence identity to the amino acid sequence of SEQ ID NOs:2, 4, 30 or 32.

The highly conserved amino acids in the cysteine-rich pseudo-repeat domains of ztnfr14 can be used as a tool to identify new family members. For instance, reverse transcription-polymerase chain reaction (RT-PCR) can be used to amplify sequences encoding the conserved cysteine-rich domain from RNA obtained from a variety of tissue sources or cell lines. In particular, highly degenerate primers designed from the ztnfr14 sequences are useful for this purpose.

As previously noted, the isolated polynucleotides of the present invention include DNA and RNA. Methods for preparing DNA and RNA are well known in the art. In general, RNA is isolated from a tissue or cell that produces large amounts of ztnfr14 RNA. Such tissues and cells are identified by Northern blotting (Thomas, *Proc. Natl. Acad. Sci. USA* 77:5201, 1980) and in situ hybridization. Total RNA can be prepared using guanidine isothiocyante extraction followed by isolation by centrifugation in a CsCl gradient (Chirgwin et al., *Biochemistry* 18:52-94, 1979). Poly (A)$^+$ RNA is prepared from total RNA using the method of Aviv and Leder (*Proc. Natl. Acad. Sci. USA* 69:1408-12, 1972). Complementary DNA (cDNA) is prepared from poly(A)$^+$ RNA using known methods. In the alternative, genomic DNA can be isolated. Polynucleotides encoding ztnfr14 polypeptides are then identified and isolated by, for example, hybridization or PCR.

A full-length clone encoding ztnfr14 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to ztnfr14 or other specific binding partners.

The invention also provides isolated and purified ztnfr14 polynucleotide probes. Such polynucleotide probes can be RNA or DNA. DNA can be either cDNA or genomic DNA. Polynucleotide probes are single or double-stranded DNA or RNA, generally synthetic oligonucleotides, but may be generated from cloned cDNA or genomic sequences and will generally comprise at least 16 nucleotides, more often from 17 nucleotides to 25 or more nucleotides, sometimes 40 to 60 nucleotides, and in some instances a substantial portion, domain or even the entire ztnfr14 gene or cDNA. The synthetic oligonucleotides of the present invention have at least 80% identity to a representative ztnfr14 DNA sequence (SEQ ID NOs:1, 3, 29 or 31) or their complements. The invention also provides oligonucleotide probes or primers comprising at least 14 contiguous nucleotides of a polynucleotide of SEQ ID NOs:1, 3, 29 or 31 or a sequence complementary to SEQ ID NOs:1, 3, 29 or 31.

Preferred regions from which to construct probes include the 5' and/or 3' coding sequences, ligand binding regions, and signal sequences, and the like. Techniques for developing polynucleotide probes and hybridization techniques are known in the art, see for example, Ausubel et al., eds., *Current Protocols in Molecular Biology*, John Wiley and Sons, Inc., NY, 1991. For use as probes, the molecules can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art. Such probes can also be used in hybridizations to detect the presence or quantify the amount of ztnfr14 gene or mRNA transcript in a sample. ztnfr14 polynucleotide probes could be used to hybridize to DNA or RNA targets for diagnostic purposes, using such techniques such as fluorescent in situ hybridization (FISH) or immunohistochemistry. Polynucleotide probes can be used to identify genes encoding ztnfr14-like proteins. For example, ztnfr14 polynucleotides can be used as primers and/or templates in PCR reactions to identify other novel members of the TNFR family. Such probes can also be used to screen libraries for related sequences encoding novel tumor necrosis factor receptors. Such screening would be carried out under conditions of low stringency which would allow identification of sequences which are substantially homologous, but not requiring complete homology to the probe sequence. Such methods and conditions are well known in the art, see, for example, Sambrook et al., *Molecular Cloning: A Laboratory Manual*, Second Edition, Cold Spring Harbor, N.Y., 1989. Such low stringency conditions could include hybridization temperatures less than 42° C., formamide concentrations of less than 50% and moderate to low concentrations of salt. Libraries may be made of genomic DNA or cDNA. Polynucleotide probes are also useful for Southern, Northern, or slot blots, colony and plaque hybridization and in situ hybridization. Mixtures of different ztnfr14 polynucleotide probes can be prepared which would increase sensitivity or the detection of low copy number targets, in screening systems.

In addition, such polynucleotide probes could be used to hybridize to counterpart sequences on individual chromosomes. Chromosomal identification and/or mapping of the ztnfr14 gene could provide useful information about gene function and disease association. Many mapping techniques are available to one skilled in the art, for example, mapping somatic cell hybrids, and fluorescence in situ hybridization (FISH). A preferred method is radiation hybrid mapping. Radiation hybrid mapping is a somatic cell genetic technique developed for constructing high-resolution, contiguous maps of mammalian chromosomes (Cox et al., *Science* 250:245-50, 1990). Partial or full knowledge of a gene's sequence allows the designing of PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR based, chromosomal localizations and ordering of genes, sequence-tagged sites (STSs), and other non-polymorphic- and polymorphic markers within a region of interest. This includes establishing directly proportional physical distances between newly discovered genes of interest and previously mapped markers. The precise knowledge of a gene's position can be useful in a number of ways including: 1) determining if a sequence is part of an existing contig and obtaining additional surrounding genetic sequences in various forms such as YAC-, BAC- or cDNA clones, 2) providing a possible candidate gene for an inheritable disease which shows linkage to the same chromosomal region, and 3) for cross-referencing model organisms such as mouse which may be beneficial in helping to determine what function a particular gene might have.

ztnfr14 polynucleotide sequences disclosed herein can also be used as probes or primers to clone 5' non-coding regions of a ztnfr14 gene. In particular, the upstream region includes AP-1 binding sites. Due to the low binding specificity of transcription factors (TFs), predictions of individual binding sites have a high rate of false positives. Therefore, binding site predictions in isolation are of little or no practical use for the identification of binding sites with functional roles in vivo. However, predicted binding sites likely to have sequence-specific functions can be selected by means of a conservation-based filter: The biological observation that regulatory regions are often more strongly conserved between species than other non-coding regions can be quantified to reveal patterns of conservation which have been called phylogenetic footprints (Fickett and Wasserman, *Curr. Opin. Biotechnol.* 11: 19-24, 2000). In particular, human-rodent comparisons have proven a valuable resource for the identification of functional regulatory elements (Wasserman et al., *Nat. Genet.* 26: 225-228, 2000).

The search for individual transcription factor binding sites was performed with standard position weight matrices (Fickett, *Mol. Cell. Biol.* 16: 437-441, 1996) drawn from the TRANSFAC database (version 3.0, Wingender et al. *Nucelic Acids Res.* 28: 316-319, 2000) as well as several matrices that were assembled in-house using published TF binding sites. Based on published studies involving other sets of TFs, most natural binding sites sufficiently conserved between mouse and human can be expected to be detected in the used score range (Fickett, *Mol. Cell. Biol.* 16: 437-441, 1996; Wasserman et al., *J. Mol. Biol.* 278: 167-181, 1998).

A search for binding sites of a set of 34 TFs led to the identification of putative sites for NF-AT and AP-2 at the following positions relative to the transcription start site:

|        | human | mouse |
| ---    | ---   | ---   |
| NF-AT  | −191  | −157  |
| AP-2   | −107  | −82   |

The transcription factor AP-2 is implicated in differentiation and transformation. Putative binding sites have been found in promoters of TNFR family members (Yoo et al, *DNA Cell Biol.* 15: 377-385, 1996). Recently published findings suggest that AP-2 inhibits the growth of cells by inducing cell cycle arrest and apoptosis and that the use of AP-2 alpha should be explored as a therapeutic strategy either alone or in combination with chemotherapy (Wajapeyee et al., *J. Biol.*

Chem. epub Oct 9, 2003). Genes which are controlled by AP-2 may be over-expressed in cancer cells.

NF-AT plays an important role in the control of T cell activation and differentiation and likely also of the cell cycle and apoptosis of T lymphocytes (Serfling et al., *Biochim Biophys Acta.* 1498: 1-18, 2000).

As this gene region is expected to provide for specific expression in tissues of the stomach, uterus, and various cancers including neuroblastomas, melanomas, and lymphomas, promoter elements from a ztnfr14 gene including the NF-AP and AP-2 binding sites could thus be used to direct the tissue-specific expression of heterologous genes in, for example, transgenic animals or patients treated with gene therapy. Cloning of 5' flanking sequences also facilitates production of ztnfr14 proteins by "gene activation" as disclosed in U.S. Pat. No. 5,641,670. Briefly, expression of an endogenous ztnfr14 gene in a cell is altered by introducing into the ztnfr14 locus a DNA construct comprising at least a targeting sequence, a regulatory sequence, an exon, and an unpaired splice donor site. The targeting sequence is a ztnfr14 5' non-coding sequence that permits homologous recombination of the construct with the endogenous ztnfr14 locus, whereby the sequences within the construct become operably linked with the endogenous ztnfr14 coding sequence. In this way, an endogenous ztnfr14 promoter can be replaced or supplemented with other regulatory sequences to provide enhanced, tissue-specific, or otherwise regulated expression.

The polynucleotides of the present invention can also be synthesized using DNA synthesizers. Currently the method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. See Glick and Pasternak, *Molecular Biotechnology, Principles and Applications of Recombinant DNA*, (ASM Press, Washington, D.C. 1994); Itakura et al., *Annu. Rev. Biochem.* 53: 323-356 (1984) and Climie et al., *Proc. Natl. Acad. Sci. USA* 87:633-7, 1990.

The present invention further provides counterpart polypeptides and polynucleotides from other species (orthologs). These species include, but are not limited to mammalian, avian, amphibian, reptile, fish, insect and other vertebrate and invertebrate species. Of particular interest are ztnfr14 polypeptides from other mammalian species, including murine, porcine, ovine, bovine, canine, feline, equine, and other primate polypeptides. Orthologs of human ztnfr14 can be cloned using information and compositions provided by the present invention in combination with conventional cloning techniques. For example, a cDNA can be cloned using mRNA obtained from a tissue or cell type that expresses ztnfr14 as disclosed herein. Such tissue would include, for example, tissues of the stomach, uterus, neuroblastomas, melanomas, and lymphoma. Suitable sources of mRNA can be identified by probing Northern blots with probes designed from the sequences disclosed herein. A library is then prepared from mRNA of a positive tissue or cell line. A ztnfr14-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human ztnfr14 sequences disclosed herein. Within an additional method, the cDNA library can be used to transform or transfect host cells, and expression of the cDNA of interest can be detected with an antibody to ztnfr14 polypeptide. Similar techniques can also be applied to the isolation of genomic clones.

Those skilled in the art will recognize that the sequences disclosed in SEQ ID NO:1 represents a single allele of human ztnfr14 and that allelic variation and alternative splicing are expected to occur. The exon locations for the gene disclosed in SEQ ID NO: 1 are nucleotide positions 1-32, 33-145, 146-239, 240-315, 316-411, 412-477, 478-612, 613-638, 639-669, and 670-1834. In particular, two splice variants have been discovered: ztnfr14×2 has been identified and is disclosed in SEQ ID NOS: 29 and 30 and ztnfr14×3 has been identified and disclosed in SEQ ID NOS: 31 and 32. These variants differ from the base ztnfr14 sequence in that ztnfr14×2 adds an exon 9B, while ztnfrx3 adds an exon 7B, which contains a stop codon. Allelic variants of all three of these sequences can be cloned by probing cDNA or genomic libraries from different individuals according to standard procedures. Allelic variants of the DNA sequences shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the ztnfr14 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated ztnfr14 polypeptides that are substantially similar to the polypeptides of SEQ ID NOs:2, 4, 30 and 32 and their orthologs. Such polypeptides will more preferably be at least 90% identical, and more preferably 95% or more identical to SEQ ID NOs:2, 4, 30 and 32 and their orthologs. Percent sequence identity is determined by conventional methods. See, for example, Altschul et al., *Bull. Math. Bio.* 48: 603-16, 1986 and Henikoff and Henikoff, *Proc. Natl. Acad. Sci. USA* 89:10915-9, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant ztnfr14. The FASTA algorithm is described by Pearson and Lipman, Proc. Nat'l Acad. Sci. USA 85:2444 (1988), and by Pearson, Meth. Enzymol. 183:63 (1990).

Briefly, FASTA first characterizes sequence similarity by identifying regions shared by the query sequence (e.g., SEQ ID NOs:2, 4, 30 and 32) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of nucleic acid molecules using a ratio as disclosed above. For nucleotide sequence comparisons, the ktup value can range between one to six, preferably from four to six.

The present invention includes nucleic acid molecules that encode a polypeptide having one or more conservative amino acid changes, compared with the amino acid sequences of SEQ ID NOs:2, 4, 30 and 32. The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. As used herein, the language "conservative amino acid substitution" refers to a substitution represented by a BLOSUM62 value of greater than -1. For example, an amino acid substitution is conservative if the substitution is characterized by a BLOSUM62 value of 0, 1, 2, or 3. Preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Conservative amino acid changes in an ztnfr14 gene can be introduced by substituting nucleotides for the nucleotides recited in SEQ ID NOs:1, 3, 29 and 31. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8-10 to 8-22; and McPherson (ed.), Directed Mutagenesis: A Practical Approach (IRL Press 1991)). The ability of such variants to modulate cell-cell interactions, apoptosis, and inflammation can be determined using a standard method, such as the assay described herein. Alternatively, a variant ztnfr14 polypeptide can be identified by the ability to specifically bind anti-ztnfr14 antibodies.

Essential amino acids in the polypeptides of the present invention can be identified according to procedures known in the art, such as site-directed mutagenesis or alanine-scanning mutagenesis (Cunningham and Wells, Science 244: 1081-5, 1989; Bass et al., Proc. Natl. Acad. Sci. USA 88:4498-502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., J. Biol. Chem. 271:4699-708, 1996. Sites of receptor-ligand interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., *J. Mol. Biol.* 224:899-904, 1992; Wlodaver et al., *FEBS Lett.* 309:59-64, 1992. The identities of essential amino acids can also be inferred from analysis of homologies with related TNFR-like molecules.

Multiple amino acid substitutions can be made and tested using known methods of mutagenesis and screening, such as those disclosed by Reidhaar-Olson and Sauer (*Science* 241: 53-7, 1988) or Bowie and Sauer (*Proc. Natl. Acad. Sci. USA* 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed ztnfr14 DNA and polypeptide sequences can be generated through DNA shuffling, as disclosed by Stemmer, *Nature* 370:389-91, 1994, Stemmer, *Proc. Natl. Acad. Sci. USA* 91:10747-51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides (e.g., ligand binding activity) can be recovered from the host cells and rapidly sequenced using modern equipment. These methods allow the rapid determination of the importance of individual amino acid residues in a polypeptide of interest, and can be applied to polypeptides of unknown structure.

Regardless of the particular nucleotide sequence of a variant ztnfr14 gene, the gene encodes a polypeptide that is characterized by its cell-cell interaction activity, including but not limited to ztnfr14 ligand binding, tumorigensis, cell proliferation, or by the ability to bind specifically to an anti-ztnfr14 antibody. More specifically, variant ztnfr14 genes encode polypeptides which exhibit at least 50%, and preferably, greater than 70, 80, or 90%, of the activity of polypeptide encoded by the human ztnfr14 gene described herein.

Variant ztnfr14 polypeptides or substantially homologous ztnfr14 polypeptides are characterized as having one or more amino acid substitutions, deletions or additions. These changes are preferably of a minor nature, that is conservative amino acid substitutions and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20-25 residues, or an affinity tag. The present invention thus includes polypeptides of from 40 to 2000 amino acid residues that comprise a sequence that is at least 85%, preferably at least 90%, and more preferably 95% or more identical to the corresponding region of SEQ ID NOs:2, 4, 30 and 32. Polypeptides comprising affinity tags can further comprise a proteolytic cleavage site between the ztnfr14 polypeptide and the affinity tag. Preferred such sites include thrombin cleavage sites and factor Xa cleavage sites.

For any ztnfr14 polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise ztnfr14 variants based upon the nucleotide and amino acid sequences described herein. Accordingly, the present invention includes a computer-readable medium encoded with a data structure that provides at least one of the following sequences: SEQ ID NOs:1, 2, 3, 4, 29, 30, 31, or 32. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

The present invention further provides a variety of other polypeptide fusions and related multimeric proteins comprising one or more polypeptide fusions. For example, the cysteine-rich pseudo-repeat, or cytoplasmic polypeptide domains can be prepared as a fusion to a dimerizing protein, as disclosed in U.S. Pat. Nos. 5,155,027 and 5,567,584. Preferred dimerizing proteins in this regard include other cysteine-rich pseudo-repeat or cytoplasmic polypeptide domains, or polypeptides comprising other members of the TNF receptor family of proteins, such as, for example, APO4, TNFR-I, TNFR-II, and TNFR-III. Additionally, chimeras can be prepared with the extracellular portion of cytokine receptors. For example, the extracellular domain of erythropoietin can be fused to the linker, transmembrane, and cytoplasmic domain of ztnfr14 polypeptides to produce dimerization. These polypeptide domain fusions, can be expressed in genetically engineered cells to produce a variety of multimeric TNFR-like analogs.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between ztnfr14 of the present invention with the functionally equivalent domain(s) from another family member, such as APO4, TNFR-I, TNFR-II, and TNFR-III. Such domains include, but are not limited to, conserved motifs such as the cysteine-rich pseudo-repeat, transmembrane, and cytoplasmic domains. Such fusion proteins would be expected to have a biological functional profile that is the same or similar to polypeptides of the present invention or other known TNFR family proteins (e.g. APO4, TNFR-I, TNFR-II, and TNFR-III), depending on the fusion constructed. Moreover, such fusion proteins may exhibit other properties as disclosed herein.

Moreover, using methods described in the art, polypeptide fusions, or hybrid ztnfr14 proteins, are constructed using regions or domains of the inventive ztnfr14 in combination with those of other TNFR molecules. (e.g. APO4, TNFR-I, TNFR-II, and TNFR-III), or heterologous proteins (Sambrook et al., ibid., Altschul et al., ibid., Picard, *Cur. Opin. Biology*, 5:511-5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Auxiliary domains can be fused to ztnfr14 polypeptides to target them to specific cells, tissues, or macromolecules (e.g., tissues of the stomach, uterus, neuroblastoma, melanoma and lymphoma). For example, a protease domain could be targeted to a predetermined cell type by fusing it to the cysteine-rich pseudo-repeat domains (i.e., residues 30 to 108 of SEQ ID NO:2, or a portion thereof which has been shown to bind the ztnfr14 ligand). In this way, polypeptides, polypeptide fragments and proteins can be targeted for therapeutic or diagnostic purposes. Such the cysteine-rich pseudo-repeat domains, or portions thereof can be fused to two or more moieties, such as an affinity tag for purification and a targeting domains. Polypeptide fusions can also comprise one or more cleavage sites, particularly between domains. See, Tuan et al., *Connective Tissue Research* 34:1-9, 1996.

Polypeptide fusions of the present invention will generally contain not more than about 1,500 amino acid residues, preferably not more than about 1,200 residues, more preferably not more than about 1,000 residues, and will in many cases be considerably smaller. For example, residues of ztnfr14 polypeptide can be fused to *E. coli* b-galactosidase (1,021 residues; see Casadaban et al., *J. Bacteriol.* 143:971-980, 1980), a 10-residue spacer, and a 4-residue factor Xa cleavage site. In a second example, residues of ztnfr14 polypeptide can be fused to maltose binding protein (approximately 370 residues) or a 4-residue cleavage site.

ztnfr14 polypeptides or fragments thereof may also be prepared through chemical synthesis. ztnfr14 polypeptides may be monomers or multimers; glycosylated or non-glycosylated; pegylated or non-pegylated; and may or may not include an initial methionine amino acid residue.

The invention also provides soluble ztnfr14 receptors, used to form fusion or chimeric proteins with human Ig, as Glu-Glu tagged proteins, or FLAG™-tagged proteins. One such construct is comprises residues 30 to 108 of SEQ ID NO:2, fused to human Ig, another comprises residues 50 to 108 of SEQ ID NO:2 fused to human Ig. ztnfr14 or ztnfr14-Ig chimeric proteins are used, for example, to confirm ztnfr14 binds to its ligand, as well as to test agonists and antagonists of ligand binding. Using labeled soluble ztnfr14, cells expressing the ztnfr14 ligand can be identified by fluorescence immunocytometry or immunohistochemistry. The soluble fusion proteins or soluble Ig fusion protein is useful in studying the distribution of the ztnfr14 ligand in tissues or specific cell lineages, and to provide insight into receptor/ligand biology.

In an alternative approach, a soluble ztnfr14 receptor extracellular ligand-binding region can be expressed as a chimera with immunoglobulin heavy chain constant regions, typically an $F_c$ fragment, which contains two constant region domains and a hinge region, but lacks the variable region. Such fusions are typically secreted as multimeric molecules, wherein the Fc portions are disulfide bonded to each other and two receptor polypeptides are arrayed in close proximity to each other. Fusions of this type can be used to affinity purify the cognate ligand from solution, as an in vitro assay tool, to block signals in vitro by specifically titrating out ligand, and as antagonists in vivo by administering them to block ligand stimulation. To purify ligand, a ztnfr14-Ig fusion protein (chimera) is added to a sample under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. For use in assays, the chimeras are bound to a support via the $F_c$ region and used in an ELISA format.

To direct the export of a ztnfr14 polypeptide from the host cell, the ztnfr14 DNA may be linked to a second DNA segment encoding a sequence other than its own secretory peptide, such as a t-PA secretory peptide. To facilitate purification of the secreted polypeptide, a C-terminal extension, such as substance P, Flag peptide (Hopp et al., *Bio/Technoloy* 6:1204-1210, 1988; available from Eastman Kodak Co., New Haven, Conn.), maltose binding protein, or another polypeptide or protein for which an antibody or other specific binding agent is available, can be fused to the ztnfr14 polypeptide.

The present invention also includes "functional fragments" of ztnfr14 polypeptides and nucleic acid molecules encoding such functional fragments. Routine deletion analyses of nucleic acid molecules can be performed to obtain functional fragments of a nucleic acid molecule that encodes an ztnfr14 polypeptide. As an illustration, DNA molecules having the nucleotide sequence of SEQ ID NOs:1 and 3, can be digested with Bal31 nuclease to obtain a series of nested deletions. The fragments are then inserted into expression vectors in proper reading frame, and the expressed polypeptides are isolated and tested for cell-cell interactions, the ability to bind the ztnfr14 ligand, the ability to reduce known ligand activity, or for the ability to bind anti-ztnfr14 antibodies. One alternative to exonuclease digestion is to use oligonucleotide-directed mutagenesis to introduce deletions or stop codons to specify production of a desired fragment. Alternatively, particular fragments of an ztnfr14 gene can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987), Herschman, "The EGF Receptor," in *Control of Animal Cell Proliferation*, Vol. 1, Boynton et al., (eds.) pages 169-199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of an ztnfr14 gene that has amino acid changes, compared with the amino acid sequences of SEQ ID NOs:2, 4, 30 and 32. A variant ztnfr14 gene can be identified on the basis of structure by determining the level of identity with nucleotide and amino acid sequences of SEQ ID NOs:1, 2, 3, 4, 29, 30, 31, and 32 as discussed above. An alternative approach to identifying a variant gene on the basis of structure is to determine whether a nucleic acid molecule encoding a potential variant ztnfr14 gene can hybridize to a nucleic acid molecule having the nucleotide sequence of SEQ ID NO: 1, as discussed above.

Using the methods discussed herein, one of ordinary skill in the art can identify and/or prepare a variety of polypeptide fragments or variants of SEQ ID NO:2 or that retain the ligand-binding, or intracellular signaling activity of the wild-type ztnfr14 protein. Such polypeptides may include additional amino acids from, for example, cysteine-rich pseudo-repeats, a linker domain, a transmembrane and cytoplasmic domains, including amino acids responsible for intracellular signaling; fusion domains; affinity tags; and the like. Similarly, the cysteine -rich pseudo repeats (i.e., residues 30 to 80 of SEQ ID NO:2, residues 50 to 80 of SEQ ID NO:2, and/or residues 30 to 108 of SEQ ID NO:2) can be substituted for the cysteine-rich pseudo repeats from other TNFR family member to increase or decrease ligand binding, or specificity.

Within the polypeptides of the present invention are polypeptides that comprise an epitope-bearing portion of a protein as shown in SEQ ID NO:2. An "epitope" is a region of a protein to which an antibody can bind. See, for example, Geysen et al., *Proc. Natl. Acad. Sci. USA* 81:3998-4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., *Science* 219:660-666, 1983. Antibodies that recognize short, linear epitopes are particularly useful in analytic and diagnostic applications that employ denatured protein, such as Western blotting (Tobin, *Proc. Natl. Acad. Sci. USA* 76:4350-4356, 1979), or in the analysis of fixed cells or tissue samples. Antibodies to linear epitopes are also useful for detecting fragments of ztnfr14, such as might occur in body fluids or cell culture media.

Antigenic, epitope-bearing polypeptides of the present invention are useful for raising antibodies, including monoclonal antibodies, that specifically bind to a ztnfr14 protein. Antigenic, epitope-bearing polypeptides contain a sequence of at least six, preferably at least nine, more preferably from 15 to about 30 contiguous amino acid residues of a ztnfr14 protein (e.g., SEQ ID NO:2). Polypeptides comprising a larger portion of a ztnfr14 protein, i.e. from 30 to 50 residues up to the entire sequence, are included. It is preferred that the amino acid sequence of the epitope-bearing polypeptide is selected to provide substantial solubility in aqueous solvents, that is the sequence includes relatively hydrophilic residues, and hydrophobic residues are substantially avoided. Preferred such regions include the cysteine-rich pseudo-repeats, the linker domain, the transmembrane domain, or the cytoplasmic domain ztnfr14 and fragments thereof.

The present invention also provides polypeptide fragments or peptides comprising an epitope-bearing portion of an ztnfr14 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides contain at least four to ten amino acids, preferably at least ten to fifteen amino acids, more preferably 15 to 30 amino acids of SEQ ID NOs:2, 4, 30 and 32. Such epitope-bearing peptides and polypeptides can be produced by fragmenting an ztnfr14 polypeptide, or by chemical peptide synthesis, as described herein. Moreover, epitopes can be selected by phage display of random peptide libraries (see, for example, Lane and Stephen. *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105-116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.), *Current Protocols in Immunology*, pages 9.3.1-9.3.5 and pages 9.4.1-9.4.11 (John Wiley & Sons 1997).

ztnfr14 polypeptides can also be used to prepare antibodies that specifically bind to ztnfr14 epitopes, peptides or polypeptides. The ztnfr14 polypeptide or a fragment thereof serves as an antigen (immunogen) to inoculate an animal and elicit an immune response. One of skill in the art would recognize that antigenic, epitope-bearing polypeptides contain a sequence of at least 6, preferably at least 9, and more preferably at least 15 to about 30 contiguous amino acid residues of a ztnfr14 polypeptide. Polypeptides comprising a larger portion of a ztnfr14 polypeptide, i.e., from 30 to 10 residues up to the entire length of the amino acid sequence are included. Antigens or immunogenic epitopes can also include attached tags, adjuvants and carriers, as described herein. Examples of suitable antigens include the ztnfr14 polypeptides encoded by SEQ ID NO:2 from amino acid number 1 to amino acid number 198; polypeptides encoded by SEQ ID NO:30 from amino acid number 1 to amino acid number 308; polypeptides encoded by SEQ ID NO:32 from amino acid number 1 to amino acid number 185.

As an illustration, potential antigenic sites in ztnfr14 can be identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

Antibodies from an immune response generated by inoculation of an animal with these antigens can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., Monoclonal Hybridoma Antibodies: Techniques and Applications, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a ztnfr14 polypeptide or a fragment thereof. The immunogenicity of a ztnfr14 polypeptide may be increased through the use of an adjuvant, such as alum (aluminum hydroxide) or Freund's complete or incomplete adjuvant. Polypeptides useful for immunization also include fusion polypeptides, such as fusions of ztnfr14 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to ztnfr14 protein or peptide, and selection of antibody display libraries in phage or similar vectors (for instance, through use of immobilized or labeled ztnfr14 protein or peptide). Genes encoding polypeptides having potential ztnfr14 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from CLONTECH Laboratories, Inc., (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the ztnfr14 sequences disclosed herein to identify proteins which bind to ztnfr14. These "binding proteins" which interact with ztnfr14 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease.

These binding proteins can also act as ztnfr14 "antagonists" to block ztnfr14 binding and signal transduction in vitro and in vivo. These anti-ztnfr14 binding proteins would be useful for modulating, for example, apoptosis, myogenesis, immunologic recognition, tumor formation, and cell-cell interactions in general.

As used herein, the term "binding proteins" additionally includes antibodies to ztnfr14 polypeptides, the cognate ligand of ztnfr14 polypeptides, proteins useful for purification of ztnfr14 polypeptides, and proteins associated with the cytoplasmic domain (residues 131 to 198 of SEQ ID NO:2). Such cytoplasmic domain associated peptides, also called cytoplasmic mediators, function in intracellular signaling of ztnfr14 polypeptides. See Bazzoni, F. et al., *J. of Inflammation* 45:221-238, 1995. These cytoplasmic mediators include, but are not limited to TRAP-1, TRADD, RIP, TRAF-1-6, LAP-1, FADDIMORT-1, and CAP-1.

Antibodies are determined to be specifically binding if they exhibit a threshold level of binding activity (to a ztnfr14 polypeptide, peptide or epitope) of at least 10-fold greater than the binding affinity to a control (non-ztnfr14) polypeptide. The binding affinity of an antibody can be readily determined by one of ordinary skill in the art, for example, by Scatchard analysis (Scatchard, G., *Ann. NY Acad. Sci.* 51: 660-672, 1949).

A variety of assays known to those skilled in the art can be utilized to detect antibodies which specifically bind to ztnfr14 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant ztnfr14 protein or polypeptide.

Antibodies to ztnfr14 may be used for immunohistochemical tagging cells that express ztnfr14; for isolating ztnfr14 by affinity purification; for diagnostic assays for determining circulating levels of ztnfr14 polypeptides; for detecting or quantitating soluble ztnfr14 as marker of underlying pathology or disease; in analytical methods employing FACS; for screening expression libraries; for generating anti-idiotypic antibodies; and as neutralizing antibodies or as antagonists to block ztnfr14 in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to ztnfr14 or fragments thereof may be used in vitro to detect denatured ztnfr14 or fragments thereof in assays, for example, Western Blots or other assays known in the art.

The soluble ztnfr14 is useful in studying the distribution of ligands on tissues or specific cell lineages, and to provide insight into receptor/ligand biology. Using labeled ztnfr14, cells expressing the ligand are identified by fluorescence immunocytometry or immunocytochemistry. Application may also be made of the specificity of TNF receptors for their ligands.

Antibodies can be made to soluble ztnfr14 polypeptides which are FLAG™ tagged. Alternatively, such polypeptides form a fusion protein with Human Ig. In particular, antiserum containing polypeptide antibodies to FLAG[198]-tagged soluble ztnfr14 can be used in analysis of tissue distribution of ztnfr14 by immunohistochemistry on human or primate tissue. These soluble ztnfr14 polypeptides can also be used to immunize mice in order to produce monoclonal antibodies to a soluble human ztnfr14 polypeptide. Monoclonal antibodies to a soluble human ztnfr14 polypeptide can also be used to mimic ligand/receptor coupling, resulting in activation or inactivation of the ligand/receptor pair. For instance, it has been demonstrated that cross-linking anti-soluble CD40 monoclonal antibodies provides a stimulatory signal to B cells that have been sub-optimally activated with anti-IgM or LPS, and results in proliferation and immunoglobulin production. These same monoclonal antibodies act as antagonists when used in solution by blocking activation of the receptor. Monoclonal antibodies to ztnfr14 can be used to determine the distribution, regulation and biological interaction of the ztnfr14 /ztnfr14-ligand pair on specific cell lineages identified by tissue distribution studies.

Soluble receptors or antibodies to the receptor can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (ligand or antigen, respectively, for instance). More specifically, ztnfr14 polypeptides or anti-ztnfr14 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer or inflammatory cells or tissues). Alternatively, a fusion protein including only the cysteine-rich pseudo-repeats may be suitable for directing a detectable molecule, a cytotoxic molecule or a complementary molecule to a cell or tissue type of interest. Similarly, the corresponding ligand to ztnfr14 can be conjugated to a detectable or cytotoxic molecule and provide a generic targeting vehicle for cell/tissue-specific delivery of generic anti-complementary-detectable/cytotoxic molecule conjugates.

As would be evident to one of skill in the art, certain molecular markers can aid in identifying the existence and prognosis of disease. Such markers include, for example, p53, C-Ki-ras, and c-erbB-2. See, in general, Schneider, P. et al. *Br. J. Cancer* 83(4):473-479, 2000; and Watatani, M., et al., *Surg.* *Today* 30(6): 516-522, 2000. One of routine skill in the art will also know that such molecular markers can also be used as a target for treatment with or with out combination therapy with other agents, including chemotherapy. An example of a treatment approach to a membrane bound receptor is the use of trastuzumab to treat breast cancer wherein the cancerous tissue is overexpressing HER2. See, for example, Baselga, J., et al.,*Semin. Oncol.* 26 (4 Suppl 12): 78-83, 1999; Ravdin, P., *Semin. Oncol.* 26 (4 Suppl 12): 117-23, 1999; Shak, S., *Semin. Oncol.* 26 (4 Suppl 12): 71-7, 1999; and Stebbing, J., et al., *Cancer Treat. Rev.* 26(4): 287-290, 2000.

As a protein that shows upregulation in some tumor cells, such as, for example, neuroblastoma, melanoma, and lymphoma, polynucleotides and polypeptides of the present invention, fragments thereof, and binding proteins thereto (including antibodies, and ligands) can be used in a multitude of ways to detect and/or diagnose such diseases. For example, polynucleotide probes, (including DNA, RNA, and peptide-nucleic acid) can be used as a diagnostic marker to determine if such disease tissues are present. Hybridization techniques are taught elsewhere in this application and are widely known by one of skill in the art. Such polynucleotides, fragments thereof, and fusions thereto, can also be used to incorporate the proper polynucleotide sequence into a tissue, cell line or organism defective in the proper gene, as is also taught elsewhere in this application. As a means of treating such disease, said polunucleotides, fragments thereof, and fusions thereto, can also be administered in the presence of an agent that allows the DNA to traverse the cell membrane and act as a tag for cell ablation to a therapeutic agent with an appropriate binding partner. In this manner cells which contain ztnfr14 polynucleotides can be inhibited or destroyed.

Ztnfr14 polypeptides, fragments thereof, and fusions thereto, can be used both diagnostically and therapeutically. Such ztnfr14 polypeptides, including soluble polypeptides, can be used as a marker for identifying tumor cells, such as, for example, melanoma, lung carcinoma, breast carcinoma, osteosarcoma, and lymphoma. As a soluble polypeptide, this diagnosis can be determined by measuring ztnfr14 polypeptides, fragments thereof, and fusions thereto in body fluids, including, but not limited to, blood, plasma, saliva, urine, lavage fluid and biopsy fluid. As a membrane bound polypeptide ztnfr14 polypeptides, fragments thereof, and fusions thereto, can be measured in tissue biopsies (i.e., excised from the body) as well as locally (i.e., epithlelial surfaces) using imaging and/or visualization. The targeting of such disease tissues will be helpful in treatment options. For example, if the spread of disease is limited, such visualization will aid a surgeon in resection of disease tissue. Similarly, the presence of membrane bound ztnfr14 can be used as a target for a ztnfr14 binding protein (including its ligand or antibodies) that has been fused or conjugated to an inhibitory or ablative agent.

In another embodiment, ztnfr14-cytokine fusion proteins or antibody-cytokine fusion proteins can be used for enhancing in vivo killing of target tissues (for example, stomach, uterus, as well as in neuroblastoma, melanoma, and lymphoma), if the ztnfr14 polypeptide or anti-ztnfr14 antibody targets hyperproliferative tissues from these organs. (See, generally, Hornick et al., *Blood* 89:4437-47, 1997). They described fusion proteins that enable targeting of a cytokine to a desired site of action, thereby providing an elevated local concentration of cytokine. Suitable ztnfr14 polypeptides or anti-ztnfr14 antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

ztnfr14 polynucleotides and/or polypeptides may be useful for regulating the maturation of TNF ligand-bearing cells, such as T cells, B cells, lymphocytes, peripheral blood mononuclear cells, polymorphonuclear leukocytes, fibroblasts and hematopoietic cells. ztnfr14 polypeptides will also find use in mediating metabolic or physiological processes in vivo. The effects of a compound on proliferation and differentiation can be measured in vitro using cultured cells. Bioassays and ELISAs are available to measure cellular response to ztnfr14, in particular are those which measure changes in cytokine production as a measure of cellular response (see for example, *Current Protocols in Immunology* ed. John E. Coligan et al., NIH, 1996). Assays to measure other cellular responses, including antibody isotype, monocyte activation, NK cell formation, antigen presenting cell function, apoptosis are known in the art.

The ztnfr14 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, NY, 1989, and Ausubel et al., eds., *Current Protocols in Molecular Biology*, John Wiley and Sons, Inc., NY, 1987.

In general, a DNA sequence encoding a ztnfr14 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a ztnfr14 polypeptide into the secretory pathway of a host cell, a secretory signal sequence (also known as a leader sequence, prepro sequence or pre sequence) can be provided in the expression vector. The secretory signal sequence may the native ztnfr14 sequence or be derived from another secreted protein (e.g., APO4, or t-PA) or synthesized de novo. The secretory signal sequence is operably linked to the ztnfr14 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

The cytoplasmic domain of ztnfr14 can be substituted by a heterologous sequence providing a different cytoplasmic domain. In this case, the fusion product can be secreted, and the cysteine-rich pseudo-repeat domain of ztnfr14 can direct the new cytoplasmic domain to a specific tissue described above. This substituted cytoplasmic domain can be chosen from the cytoplasmic domain represented by the TNFR protein families. Similarly, the cysteine-rich pseudo-repeat domain of ztnfr14 protein can be substituted by a heterologous sequence providing a different cysteine-rich pseudo-repeat domain. Again, the fusion product can be secreted and the substituted cysteine-rich pseudo-repeat domain can target the cytoplasmic domain of ztnfr14 to a specific tissue. The substituted cysteine-rich pseudo-repeat domain can be chosen from the cysteine-rich pseudo-repeat domains of the TNFR protein families. In these cases, the fusion products can be soluble or membrane-bound proteins.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-5, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993, and viral vectors (Miller and Rosman, *BioTechniques* 7:980-90, 1989; Wang and Finer, *Nature Med.* 2:714-6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins, such as CD4, CD8, Class I MHC, or placental alkaline phosphatase, may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci.* (Bangalore) 11:47-58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant ztnfr14 baculovirus utilizes a transposon-based system described by Luckow (Luckow, V. A, et al., *J Virol* 67:4566-79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the ztnfr14 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case ztnfr14. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J. Gen. Virol.* 71:971-6, 1990; Bonning, B. C. et al., *J. Gen. Virol.* 75:1551-6, 1994; and, Chazenbalk, G. D., and Rapoport, B., *J. Biol Chem* 270:1543-9, 1995. In such transfer vector constructs, a short or long version of the basic protein promoter can be used. Moreover, transfer vectors can be constructed which replace the native ztnfr14 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native ztnfr14 secretory signal sequence. In addition, transfer vectors can include an in-frame fusion with DNA encoding an epitope tag at the C- or N-terminus of the expressed ztnfr14 polypeptide, for example, a Glu-Glu epitope tag (Grussenmeyer, T. et al., *Proc. Natl. Acad. Sci.* 82:7952-4, 1985). Using a technique known in the art, a transfer vector containing ztnfr14 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses ztnfr14 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5\times10^5$ cells to a density of $1-2\times10^6$ cells at which time a recombinant viral stock is added at a multiplicity of infection (MOI) of 0.1 to 10, more typically near 3. Procedures used are generally described in available laboratory manuals (King, L. A. and Possee, R. D., ibid.; O'Reilly, D. R. et al., ibid.; Richardson, C. D., ibid.). Subsequent purification of the ztnfr14 polypeptide from the supernatant can be achieved using methods described herein.

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459-65, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. The use of *Pichia methanolica* as host for the production of recombinant proteins is disclosed in U.S. Pat. Nos. 5,716,808, 5,736,383, 5,854,039, and 5,888,768.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a ztnfr14 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806-9, 1993; and Chung et al., *Proc. Natl. Acad. Sci. USA* 90:10145-9, 1993). In a second method, translation is carried out in *Xenopus* ocytes by microinjection of mutated mRNA and chemically aminoacylated suppressor tRNAs (Turcatti et al., *J. Biol. Chem.* 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

A limited number of non-conservative amino acids, amino acids that are not encoded by the genetic code, non-naturally occurring amino acids, and unnatural amino acids may be substituted for ztnfr14 amino acid residues.

It is preferred to purify the polypeptides of the present invention to ≧80% purity, more preferably to ≧90% purity, even more preferably ≧95% purity,. and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant ztnfr14 proteins (including chimeric polypeptides and multimeric proteins) are purified by conventional protein purification methods, typically by a combination of chromatographic techniques. See, in general, Affinity *Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321-1325, 1988. Proteins comprising a glu-glu tag can be purified by immunoaffinity chromatography according to conventional procedures. See, for example, Grussenmeyer et al., ibid. Maltose binding protein fusions are purified on an amylose column according to methods known in the art.

The polypeptides of the present invention can be isolated by a combination of procedures including, but not limited to, anion and cation exchange chromatography, size exclusion, and affinity chromatography. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp. 529-39). Within additional embodiments of the invention, a fusion of the polypeptide of interest and an affinity tag (e.g., maltose-binding protein, an immunoglobulin domain) may be constructed to facilitate purification.

ztnfr14 polypeptides can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989. In vitro synthesis is particularly advantageous for the preparation of smaller polypeptides.

Using methods known in the art, ztnfr14 proteins can be prepared as monomers or multimers; glycosylated or non-glycosylated; pegylated or non-pegylated; and may or may not include an initial methionine amino acid residue.

The activity of ztnfr14 polypeptides can be measured using a variety of assays that measure, for example, cell-cell interactions, ztnfr14 ligand binding, tumor cell proliferation, B-cell activation, NK-cell activation, T-cell activation and other biological functions associated with ztnfr14 ligand/receptor binding.

Proteins, including alternatively spliced peptides, of the present invention are useful for tumor suppression, immunologic recognition, and growth and differentiation either working in isolation, or in conjunction with other molecules (growth factors, cytokines, etc.) in stomach, uterus, and in cancerous conditions such as neuroblastomas, melanomas, and lymphomas. Alternative splicing of ztnfr14 may cell-type specific and confer activity to specific tissues.

As polynucleotides of the present invention have been identified in stomach, uterus, neuroblastomas, melanomas, and lymphoma cells among other cancerous cell lines, polynucleotides of ztnfr14 can be used to detect these cell types by hybridization, or with ztnfr14 binding proteins. Similarly antibodies to the ztnfr14 polypeptides can detect cells expressing the surface bound ztnfr14 receptor. Such detection can be useful to determine metastasis, disease stage, or primary diagnosis of disease. Additionally, proliferation, differentiation and/or apoptosis of these cell types can be modulated by contacting the cells with ztnfr14 binding proteins, including a ztnfr14-cognate ligand, or an antibody to ztnfr14, for example. The proliferation, and/or differentiation cells can also be mediated by ztnfr14 polypeptides, or fragments thereof, as an antagonist of cell signaling by binding to the ztnfr14 ligand and thereby reducing the interaction between ligand and membrane-bound ztnfr14 proteins. The effects of the modulation of ztnfr14 molecules on proliferation and/or differentiation can be measured, for example, by the presence or absence of cell markers specific to these cell types, or by measuring other manifestations of these diseases. For example, ztnfr14 polypeptides or fragments thereof, as well as ztnfr14 binding proteins can be administered to cells of neuroblastomas and inhibition of the cancerous growth can be monitored by conventional imaging techniques.

The activity of molecules of the present invention can be measured using a variety of assays that, for example, measure neogenesis or hyperplasia (i.e., proliferation) of tissues of the nerves, skin, or hematopoetic cell lineages. Additional activities likely associated with the polypeptides of the present invention include proliferation of lymphoid cells directly or indirectly through other growth factors.

The ztnfr14 polypeptides of the present invention can be used to study proliferation or differentiation in stomach and uterus, as well as in neuroblastoma, melanoma, and lymphoma. Such methods of the present invention generally comprise incubating cells derived from these tissues in the presence and absence of ztnfr14 polypeptide, monoclonal antibody, agonist or antagonist thereof and observing changes in cell proliferation or differentiation. Cell lines from these tissues are commercially available from, for example, American Type Culture Collection (Manasas, Va.).

Proliferation can be measured using cultured uterine or stomach cells or in vivo by administering molecules of the claimed invention to an appropriate animal model. Generally, proliferative effects are observed as an increase in cell number and therefore, may include inhibition of apoptosis, as well as mitogenesis. Cultured cells include uterine fibroblasts, neuroblastomas, melanoma, and lymphoma, as well as from primary cultures. Established cell lines are easily identifiable by one skilled in the art and are available from ATCC (Manasas, Va.). Assays measuring cell proliferation are well known in the art. For example, assays measuring proliferation include such assays as chemosensitivity to neutral red dye (Cavanaugh et al., *Investigational New Drugs* 8:347-354, 1990), incorporation of radiolabelled nucleotides (Cook et al., *Analytical Biochem.* 179:1-7, 1989), incorporation of 5-bromo-2'-deoxyuridine (BrdU) in the DNA of proliferating cells (Porstmann et al., *J. Immunol. Methods* 82:169-179, 1985), and use of tetrazolium salts (Mosmann, *J. Immunol. Methods* 65:55-63, 1983; Alley et al., *Cancer Res.* 48:589-601, 1988; Marshall et al., *Growth Reg.* 5:69-84, 1995; and Scudiero et al., *Cancer Res.* 48:4827-4833, 1988).

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors and receptor-like complementary molecules. The stage of a cell population's differentiation is monitored by identification of markers present in the cell population. For example, myocytes, osteoblasts, adipocytes, chrondrocytes, fibroblasts and reticular cells are believed to originate from a common mesenchymal stem cell (Owen et al., *Ciba Fdn. Symp.* 136:42-46, 1988). Markers for mesenchymal stem cells have not been well identified (Owen et al., *J. of Cell Sci.* 87:731-738, 1987), so identification is usually made at the progenitor and mature cell stages. The novel polypeptides of the present invention are useful for studies to isolate mesenchymal stem cells and uterine myocyte progenitor cells, both in vivo and ex vivo.

There is evidence to suggest that factors that stimulate specific cell types down a pathway towards terminal differentiation or dedifferentiation affect the entire cell population originating from a common precursor or stem cell. Thus, ztnfr14 polypeptides may stimulate inhibition or proliferation of endocrine and exocrine cells of the uterus, stomach as well as in melanoma, neuroblastoma, and lymphoma.

Molecules of the present invention may, while stimulating proliferation or differentiation of uterine fibroblasts, inhibit proliferation or differentiation of adipocytes, by virtue of their effect on common precursor/stem cells. The novel polypeptides of the present invention are useful to study neural and epithelial stem cells and uterus, as well as in melanoma, neuroblastoma, and lymphoma, both in vivo and ex vivo.

Assays measuring differentiation include, for example, measuring cell-surface markers associated with stage-specific expression of a tissue, enzymatic activity, functional activity or morphological changes (Watt, *FASEB*, 5:281-284, 1991; Francis, *Differentiation* 57:63-75, 1994; Raes, *Adv. Anim. Cell Biol. Technol. Bioprocesses*, 161-171, 1989).

Proteins, including alternatively spliced peptides, and fragments, of the present invention are useful for studying cell-cell interactions, fertilization, development, immune recognition, growth control, tumor suppression, and embryo maturation. ztnfr14 molecules, variants, and fragments can be applied in isolation, or in conjunction with other molecules (growth factors, cytokines, etc.) in the stomach and uterus, as well as in melanoma, neuroblastoma, and lymphoma.

Proteins of the present invention are useful for delivery of therapeutic agents such as, but not limited to, proteases, radionuclides, chemotherapy agents, and small molecules. Effects of these therapeutic agents can be measured in vitro using cultured cells, ex vivo on tissue slices, or in vivo by administering molecules of the claimed invention to the appropriate animal model. An alternative in vivo approach for assaying proteins of the present invention involves viral delivery systems. Exemplary viruses for this purpose include adenovirus, herpesvirus, lentivirus, vaccinia virus and adeno-associated virus (AAV). Adenovirus, a double-stranded DNA virus, is currently the best studied gene transfer vector for delivery of heterologous nucleic acid (for a review, see T. C. Becker et al., *Meth. Cell Biol.* 43:161-89, 1994; and J. T. Douglas and D. T. Curiel, *Science & Medicine* 4:44-53, 1997). The adenovirus system offers several advantages:

adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol.* 72:2022-2032, 1998; Raper, S. E. et al., *Human Gene Therapy* 9:671-679, 1998). In addition, deletion of E2b is reported to reduce immune responses (Amalfitano, A. et al., *J. Virol.* 72:926-933, 1998). Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J.* 11:615-623, 1997.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see Garnier et al., *Cytotechnol.* 15:145-55, 1994). With either protocol, an expressed, secreted heterologous protein can be repeatedly isolated from the cell culture supernatant. Within the infected 293S cell production protocol, non-secreted proteins may also be effectively obtained.

As a soluble or cell-surface protein, the activity of ztnfr14 polypeptide or a peptide to which ztnfr14 binds can be measured by a silicon-based biosensor microphysiometer which measures the extracellular acidification rate or proton excretion associated with cell-surface protein interactions and subsequent physiologic cellular responses. An exemplary device is the Cytosensorm Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906-1912, 1992; Pitchford, S. et al., *Meth. Enzymol.* 228:84-108, 1997; Arimilli, S. et al., *J. Immunol. Meth.* 212:49-59, 1998; Van Liefde, I. et al., *Eur. J. Pharmacol.* 346:87-95, 1998. The microphysiometer can be used for assaying adherent or nonadherent eukaryotic or prokaryotic cells. By measuring extracellular acidification changes in cell media over time, the microphysiometer directly measures cellular responses to various stimuli, including proteins, agonists, and antagonists which affect a ztnfr14-mediated pathway. ztnfr14-responsive eukaryotic cells comprise cells into which a polynucleotide for ztnfr14 has been transfected creating a cell that is responsive to activation of ztnfr14; or cells naturally responsive to activation of ztnfr14. Differences, measured by a change in the response of cells exposed to ztnfr14 activation, relative to a control not exposed to ztnfr14 activation, are a direct measurement of ztnfr14-mediated cellular responses. Moreover, such ztnfr14-mediated responses can be assayed under a variety of stimuli. The present invention provides a method of identifying agonists and antagonists of ztnfr14 protein, comprising providing cells responsive to activation of ztnfr14 polypeptide, culturing a first portion of the cells in the absence of a test compound, culturing a second portion of the cells in the presence of a test compound, and detecting a change in a cellular response of the second portion of the cells as compared to the first portion of the cells. The change in cellular response is shown as a measurable change in extracellular acidification rate. Moreover, culturing a third portion of the cells in the presence of ztnfr14 polypeptide and the absence of a test compound provides a positive control for the ztnfr14-responsive cells, and a control to compare the agonist activity of a test compound with that of the ztnfr14 polypeptide. Antagonists of ztnfr14 can be identified by exposing the cells to ztnfr14 protein in the presence and absence of the test compound, whereby a reduction in ztnfr14-stimulated activity is indicative of antagonist activity in the test compound.

Similarly, the microphysiometer, can be used to rapidly identify cells, tissues, or cell lines which activate a ztnfr14-stimulated pathway. Such tissues and cell lines can be used to identify ligands, antagonists and agonists of ztnfr14 polypeptide as described above. Using similar methods, cells expressing ztnfr14 can be used to identify cells which stimulate or block a ztnfr14-signaling pathway.

In view of the upregulation of ztnfr14 during immune cell activation, agonists (including the native cysteine-rich pseudo-repeat and cytoplasmic domains) and antagonists to ztnfr14/ztnfr14 ligand binding have enormous potential in both in vitro and in vivo applications. Compounds identified as ztnfr14 agonists and antagonists are useful for studying cell-cell interactions, apoptosis, tumor proliferation and suppression, infection, and inflammation in vitro and in vivo. For example, ztnfr14 and agonist compounds are useful as components of defined cell culture media, and may be used alone or in combination with cytokines and hormones to replace serum that is commonly used in cell culture. Agonists are thus useful in specifically promoting the growth and/or development of cells of the myeloid and lymphoid lineages in culture. Additionally, ztnfr14 polypeptides and ztnfr14 agonists, including small molecules are useful as a research reagent, such as for the expansion, differentiation, proliferation, and/or cell-cell interactions of uterus, as well as in melanoma, osteosarcoma, breast carcinoma, and lymphoma, and in tumors of the lung. ztnfr14 polypeptides are added to tissue culture media for these cell types.

Compounds identified as ztnfr14 agonists are useful for modifying the proliferation and development of target cells in vitro and in vivo. For example, agonist compounds are useful alone or in combination with other cytokines and hormones as components of defined cell culture media. Agonists are thus useful in specifically mediating the growth and/or development of ztnfr14-bearing T lymphocytes or other ztnfr14-bearing cells in culture. Agonists and antagonists may also prove useful in the study of effector functions of T lymphocytes, in particular T lymphocyte activation and differentiation. Antagonists are useful as research reagents for characterizing ligand-receptor interaction.

As a member of the TNFR family, ztnfr14 polypeptides are likely to be involved in the immune response to infection. Lymphotoxin-beta receptor, another member of this receptor family, has been shown to regulate HIV-1 replication. (Marshall, W. L. et al., *J. Immun.* 162: 6016-6023, 1999). Further, it has been shown that cosignaling via the lymphotoxin-beta receptor and TNF-receptors is probably involved in the modulation of HIV-1 replication and the subsequent determination of HIV-1 viral burden in monocytes. ztnfr14 polypeptides, agonists, and antagonists can be used to treat microbial infections. Such infections include bacterial, yeast, and viral infections. Anti-microbial activity of proteins is evaluated by techniques that are known in the art. For example, anti-microbial activity can be assayed by evaluating the sensitivity of microbial cell cultures to test agents and by evaluating the protective effect of test agents on infected mice. See, for example, Musiek et al., *Antimicrob. Agents Chemothr.* 3:40, 1973. Antiviral activity can also be assessed by protection of mammalian cell cultures. Known techniques for evaluating anti-microbial activity include, for example, Barsum et al., *Eur. Respir. J.* 8:709-714, 1995; Sandovsky-Losica et al., *J. Med. Vet. Mycol (England)* 28:279-287, 1990; Mehentee et al., *J. Gen. Microbiol (England)* 135(:2181-2188, 1989; and Segal and Savage, *J. Med. Vet. Mycol.* 24:477-479, 1986. Assays specific for anti-viral activity include, for example, those described by Daher et al., *J. Virol.* 60:1068-1074, 1986. Similarly, assays measuring HIV-1 viral burden on cells can be used.

Shock is a manifestation of infection. Studies show that increased serum TNF levels are associated with high mortality rates. See Wage, A. et al., *Lancet i:*355-357, 1987, and Girardin et al., *New. Eng. J. Med.* 39: 397-400, 1988. Soluble TNF receptors, including ztnfr14 polypeptides of the present invention, may be useful to reduce serum concentrations of TNF, and minimize the effects of sepsis.

The invention also provides antagonists, which either bind to ztnfr14 polypeptides or, alternatively, to a ligand to which ztnfr14 polypeptides bind, thereby inhibiting or eliminating the function of ztnfr14. Such ztnfr14 antagonists would include antibodies; polypeptides which bind either to the ztnfr14 polypeptide or to its ligand; natural or synthetic analogs of ztnfr14 ligands which retain the ability to bind the receptor but do not result in either ligand or receptor signaling. Such analogs could be peptides or peptide-like compounds. Natural or synthetic small molecules which bind to ztnfr14 polypeptides and prevent signaling are also contemplated as antagonists. Also contemplated are soluble ztnfr14 receptors. As such, ztnfr14 antagonists would be useful as therapeutics for treating certain disorders where blocking signal from either a ztnfr14 receptor or ligand would be beneficial. Antagonists are useful as research reagents for characterizing ligand-receptor interaction.

ztnfr14 polypeptides may be used within diagnostic systems to detect the presence of ligand polypeptides. Antibodies or other agents that specifically bind to ztnfr14 may also be used to detect the presence of circulating or membrane bound receptor or ligand polypeptides. Such detection methods are well known in the art and include, for example, enzyme-linked immunosorbent assay (ELISA) and radioimmunoassay. Immunohistochemically labeled ztnfr14 antibodies can be used to detect ztnfr14 receptor and/or ligands in tissue samples. ztnfr14 levels can also be monitored by such methods as RT-PCR, where ztnfr14 mRNA can be detected and quantified. The information derived from such detection methods would provide insight into the significance of ztnfr14 polypeptides in various diseases, and as such would serve as diagnostic tools for diseases for which altered levels of ztnfr14 are significant. Altered levels of ztnfr14 receptor polypeptides may be indicative of pathological conditions including cancer, autoimmune disorders, bone disorders, inflammation and immunodeficiencies.

Antagonists are also useful as research reagents for characterizing sites of interactions between members of complement/anti-complement pairs as well as sites of cell-cell interactions. Inhibitors of ztnfr14 activity (ztnfr14 antagonists) include anti-ztnfr14 antibodies and soluble ztnfr14 polypeptides (such as described above), as well as other peptidic and non-peptidic agents (including ribozymes).

ztnfr14 can also be used to identify inhibitors (antagonists) of its activity. Test compounds are added to the assays disclosed herein to identify compounds that inhibit the activity of ztnfr14. In addition to those assays disclosed herein, samples can be tested for inhibition of ztnfr14 activity within a variety of assays designed to measure receptor/ligand binding or the stimulation/inhibition of ztnfr14-dependent cellular responses. For example, ztnfr14-responsive cell lines can be transfected with a reporter gene construct that is responsive to a ztnfr14-stimulated cellular pathway. Reporter gene constructs of this type are known in the art, and will generally comprise a DNA response element operably linked to a gene encoding an assayable protein, such as luciferase, or a metabolite, such as cyclic AMP. DNA response elements can include, but are not limited to, cyclic AMP response elements (CRE), hormone response elements (HRE), insulin response element (IRE) (Nasrin et al., *Proc. Natl. Acad. Sci. USA* 87:5273-7, 1990) and serum response elements (SRE) (Shaw et al. *Cell* 56: 563-72, 1989). Cyclic AMP response elements are reviewed in Roestler et al., *J. Biol. Chem.* 263 (19):9063-6; 1988 and Habener, *Molec. Endocrinol.* 4 (8):1087-94; 1990. Hormone response elements are reviewed in Beato, *Cell* 56:335-44; 1989. Such a reporter gene construct would contain a cysteine-rich pseudo-repeat that, upon binding a TNF, would signal intracellularly through, for example, a SRE reporter. Candidate compounds, solutions, mixtures or extracts are tested for the ability to inhibit the activity of ztnfr14 on the target cells, as evidenced by a decrease in ztnfr14 stimulation of reporter gene expression. Assays of this type will detect compounds that directly block ztnfr14 binding to a cell-surface protein, i.e., ligand, or the anti-complementary member of a complementary/anti-complementary pair, as well as compounds that block processes in the cellular pathway subsequent to complement/anti-complement binding. In the alternative, compounds or other samples can be tested for direct blocking of ztnfr14 binding to a ligand using ztnfr14 tagged with a detectable label (e.g., $^{125}$I, biotin, horseradish peroxidase, FITC, and the like). Within assays of this type, the ability of a test sample to inhibit the binding of labeled ztnfr14 to the TNF is indicative of inhibitory activity, which can be confirmed through secondary assays. TNFs used within binding assays may be cellular TNFs, soluble TNFs, or isolated, immobilized TNFs.

The activity of agonists and antagonists can be determined by activity assays which determine the potency of receptor/ligand engagement. Stably transfected cell lines, which co-express high levels of reporter gene constructs for NfKB, NFAT-1 and AP-1 can be made which express ztnfr14. A ztnfr14 ligand can be found to signal through the reporter genes in these constructs. Soluble ztnfr14 and antibodies can be used to measure binding.

A ztnfr14 ligand-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligands are passed through the column one or more times to allow ligands to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complementary/anti-complementary pair or other cell-surface binding protein) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229-40, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complementary/anti-complementary pair is present in the sample, it will bind to the immobilized ligand, antibody or member, respectively, causing a change in the refractive index of the medium, which is detected as a change in surface plasmon resonance of the gold film. This system allows the determination of on- and off-rates, from which binding affinity can be calculated, and assessment of.

Ligand binding receptor polypeptides can also be used within other assay systems known in the art. Such systems include Scatchard analysis for determination of binding affinity (see Scatchard, *Ann. NY Acad. Sci.* 51: 660-72, 1949) and calorimetric assays (Cunningham et al., *Science* 253:545-48, 1991; Cunningham et al., *Science* 245:821-25, 1991).

A "soluble protein" is a protein that is not bound to a cell membrane. Soluble proteins are most commonly ligand-binding receptor polypeptides that lack transmembrane and cytoplasmic domains. Soluble proteins can comprise additional amino acid residues, such as affinity tags that provide for purification of the polypeptide or provide sites for attachment of the polypeptide to a substrate, or immunoglobulin constant region sequences. Many cell-surface proteins have naturally occurring, soluble counterparts that are produced by proteolysis or translated from alternatively spliced mRNAs. Proteins are said to be substantially free of transmembrane and intracellular polypeptide segments when they lack sufficient portions of these segments to provide membrane anchoring or signal transduction, respectively.

Soluble forms of ztnfr14 polypeptides may act as antagonists to or agonists of ztnfr14 polypeptides, and would be useful to modulate the effects of ztnfr14 in stomach, uterus, as well as in melanoma, neuroblastomas, and lymphoma. Thus, the isoform of ztnfr14 that does not contain a transmembrane domain will be soluble, and may act as an agonist or antagonist of ztnfr14 activity. Since polypeptides of this nature are not anchored to the membrane, they can act at sites distant from the tissues in which they are expressed. Thus, the activity of the soluble form of ztnfr14 polypeptides can be more wide spread than its membrane-anchored counterpart. Both isoforms would be useful in studying the effects of the present invention in vitro an in vivo.

Molecules of the present invention can be used to identify and isolate TNFs, or members of complement/anti-complement pairs involved in cell-cell interactions. For example, proteins and peptides of the present invention can be immobilized on a column and membrane preparations run over the column (*Immobilized Affinity Ligand Techniques*, Hermanson et al., eds., Academic Press, San Diego, Calif., 1992, pp.195-202). Proteins and peptides can also be radiolabeled (*Methods in Enzymol.*, vol. 182, "Guide to Protein Purification", M. Deutscher, ed., Acad. Press, San Diego, 1990, 721-37) or photoaffinity labeled (Brunner et al., *Ann. Rev. Biochem.* 62:483-514, 1993 and Fedan et al., *Biochem. Pharmacol.* 33:1167-80, 1984) and specific cell-surface proteins can be identified.

The molecules of the present invention will be useful in modulating abnormal cell growth, proliferation and differentiation. The polypeptides, nucleic acid and/or antibodies of the present invention can be used in treatment of disorders associated with infection, tumor growth, immunodeficiency, auto-immunity, and fertility. The molecules of the present invention can be used to modulate cell adhesion, cell fusion, and signaling or to treat or prevent development of pathological conditions in such diverse tissue as stomach, uterus, neuroblastoma, melanoma, and lymphoma. In particular, certain diseases may be amenable to such diagnosis, treatment or prevention. These diseases include, but are not limited to, melanoma, neuroblastoma, autoimmune disease, and immunodeficiency. The molecules of the present invention can be used to modulate inhibition and proliferation of tissues in the stomach and uterus, as well as cells of melanoma, neuroblastoma, and lymphoma.

Polynucleotides encoding ztnfr14 polypeptides are useful within gene therapy applications where it is desired to increase or inhibit ztnfr14 activity. If a mammal has a mutated or absent ztnfr14 gene, the ztnfr14 gene can be introduced into the cells of the mammal. In one embodiment, a gene encoding a ztnfr14 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320-30, 1991); an attenuated adenovirus vector, such as the vector described by Stratford-Perricaudet et al., *J. Clin. Invest.* 90:626-30, 1992; and a defective adeno-associated virus vector (Samulski et al., i *J. Virol.* 61:3096-101, 1987; Samulski et al., *J. Virol.* 63:3822-8, 1989).

In another embodiment, a ztnfr14 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980, 289; Markowitz et al., *J. Virol.* 62:1120, 1988; Temin et al., U.S. Pat. No. 5,124,263; International Patent Publication No. WO 95/07358, published Mar. 16, 1995 by Dougherty et al.;

and Kuo et al., *Blood* 82: 845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413-7, 1987; Mackey et al., *Proc. Natl. Acad. Sci. USA* 85:8027-31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Similarly, the ztnfr14 polynucleotides (SEQ ID NOs:1, 3, 29 and 31) can be used to target specific tissues such as tissues of the stomach and uterus, as well as in cells of melanoma, neuroblastoma, and lymphoma. It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963-7, 1992; Wu et al., *J. Biol. Chem.* 263:14621-4, 1988.

Various techniques, including antisense and ribozyme methodologies, can be used to inhibit ztnfr14 gene transcription and translation, such as to inhibit cell proliferation in vivo. Polynucleotides that are complementary to a segment of a ztnfr14-encoding polynucleotide (e.g., a polynucleotide as set forth in SEQ ID NOs:1 or 3) are designed to bind to ztnfr14-encoding mRNA and to inhibit translation of such mRNA. Such antisense polynucleotides are used to inhibit expression of ztnfr14 polypeptide-encoding genes in cell culture or in a subject.

Mice engineered to express the ztnfr14 gene, referred to as "transgenic mice," and mice that exhibit a complete absence of ztnfr14 gene function, referred to as "knockout mice," may also be generated (Snouwaert et al., *Science* 257:1083, 1992), may also be generated (Lowell et al., *Nature* 366:740-42, 1993; Capecchi, M. R., Science 244:1288-1292, 1989; Palmiter, R. D. et al. *Annu Rev Genet.* 20:465-499, 1986). For example, transgenic mice that over-express ztnfr14, either ubiquitously or under a tissue-specific or tissue-restricted promoter can be used to ask whether over-expression causes a phenotype. For example, over-expression of a wild-type ztnfr14 polypeptide, polypeptide fragment or a mutant thereof may alter normal cellular processes, resulting in a phenotype that identifies a tissue in which ztnfr14 expression is functionally relevant and may indicate a therapeutic target for the ztnfr14, its agonists or antagonists. For example, a transgenic mouse to engineer is one that over-expresses the soluble ztnfr14 polypeptide or the membrane-bound receptor. Moreover, such over-expression may result in a phenotype that shows similarity with human diseases. Similarly, knockout ztnfr14 mice can be used to determine where ztnfr14 is absolutely required in vivo. The phenotype of knockout mice is predictive of the in vivo effects of that a ztnfr14 antagonist, such as those described herein, may have. The human ztnfr14 cDNA can be used to isolate murine ztnfr14 mRNA, cDNA and genomic DNA, which are subsequently used to generate knockout mice. These mice may be employed to study the ztnfr14 gene and the protein encoded thereby in an in vivo system, and can be used as in vivo models for corresponding human diseases. Moreover, transgenic mice expression of ztnfr14 antisense polynucleotides or ribozymes directed against ztnfr14, described herein, can be used analogously to transgenic mice described above.

Another use for in vivo models includes delivery of an antigen challenge to the animal followed by administration of soluble ztnfr14 or its ligand, and measuring the T cell response, or the proliferation or decline of ztnfr14-expressing cells.

T-cell dependent and T-cell independent immune response can be measured as described in Perez-Melgosa et al., *J. Immunol.* 163: 1123-7, 1999.

Pharmacokinetic studies can be used in association with radiolabeled, soluble ztnfr14 polypeptides or fusions to determine the distribution and half life of such polypeptides in vivo. Additionally animal models can be used to determine the effects of soluble ztnfr14 on tumors and tumor development in vivo.

Also provided is the use of ztnfr14 polypeptides as surrogate markers for abnormal cell growth, especially, such growth as related to melanoma, neuroblastoma, and lymphoma. Patients having such diseases can be bled and ztnfr14 soluble receptors and its ligand can be detected in the blood.

ztnfr14 gene may be useful to as a probe to identify humans who have a defective ztnfr14 gene or to identify mutations which have occurred in its region of chromosome 1 as it includes many TNFR family members.

The polynucleotides of the present invention may also be used in conjunction with a regulatable promoter, thus allowing the dosage of delivered protein to be regulated.

Moreover, the activity and effect of ztnfr14 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Tumor models include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly M S, et al. *Cell* 79:315-328,1994). C57BL6/J mice are treated with an experimental agent either through daily injection of recombinant protein, agonist or antagonist or a one time injection of recombinant adenovirus. Three days following this treatment, $10^5$ to $10^6$ cells are implanted under the dorsal skin. Alternatively, the cells themselves may be infected with recombinant adenovirus, such as one expressing ztnfr14, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500-1800 $mm^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., ztnfr14, on the ability of the tumor to recruit vasculature and undergo metastasis can thus be assessed. In addition, aside from using adenovirus, the implanted cells can be transiently transfected with ztnfr14. Moreover, purified ztnfr14 or ztnfr14-conditioned media can be directly injected in to this mouse model, and hence be used in this system. Use of stable ztnfr14 transfectants as well as use of induceable promoters to activate ztnfr14 expression in vivo are known in the art and can be used in this system to assess ztnfr14 induction of metastasis. For general reference see, O'Reilly M S, et al. *Cell* 79:315-328, 1994; and Rusciano D, et al. Murine Models of Liver Metastasis. *Invasion Metastasis* 14:349-361, 1995.

Ztnfr14 polypeptides and antibodies may be used within diagnostic systems to detect the presence of its ligand polypeptides, such as a tumor necrosis factor ligand. The information derived from such detection methods would provide insight into the significance of ztnfr14 polypeptides in various diseases, and as a would serve as diagnostic tools for diseases for which altered levels of ztnfr14 are significant. Altered levels of ztnfr14 polypeptides may be indicative of pathological conditions including cancer, autoimmune disorders and infectious diseases.

In a basic assay, a single-stranded probe molecule is incubated with RNA, isolated from a biological sample, under conditions of temperature and ionic strength that promote base pairing between the probe and target ztnfr14 species. After separating unbound probe from hybridized molecules, the amount of hybrids is detected.

Well-established hybridization methods of RNA detection include northern analysis and dot/slot blot hybridization (see, for example, Ausubel ibid. and Wu et al. (eds.), "Analysis of Gene Expression at the RNA Level," in *Methods in Gene Biotechnology*, pages 225-239 (CRC Press, Inc. 1997)). Nucleic acid probes can be detectably labeled with radioisotopes such as $^{32}$P or $^{35}$S. Alternatively, ztnfr14 RNA can be detected with a nonradioactive hybridization method (see, for example, Isaac (ed.), *Protocols for Nucleic Acid Analysis by Nonradioactive Probes*, Humana Press, Inc., 1993). Typically, nonradioactive detection is achieved by enzymatic conversion of chromogenic or chemiluminescent substrates. Illustrative nonradioactive moieties include biotin, fluorescein, and digoxigenin.

ztnfr14 oligonucleotide probes are also useful for in vivo diagnosis. As an illustration, $^{18}$F-labeled oligonucleotides can be administered to a subject and visualized by positron emission tomography (Tavitian et al., *Nature Medicine* 4:467, 1998).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)). PCR primers can be designed to amplify a sequence encoding a particular ztnfr14 domain or motif, such as the ztnfr14 cysteine rich pseudo repeat.

One variation of PCR for diagnostic assays is reverse transcriptase-PCR (RT-PCR). In the RT-PCR technique, RNA is isolated from a biological sample, reverse transcribed to cDNA, and the cDNA is incubated with ztnfr14 primers (see, for example, Wu et al. (eds.), "Rapid Isolation of Specific cDNAs or Genes by PCR," in Methods in *Gene Biotechnology*, CRC Press, Inc., pages 15-28, 1997). PCR is then performed and the products are analyzed using standard techniques.

As an illustration, RNA is isolated from biological sample using, for example, the guanidinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or ztnfr14 anti-sense oligomers. Oligo-dT primers offer the advantage that various mRNA nucleotide sequences are amplified that can provide control target sequences. Ztnfr14 sequences are amplified by the polymerase chain reaction using two flanking oligonucleotide primers that are typically at least 5 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled ztnfr14 probe, and examined by autoradiography. Additional alternative approaches include the use of digoxigenin-labeled deoxyribonucleic acid triphosphates to provide chemiluminescence detection, and the C-TRAK colorimetric assay.

Another approach is real time quantitative PCR (Perkin-Elmer Cetus, Norwalk, Conn.). A fluorogenic probe, consisting of an oligonucleotide with both a reporter and a quencher dye attached, anneals specifically between the forward and reverse primers. Using the 5' endonuclease activity of Taq DNA polymerase, the reporter dye is separated from the quencher dye and a sequence-specific signal is generated and increases as amplification increases. The fluorescence intensity can be continuously monitored and quantified during the PCR reaction.

Another approach for detection of ztnfr14 expression is cycling probe technology (CPT), in which a single-stranded DNA target binds with an excess of DNA-RNA-DNA chimeric probe to form a complex, the RNA portion is cleaved with RNase H, and the presence of cleaved chimeric probe is detected (see, for example, Beggs et al., *J. Clin. Microbiol.* 34:2985, 1996 and Bekkaoui et al., *Biotechniques* 20:240, 1996). Alternative methods for detection of ztnfr14 sequences can utilize approaches such as nucleic acid sequence-based amplification (NASBA), cooperative amplification of templates by cross-hybridization (CATCH), and the ligase chain reaction (LCR) (see, for example, Marshall et al., U.S. Pat. No. 5,686,272 (1997), Dyer et al., *J. Virol. Methods* 60:161, 1996; Ehricht et al., *Eur. J. Biochem.* 243: 358, 1997 and Chadwick et al., *J. Virol. Methods* 70:59, 1998). Other standard methods are known to those of skill in the art.

Ztnfr14 probes and primers can also be used to detect and to localize ztnfr14 gene expression in tissue samples. Methods for such in situ hybridization are well-known to those of skill in the art (see, for example, Choo (ed.), *In Situ Hybridization Protocols*, Humana Press, Inc., 1994; Wu et al. (eds.), "Analysis of Cellular DNA or Abundance of mRNA by Radioactive In Situ Hybridization (RISH)," in *Methods in Gene Biotechnology*, CRC Press, Inc., pages 259-278, 1997 and Wu et al. (eds.), "Localization of DNA or Abundance of mRNA by Fluorescence In Situ Hybridization (RISH)," in *Methods in Gene Biotechnology*, CRC Press, Inc., pages 279-289, 1997).

Various additional diagnostic approaches are well-known to those of skill in the art (see, for example, Mathew (ed.), *Protocols in Human Molecular Genetics* Humana Press, Inc., 1991; Coleman and Tsongalis, *Molecular Diagnostics*, Humana Press, Inc., 1996 and Elles, *Molecular Diagnosis of Genetic Diseases*, Humana Press, Inc., 1996).

In addition, such polynucleotide probes could be used to hybridize to counterpart sequences on individual chromosomes. Chromosomal identification and/or mapping of the ztnfr14 gene could provide useful information about gene function and disease association. Many mapping techniques are available to one skilled in the art, for example, mapping somatic cell hybrids, and fluorescence in situ hybridization (FISH). A preferred method is radiation hybrid mapping. Radiation hybrid mapping is a somatic cell genetic technique developed for constructing high-resolution, contiguous maps of mammalian chromosomes (Cox et al., *Science* 250:245-50, 1990). Partial or full knowledge of a gene's sequence allows the designing of PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR based, chromosomal localizations and ordering of genes, sequence-tagged sites (STSs), and other non-polymorphic- and polymorphic markers within a region of interest. This includes establishing directly proportional physical distances between newly discovered genes of interest and previously mapped markers. The precise knowledge of a gene's position can be useful in a number of ways including: 1) determining if a sequence is part of an existing contig and obtaining additional surrounding genetic sequences in various forms such as YAC-, BAC- or cDNA clones, 2) providing a possible candidate gene for an inheritable disease which shows linkage to the same chromosomal region, and 3) for cross-referencing model organisms such as mouse which may be beneficial in helping to determine what function a particular gene might have.

The ztnfr14 polynucleotides of SEQ ID NO:2 have been mapped to chromosome 1q36.3. Thus, the present invention also provides reagents which will find use in diagnostic applications. For example, the ztnfr14 gene, a probe comprising ztnfr14 DNA or RNA or a subsequence thereof can be used to determine if the ztnfr14 gene is present on chromosome 1q36.3 or if a mutation has occurred. Detectable chromosomal aberrations at the ztnfr14 gene locus include, but are not limited to, aneuploidy, gene copy number changes, insertions, deletions, restriction site changes and rearrangements in this gene or the other six members of the TNFR family located in the locus. These aberrations can occur within the coding sequence, within introns, or within flanking sequences, including upstream promoter and regulatory regions, and may be manifested as physical alterations within a coding sequence or changes in gene expression level.

Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, *Chest* 108:255-65, 1995).

In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NOs:1 or 3, the complement of SEQ ID NOs:1 or 3, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5-16, 1991), ribonuclease protection assays, and other genetic linkage analysis techniques known in the art (Sambrook et al., ibid.; Ausubel et. al., ibid; Marian, *Chest* 108:255-65, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient's genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34-8, 1991).

Antisense methodology can be used to inhibit ztnfr14 gene transcription, such as to inhibit T cell development and interaction with other cells. Polynucleotides that are complementary to a segment of a ztnfr14-encoding polynucleotide (e.g.; a polynucleotide as set forth in SEQ ID NOs:2, 27, or 38) are designed to bind to ztnfr14-encoding mRNA and to inhibit translation of such mRNA. Such antisense polynucleotides are used to inhibit expression of ztnfr14 polypeptide-encoding genes in cell culture or in a subject.

Additionally, polynucleotides of the present invention can be used as a marker for the X chromosome. Diseases which map to the 1q36.3 include those associated with the six other TNFR members at this location.

The polypeptides of ztnfr14 may represent an antigenic marker for neuroblastoma, melanoma, or lymphoma, as well as tumors of the stomach and uterus. Thus, these polypeptides, or fragments thereof may be useful as antigens to produce humanized antibodies for treatment of these specific tumors. Additionally, these polypeptides and polypeptide fragments can be useful to generate vaccines for use cancer therapy.

For pharmaceutical use, the proteins of the present invention can be administered intravaginally, orally, rectally, parenterally (particularly intravenous or subcutaneous), intracisternally, intraperitoneally, topically (as douches, powders, ointments, drops or transdermal patch) bucally, or as a pulmonary or nasal inhalant. Intravenous administration will be by bolus injection or infusion over a typical period of one to several hours. In general, pharmaceutical formulations will include a ztnfr14 protein, alone, or in conjunction with a dimeric partner, in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc.

Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 µg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of ztnfr14 is an amount sufficient to produce a clinically significant change in, tumor suppression, apoptosis, myogenesis, inflammation, and infection in tissues of the uterus, lung carcinoma and breast carcinoma, as well as in cells of melanoma, osteosarcoma, and lymphoma. Similarly, a therapeutically effective amount of ztnfr14 is an amount sufficient to produce a clinically significant change in disorders associated with tissues of the stomach, uterus, melanoma, neuroblastoma, and lymphoma.

The invention is further illustrated by the following non-limiting examples.

EXAMPLES

Example 1

Extension of EST Sequence

The novel ztnfr14 polypeptide-encoding polynucleotides of the present invention were initially identified by querying a database of partial sequences. A partial sequence was identified in stomach, uterus, and cancer cDNA libraries. The polynucleotide sequence (SEQ ID NO:1) of the insert corresponding to the cDNA clone was sequenced. The deduced amino acid sequence of the insert was determined to be full-length and is shown in SEQ ID NO:2. Screening of additional ESTs provided the partial sequences for the two splice variants, ztnfr14x2 (SEQ ID NO:29) and ztnfr14x3 (SEQ ID NO:31). These polynucleotides, and the polypeptides encoding them, were identified as a novel member of the tumor necrosis factor receptor family, ztnfr14.

Example 2

Tissue Distribution

Human Multiple Tissue Northern Blots (MTN I, MTN II and MTN III; Human Cancer Cell Line; Human Immune Blot; Clontech, In-house human lymphocyte subset blot; Clontech, Palo Alto, Calif.) are probed to determine the tissue distribution of human ztnfr14 expression. A probe is amplified as a template and appropriate oligonucleotides are prepared as primers. The amplification is carried out as follows: 1 cycle at 94° C. for 1.5 minutes, 35 cycles of 94° C. for 15 seconds and 60° C. for 30 followed by one cycle at 72° C. for 10 minutes. The PCR products are visualized by agarose gel electrophoresis and is purified using a Gel Extraction Kit (Qiagen, Chatsworth, Calif.) according to manufacturer's instructions. The probe is radioactively labeled using the MULTIPRIME DNA labeling kit (Amersham, Arlington Heights, Ill.) according to the manufacturer's instructions. The probe is purified using a NUCTRAP push column (Stratagene). EXPRESSHYB (Clontech) solution is used for pre-hybridization and as a hybridizing solution for the Northern blots. Hybridization takes place overnight at 65° C. using $1 \times 10^6$ cpm/ml of labeled probe. The blots are then washed four times in 2×SSC and 0.1% SDS at RT, followed by 2 washes in 0.1×SSC and 0.1% SDS at 55° C.

Example 3

Chromosomal Assignment and Placement of ztnfr14 ztnfr14 is mapped to human chromosome 1 using the commercially available version of the "Stanford G3 Radiation Hybrid Mapping Panel" (Research Genetics, Inc., Huntsville, Ala.). The "Stanford G3 RH Panel" contains PCRable DNAs from each of 83 radiation hybrid clones of the whole human genome, plus two control DNAs (the RM donor and the A3 recipient). A publicly available WWW server (http://shgc-www.stanford.edu) allows chromosomal localization of markers.

For the mapping of ztnfr14 with the "Stanford G3 RH Panel", 20 µl reactions is set up in a 96-well microtiter plate (Stratagene, La Jolla, Calif.) and uses a "RoboCycler Gradient 96" thermal cycler (Stratagene). Each of the 85 PCR reactions consists of 2 µl 10× KlenTaq PCR reaction buffer (CLONTECH Laboratories, Inc., Palo Alto, Calif.), 1.6 µl dNTPs mix (2.5 mM each, PERKIN-ELMER, Foster City, Calif.), 1 µl sense primer, ZC 25352 (SEQ ID NO:14), 1 µl antisense primer, ZC 25353 (SEQ ID NO:15), 2 µl "Redi-Load" (Research Genetics, Inc., Huntsville, Ala.), 0.4 µl 50× Advantage KlenTaq Polymerase Mix (Clontech Laboratories, Inc.), 25 ng of DNA from an individual hybrid clone or control and x µl ddH2O for a total volume of 20 µl. The reactions are overlaid with an equal amount of mineral oil and sealed. The PCR cycler conditions are as follows: an initial 1 cycle 5 minute denaturation at 94° C., 35 cycles of a 45 seconds denaturation at 94° C., 45 seconds annealing at 64° C. and 1 minute AND 15 seconds extension at 72° C., followed by a final 1 cycle extension of 7 minutes at 72° C. The reactions are separated by electrophoresis on a 2% agarose gel.

The results show linkage of ztnfr14 to the human chromosome 1 framework marker. The use of surrounding genes/markers positions ztnfr14 in the 1q36.3 chromosomal region.

Example 4

Construction of Mammalian Soluble ztnfr14 Expression Vectors: ztnfr14sR/CEE and ztnfr14sR/Fc4

An expression vector is prepared to express the soluble ztnfr14 polypeptide (ztnfr14sR) fused to a C-terminal Glu-Glu tag (SEQ ID NO:36).

A PCR generated ztnfr14 DNA fragment is created using appropriate oligonucleotides as PCR primers to add suitable restriction sites at 5' and 3' ends of the soluble ztnfr14 DNA, respectively. A plasmid containing the ztnfr14 cDNA (SEQ ID NO:1) was used as a template. PCR amplification of the ztnfr14 fragment is performed as follows: One cycle at 94° C. for 1 minute; 25 cycles at 94° C. for 30 seconds, 68° C. for seconds, followed by an additional 68° C. incubation for 4 minutes, and hold at 10° C. The reaction is purified by chloroform/phenol extraction and isopropanol precipitation, and digested with the selected restriction endonucleases (Boehringer Mannheim, Indianapolis, Ind.). A band of the appropriate length is visualized by 1% agarose gel electrophoresis, excised, and the DNA was purified using a QiaexII™ purification kit (Qiagen, Valencia, Calif.) according to the manufacturer's instruction.

About 30 ng of the restriction digested ztnfr14sR insert and about 10 ng of an appropriate digested expression vector is ligated at room temperature for 2 hours. One microliter of ligation reaction is electroporated into DH10B competent cells (Gibco BRL, Rockville, Md.) according to manufacturer's direction and plated onto LB plates containing 50 mg/ml ampicillin, and incubated overnight. Colonies are screened by restriction analysis of DNA, which is prepared from 2 ml liquid cultures of individual colonies. The insert sequence of positive clones is verified by sequence analysis. Thus, the excised ztnfr14sR DNA is subcloned into the appropriate expression vector. A large-scale plasmid preparation is done using a Qiagen® Mega prep kit (Qiagen) according to manufacturer's instruction.

The same process was used to prepare the ztnfr14 soluble receptor with a C-terminal Fc4 tag (SEQ ID NO:37), creating the ztnfr14sR/Fc4. To prepare ztnfr14sR/Fc4, the expression vector has a Fc4 tag in place of the Glu-Glu tag. Fc4 is the Fc region derived from human IgG, which contains a mutation so that it no longer binds the Fc receptor. Although Fc4 is utilized in the present example, one of ordinary skill recognizes that other Fc constructs (i.e., those derived from other Ig molecules) can be used to prepare a soluble ztnfr14 receptor utilizing this same protocol.

Example 5

Transfection and Expression of ztnfr14 Soluble Receptor Polypeptides

The day before the transfection, BHK 570 cells (ATCC No. CRL-10314; ATCC, Manasas, Va.) are plated in a 10-cm plate with 50% confluence in normal BHK DMEM (Gibco/BRL High Glucose) media. The day of the transfection, the cells are washed once with Serum Free (SF) DMEM, followed by transfection with the ztnfr14sR/Fc4 or ztnfr14sR/CEE expression plasmids. Sixteen micrograms of each DNA construct are separately diluted into a total final volume of 640 µl SF DMEM. A diluted LipofectAMINE™ mixture (35 µl LipofectAMINE™ in 605 µl SF meida) is added to the DNA mix, and incubated for 30 minutes at room temperature. Five milliliters of SF media is added to the DNA/LipofectAMINE™ mixture, which is then added to BHK cells. The cells are incubated at 37° C./5% $CO_2$ for 5 hours, after which 6.4 ml of BHK media with 10% FBS is added. The cells are incubated overnight at 37° C./5% $CO_2$.

Approximately 24 hours post-transfection, the BHK cells are split into selection media with 1 uM methotrexate (MTX). The cells are repeatedly split in this manner until stable ztnfr14sR/CEE and ztnfr14sR/Fc4 cell lines are identified. To detect the expression level of the ztnfr14 soluble receptor fusion proteins, the BHK cells are washed with PBS and incubated in SF media for 72 hours. The SF condition media is collected and 20 µl of the sample is run on 10% SDS-PAGE gel under reduced conditions. The protein bands are transferred to nitrocellulose filter by Western blot, and the fusion proteins are detected using either goat-anti-human IgG/HRP conjugates for the ztnfr14sR/Fc4 fusion or mouse-anti-Glu-Glu tag/HRP conjugates for the ztnfr14sR/CEE fusion. Expression vectors containing a different soluble receptor fused to the Fc4 or the CEE tags are used as controls.

Transfected BHK cells are transferred into T-162 flasks. Once the BHK cells reached about 80% confluence, they are washed with PBS and incubated in 100 ml SF media for 72 hours, and then the condition media is collected for protein purification.

Example 6

Purification and Analysis of ztnfr14sR/CEE

Recombinant carboxyl terminal Glu-Glu tagged ztnfr14sR is produced from transfected BHK cells as described in Example 5 above. About six liters of conditioned media are harvested from 60 dishes after roughly 72 hours incubation. A portion of the media is sterile filtered using filtration units from different manufactures. The Nalgene 0.2 µm and 0.45 µm filters, and Millipore Express 0.22 µm filter are compared and the one providing the best recovery of the protein and flow rate is used. The level of protein expression reaches the optimal concentration after about 72 hours in new media. Three harvests of the ztnfr14sR/CEE conditioned media are collected.

Protein is purified from the filtered media by a combination of Anti-Glu-Glu (Anti-EE) peptide antibody affinity chromatography and S-100 gel exclusion chromatography. Culture medium is directly loaded onto a 20×185 mm (58-ml bed volume) anti-EE antibody affinity column at a flow of about 4 ml/minute. Following column washing with ten column volumes of PBS, bound protein is eluted with two column volumes of 0.4 mg/ml EYMPTD peptide (Princeton Biomolecules, N.J.). Fractions of 5 ml were collected. Samples from the anti-EE antibody affinity column are analyzed by SDS-PAGE with silver staining and western blotting for the presence of ztnfr14sR/CEE. Fractions containing the ztnfr14sR/CEE protein are pooled and concentrated to 4 mls using Biomax-5 concentrator (Millipore), and loaded onto a 16×1000 mm Sephacryl S-100 HR gel filtration column (Amersham Pharmacia Biotech). The fractions containing purified ztnfr14sR/CEE are pooled, filtered through 0.2 µm filter, aliquoted into 100 µl each, and frozen at −80° C. The concentration of the final purified protein is determined by BCA assay (Pierce) and HPLC-amino acid analysis.

Recombinant ztnfr14sR/CEE is analyzed by SDS-PAGE (Nupage 4-12%), Novex) with either coomassie and silver staining method (Fast Silver, Geno Tech), and Western blotting using monoclonal anti-EE antibody. Either the conditioned media or purified protein is electrophoresed using a Novex's Xcell II mini-cell (San Diego, Calif.) and transferred to nitrocellulose (0.2 µm; Bio-Rad Laboratories, Hercules, Calif.) at room temperature using Novex's Xcell II blot module with stirring according to directions provided in the instrument manual. The transfer is run at 500 mA for one hour in a buffer containing 25 mM Tris base, 200 mM glycine, and 20% methanol. The filters are then blocked with 10% non-fat dry milk in PBS for 10 minutes at room temperature. The nitrocellulose is quickly rinsed, then primary antibody is added in PBS containing 2.5% non-fat dry milk. The blots are incubated for two hours at room temperature or overnight at 4° C. with gentle shaking. Following the incubation, blots are washed three times for 10 minutes each in PBS. Secondary antibody (goat anti-mouse IgG conjugated to horseradish peroxidase; obtained from Rockland Inc., Gilbertsville, Pa.) diluted 1:2000 in PBS containing 2.5% non-fat dry milk is added, and the blots are incubated for two hours at room temperature with gentle shaking. The blots are then washed three times, 10 minutes each, in PBS, then quickly rinsed in $H_2O$. The blots are developed using commercially available chemiluminescent substrate reagents (SuperSignal® ULTRA reagents 1 and 2 mixed 1:1; reagents obtained from Pierce Chemical Co.), and the signal is captured using Lumi-Imager's Lumi Analyst 3.0 software (Boehringer Mannheim GmbH, Germany) for exposure times ranging from 10 second to 5 minutes or as necessary.

Example 7

Purification and Analysis of ztnfr14sR/Fc4

Recombinant carboxyl terminal Fc4 tagged ztnfr14sR is produced from transfected BHK cells as described in Example 5 above. Approximately five-liters of conditioned media were harvested from 60 dishes after about 72 hours of incubation. A portion of the media was sterile filtered using filtration units from different manufactures. The Nalgene 0.2 μm and 0.45 μm filters, Millipore Express 0.22 μm filter, and Durapore 0.45 μm filter are compared and the one providing the best yield and flow rate is used. The level of protein expression reaches the optimal concentration after about 72 hours in the new media. Normally three to four harvests of the media were collected.

Protein is purified from the filtered media by a combination of Poros 50 protein A affinity chromatography (PerSeptive Biosystems, 1-5559-01, Framingham, Mass.) and S-200 gel exclusion chromatography column (Amersham Pharmacia Biotech). Culture medium is directly loaded onto a 10×80 mm (6.2-ml bed volume) protein A affinity column at a flow of about 4 ml/minute. Following column washing for ten column volumes of PBS, bound protein is eluted by five column volumes of 0.1 M glycine, pH 3.0 at 10 ml/minute). Fractions of 1.5 ml each are collected into tubes containing 38 μl of 2.0 M Tris, pH 8.8, in order to neutralize the eluted proteins. Samples from the affinity column are analyzed by SDS-PAGE with Coomassie staining and Western blotting for the presence of ztnfr14sR/Fc4 using human IgG-HRP. Ztnfr14sR/Fc4-containing fractions are pooled and concentrated to 4 mls using Biomax-30 concentrator (Millipore), and loaded onto a 16×1000 mm Sephacryl S-200 HR gel filtration. The fractions containing purified ztnfr14sR/Fc4 were pooled, filtered through 0.2 μm filter, aliquoted into 100, 200 and 500 μl each, and frozen at −80° C. The concentration of the final purified protein is determined by BCA assay (Pierce) and HPLC-amino acid analysis.

Recombinant ztnfr14sR/Fc4 is analyzed by SDS-PAGE (Nupage 4-12%, Novex) with coomassie staining method and Western blotting using human IgG-HRP. Either the conditioned media or purified protein is electrophoresed using a Novex's Xcell II mini-cell (San Diego, Calif.) and transferred to nitrocellulose (0.2 μm; Bio-Rad Laboratories, Hercules, Calif.) at room temperature using Novex's Xcell II blot module with stirring according to directions provided in the instrument manual. The transfer is run at 500 mA for one hour in a buffer containing 25 mM Tris base, 200 mM glycine, and 20% methanol. The filters are then blocked with 10% non-fat dry milk in PBS for 10 minutes at room temperature. The nitrocellulose is quickly rinsed, then the human Ig-HRP antibody (1:2000) is added in PBS containing 2.5% non-fat dry milk. The blots are incubated for two hours at room temperature, or overnight at 4° C., with gentle shaking. Following the incubation, the blots are washed three times for 10 minutes each in PBS, then quickly rinsed in $H_2O$. The blots are developed using commercially available chemiluminescent substrate reagents (SuperSignal® ULTRA reagents 1 and 2 mixed 1:1; reagents obtained from Pierce Chemical Co.), and the signal is captured using Lumi-Imager's Lumi Analyst 3.0 software (Boehringer Mannheim GmbH, Germany) for exposure times ranging from 10 second to 5 minutes or as necessary.

Example 8

Identification of Cells Expressing ztnfr14 Using In Situ Hybridization

Specific human tissues are isolated and screened for ztnfr14 expression by in situ hybridization. Various human tissues prepared, sectioned and subjected to in situ hybridization includes normal stomach, normal uterus, neuroblastomas and melanoma, among other cancers. The tissues are fixed in 10% buffered formalin and blocked in paraffin using standard techniques. Tissues are sectioned at 4 to 8 microns. Tissues are prepared using a standard protocol ("Development of non-isotopic in situ hybridization" at http://dir.niehs.nih.gov/dirlep/ish.html). Briefly, tissue sections are deparaffinized with HistoClear (National Diagnostics, Atlanta, Ga.) and then dehydrated with ethanol. Next they are digested with Proteinase K (50 μg/ml) (Boehringer Diagnostics, Indianapolis, Ind.) at 37° C. for 2 to 20 minutes. This step is followed by acetylation and re-hydration of the tissues.

Two in situ probes generated by PCR are designed against the human ztnfr14 sequence. Two sets of oligos are designed to generate probes for separate regions of the ztnfr14 cDNA. The antisense oligo from each set also contains the working sequence for the T7 RNA polymerase promoter to allow for easy transcription of antisense RNA probes from these PCR products. The PCR reaction conditions are as follows: 2 cycles at 95° C. for 30 sec, 50° C. for 1 min, 72° C. for 1 min followed by cycles of 95° C. for 30 sec, 72° C. for 2 min. Probes are subsequently labeled with digoxigenin (Boehringer) or biotin (Boehringer) using an In Vitro transcription System (Promega, Madison, Wis.) as per manufacturer's instruction.

In situ hybridization is performed with a digoxigenin- or biotin-labeled ztnfr14 probe (above). The probe is added to the slides at a concentration of 1 to 5 pmol/ml for 12 to 16 hours at 60° C. Slides are subsequently washed in 2×SSC and 0.1×SSC at 55° C. The signals are amplified using tyramide signal amplification (TSA) (TSA, in situ indirect kit; NEN) and visualized with Vector Red substrate kit (Vector Lab) as per manufacturer's instructions. The slides are then counterstained with hematoxylin (Vector Laboratories, Burlingame, Calif.).

Example 9

Human ztnfr14 Polyclonal Antibodies

Polyclonal antibodies are prepared by immunizing 2 female New Zealand white rabbits with the purified recombinant protein ztnfr14-CEE protein expressed in BHK from Example 6. The rabbits are each given an initial intraperitoneal (ip) injection of 200 μg of purified protein in Complete Freund's Adjuvant followed by booster ip injections of 100 μg peptide in Incomplete Freund's Adjuvant every three weeks. Seven to ten days after the administration of the second booster injection (3 total injections), the animals are bled and the serum is collected. The animals are then boosted and bled every three weeks.

The ztnfr14sR-specific polyclonal antibodies are affinity purified from the rabbit serum using a CNBr-SEPHAROSE 4B protein column (Pharmacia LKB) that is prepared using 10 mg of purified recombinant huztnfr14-Fc protein (as prepared in Example 6) per gram of CNBr-SEPHAROSE, followed by 20× dialysis in PBS overnight. Ztnfr14sR-specific antibodies are characterized by ELISA using 1 μg/ml of the specific purified recombinant huztnfr14-CEE-BHK protein as antibody target.

Example 10

Human ztnfr14 Northern

An appropriate probe is made by PCR using plasmid DNA containing SEQ ID NO: 1 as a template and suitable oligonucleotides as primers. The amplification is carried out as follows: 1 cycle at 94° C. for 1 minutes, 35 cycles of 94° C. for 30 seconds, 55° C. for 30 seconds and 72° C. for 30 seconds, followed by 1 cycle at 72° C. for 10 minutes. The PCR products are visualized by agarose gel electrophoresis and the probe was purified using a Gel Extraction Kit (Qiagen, Chatsworth, Calif.) according to manufacturer's instructions. The probe is radioactively labeled using the REDIPRIME DNA labeling kit (Amersham, Arlington Heights, Ill.) according to the manufacturer's instructions. The probe is purified using a NUCTRAP push column (Stratagene).

An in-house blot containing poly A+RNA from at least human normal stomach, human normal uterus and human neuroblastoma cells lines and human melanoma cell lines such as C32, Malme 3M, SK-MEL-2, and WM-115 is prehybridized in EXPRESSHYB (Clontech) for 3 hours at 65° C. Hybridization takes place overnight at 65° C. using $10^6$ cpm/ml of labeled probe. The blots are then washed four times in 2×SSC and 0.1% SDS at room temp, followed by 2 washes in 0.1×SSC and 0.1% SDS at 50° C.

Example 11

Human ztnfr14 Tumor Polymerase Chain Reaction

A nested 5' RACE reaction was performed using marathon cDNAs from a neuroblastoma cell line, a melanoma cell line and lymphoma cell lines. A 50 ul PCR reaction is run under the following conditions: 20 pmol of a sense primer corresponding to the vector sequence and 20 pmol of an antisense primer corresponding to the polynucleotide sequence as shown in SEQ ID NO:1. The experiment is performed using a 3-step, 2-temperature reaction including an initial one minute at 94° C. followed by 5 cycles of 94° C. for 30 seconds and 72° C. for 5 minutes, then 5 cycles of 94° C. for 30 seconds and 70° C. for 5 minutes, then 25 cycles of 94° C. for 30 seconds and 68° C. for 5 minutes. A final extension of 72° C. for 10 min completes the reaction. One ul of a 1:50 dilution of the above reactions is used for nested 5' RACE using 20 pmol of an nested sense primer corresponding to the vector sequence and 20 pmol of an antisense primer for a second section of SEQ ID NO: 1. A 50 μl reaction is set up and ran under the following conditions. An initial one minute at 94° C. is followed by 4 cycles of 94° C. for 30 seconds and 72° C. for 5 minutes, then 4 cycles of 94° C. for 30 seconds and 70° C. for 5 minutes, then 20 cycles of 94° C. for 30 seconds and 68° C. for 5 minutes.

These PCR bands were excised, purified using a Qiagen gel extraction kit and subcloned into the pCR 2.1 TOPO vector (Invitrogen, San Diego, Calif.). The resulting nucleotide sequence of the clone containing the 552 bp band (upper) is shown in SEQ ID NO: 33, which corresponds to the 175 residue amino acid sequence as shown in SEQ ID NO:34. A composite of the polypeptide sequence of SEQ ID NO:2 with SEQ ID NO:34 results in a 299 residue protein shown in SEQ ID NO:35. This variant of ztnfr14 differs from the polypeptide sequence as shown in SEQ ID NO:2 by a two amino acid insertion (Val-Ala) at residue 172 and a 28 residue insertion at residue 204 relative to the corresponding region of SEQ ID NO:2.

The resulting nucleotide sequence for the clone containing the 431 bp band (lower) is shown in SEQ ID NO:36, which corresponds to the 142 residue amino acid sequence shown in SEQ ID NO:37. A composite of the polypeptide sequence of SEQ ID NO:2 with SEQ ID NO:37 results in a 173 residue protein shown in SEQ ID NO:38. This variant of ztnfr14 differs from the polypeptide sequence as shown in SEQ ID NO:2 by a translation stop codon resulting in a truncated soluble ztnfr14 receptor.

Example 12

Construction of an Assay Cell Line

A BaF3 assay cell line is constructed for ztnfr14 ligand cloning. A ztnfr14/TNFR1 chimera is built in which the transmembrane and cytoplasmic domain of ztnfr14 are replaced by those of the TNFα receptor (TNFR1) (SEQ ID NO:38). The ztnfr14/TNFR1 chimera was transfected into a BaF3 cell line that contains a KZ159/mIL4 reporter gene (SEQ ID NO:39). KZ159/mIL4 responds to the activation of TNFR1 receptor by TNFα, triggering the expression and secretion of mIL4 that leads to the proliferation of BaF3 cells.

The extracellular domain of ztnfr14 is amplified with appropriate PCR primers using ztnfr14 full-length cDNA as a template. The PCR reaction is as follows: 20 cycles of 94° C. for 30 sec and 68° C. for 2 min, then four more min at 68° C. and soak at 10C. The transmembrane and cytoplasmic domain of mouse TNFR1 is amplified with appropriate PCR primers using mouse placenta marathon cDNA as a template. The PCR reaction is as follows: 35 cycles of 94° C. for 30 sec and 68° C. for 2 min, then four more min at 68° C. and soak at 10° C. The PCR products were separated on 1% Agarose, the ztnfr14 and TNFR1 bands are excised and the DNA is purified using a QiaexII™ purification kit (Qiagen, Valencia, Calif.) according to the manufacturer's instruction.

The pZP7Z plasmid is a mammalian expression vector containing an expression cassette having the CMV promoter and a human growth hormone terminator. The plasmid also has an E. coli origin of replication, a mammalian selectable marker expression unit having an SV40 promoter, an enhancer and an origin of replication, as well as a Zeocin resistant gene, and SV40 terminator. About 30 ng of the restriction digested ztnfr14 insert and TNFR1 insert and about 10 ng of the digested vector are ligated at 11° C. overnight. One microliter of ligation reaction is electroporated into DH10B competent cells (Gibco BRL, Rockville, Md.) according to manufacturer's direction and plated onto LB plates containing 50 ug/ml ampicillin, and incubated overnight. Colonies are screened by restriction analysis of DNA, which is prepared from 2 ml liquid cultures of individual colonies. The insert sequence of positive clones is verified by sequencing analysis.

Ten million BaF3 cells that contain KZ159/mIL4 reporter are transfected with ztnfr14/TNFR1/pZP7Z plasmid by electroporation, and selected for Zeocin resistant stable transfectants. The proliferation of this stable cell line in response to TNFα without mIL-3 was assayed, and the activation of ztnfr14/TNFR1 chimera is tested using cross-linked antiztnfr14 reagent which is prepared by incubating rabbit antiztnfr14 antibody at 1 ug/ml with anti-rabbit immunoglobulin G (IgG) antibody-coupled magnetic beads. The positive clones are then used as an assay cell line to confirm the binding of the ztnfr14 ligand to the ztnfr14 extracellular domain.

Example 13

Construction of a Transgenic Plasmid

Twenty μg of the pzp9 plasmid containing the ztnfr14-Fc4 soluble receptor sequence from Example 5 was digested with appropriate restriction endonucleases. The ztnfr14-Fc4 soluble receptor fragment is then isolated by running the digested vector on a 1.2% SeaPlaque GTG® gel and excising the fragment. DNA is purified using the QiaQuick™ (Qiagen) gel extraction kit. The EcoRI and XbaI overhangs were then converted to blunt ends using Kienow polymerase.

The ztnfr14-Fc4 soluble receptor fragment is then ligated into a apoA1 C1-17 transgenic vector, which was previously digested with an appropriate restriction enzyme. The apoA1 C1-17 plasmid is designed for expression of a gene of interest in transgenic mice. It contains an expression cassette comprised of the apoA1 promoter, the first apoA1 exon and a portion of the first intron, the ztnfr14-Fc4 coding sequence, a polylinker for the insertion of the desired clone and the human growth hormone poly A sequence.

About one microliter of the ligation reaction is electroporated into DH10B ElectroMax® competent cells (GIBCO BRL) according to manufacturer's direction, plated onto LB plates containing 100 μg/ml ampicillin, and incubated overnight at 37° C. Colonies are picked and grown in LB media containing 100 μg/ml ampicillin. Miniprep DNA is prepared from the picked clones and screened for the correctly oriented ztnfr14-Fc4 soluble receptor insert by restriction digestion analysis and subsequent agarose gel electrophoresis. Maxipreps of the correct apoA1 C1-17 ztnfr14-Fc4 soluble receptor construct are performed.

An appropriate fragment containing the expression cassette is prepared and used for microinjection into fertilized murine oocytes.

Example 14

Differential Expression of ztnfr14 in Immune Cells

Initial experiments concerning expression of ztnfr14 in various cell lines were preformed using a preliminary PCR analysis. The results of this experiment indicated that ztnfr14 is expressed preferentially in a number of immune cell lines including those characterized as B cell, NK cell, and T cell lines. Among the specific cell lines that are ztnfr14(+) are Granta 519, ARH-77, Ramos, Raji, CCRF-CEM, MV-4-11, and HS Sultan. These results suggested that a more quantitative PCR analysis should be used to compare the amount of ztnfr14 in resting and activated human cell lines.

Total mRNA was isolated from resting and activated human cell lines as follows. Pellets were prepared using RNeasy Midiprep Kit (Qiagen, Valencia, Calif.) per the manufacturer's instructions. Real Time-PCR was performed on these human mRNA samples as described below with measurements designed to assess levels of human zTNFR14x1, zTNFR14x2 and zTNFR14x3 expression.

Primers and Probes for Quantitative RT-PCR

Real-time quantitative RT-PCR using the ABI PRISM 7700 Sequence Detection System (PE Applied Biosystems, Inc., Foster City, Calif.) has been previously described (See, Heid, C. A. et al., Genome Research 6:986-994, 1996; Gibson, U. E. M. et al., Genome Research 6:995-1001, 1996; Sundaresan, S. et al., Endocrinology 139:4756-4764, 1998). This method incorporates use of a gene specific probe containing both reporter and quencher fluorescent dyes. When the probe is intact the reporter dye emission is negated due to the close proximity of the quencher dye. During PCR extension using additional gene-specific forward and reverse primers, the probe is cleaved by 5' nuclease activity of Taq polymerase. This cleavage releases the reporter dye from the probe, resulting in a measurable increase in fluorescent emission.

Three sets of primers and probes were generated for use in real-time quantitative RT-PCR and each was designed to specifically amplify either zTNFR14×1 or zTNFR14×2 or zTNFR14×3. The forward primer for human zTNFR14×1, zc49573 (SEQ ID NO:40) (5'CTGGCGAAGCCGCTGC) was used at 200 nM and the reverse primer, zc49579 (SEQ ID NO:41) (5'GATCCGTGGCCCTGTCCAGG) was used at 800 nM concentration to synthesize a 67 bp product. The forward primer for human zTNFR14×2, zc49277 (SEQ ID NO:42) (5'AGAAGAAACAAAGCTCCGGCCCTG-CAGCC) and the reverse primer, zc49280 (SEQ ID NO:43) (5'CCCAGCACCACTGAAGCGATGGCT) were both used at 800 nM concentration to synthesize a 141 bp product. The forward primer for human zTNFR14×3, zc49284 (SEQ ID NO:44) (5'CAAAGGGCCGGCCCCCGCA) and the reverse primer, zc49233 (SEQ ID NO:45) (5'GAAAAG-GAGAGAAAGGCAGAGTGA) were both used at 400 nM concentration to synthesize a 179 bp product. The corresponding TaqMan probe for zTNFR14×1, ZG49714 (SEQ ID NO:46) (5'AGTCCTCAGTACGGAAGC) was used at 200 mM. The corresponding TaqMan probe for zTNFR14×2, ZG49360 (SEQ ID NO:47) (5'CCACCCGAGGACAGACG-CAGCCG) was also used at 200 nM. The corresponding TaqMan probe for zTNFR14×3, ZG48404 (SEQ ID NO:48) (5'CCTGGCCGCGTGTGCCTGGT) was used at 100 nM. These three Taqman probes were synthesized in-house using standard probe synthesis procedures. The probes were labeled with a reporter fluorescent dye (6-carboxyfluorescein) (FAM) (Glen Research, Sterling, Va.) at the 5'end and a non-fluorescent quencher (ECLIPSE) (Epoch Biosciences, Bothell, Wash.) at the 3' end.

As a control to test the integrity and quality of RNA samples tested, all RNA samples were screened for either rRNA and the human form of the housekeeping gene Glucouronidase (hGUS) using primer and probe sets either ordered from PE Applied Biosystems (rRNA kit Catalog No. 4304483) or designed in-house (hGUS) using standard primer, probe protocols. The rRNA kit contains the forward primer, the rRNA reverse primer, and the rRNA TaqMan® probe. The rRNA probe was labeled at the 5'end with a reporter fluorescent dye VIC (PE Applied Biosystems, Foster City, Calif.) and at the 3' end with the quencher fluorescent dye TAMRA (PE Applied Biosystems, Foster City, Calif.) as per manfacturer's instructions. The hGUS primers and probe were used in each PCR reaction at 200 nM and 100 nM respectively. The forward primer is zc40574 (SEQ ID NO:#49) (5'CTCATTTGGAATTTTGCCGATT) and the reverse primer was zc40575 (SEQ ID NO:50) (5' CCGAGT-GAAGATCCCCTTTTA.

The hGUS probe zc43228 (SEQ ID NO:51) (5' TGAA-CAGTCACCGACGAGAGTGCTGG) was labeled at the 5'end with a reporter fluorescent dye Yakima Yellow (Epoch Biosciences, Bothell, Wash.) and at the 3'end with a non-fluorescent quencher dye (ECLIPSE) (Epoch Biosciences, Bothell, Wash.). The rRNA and hGUS results also serve as an endogenous control and allow for the normalization of the zTNFR14×1, zTNFR14×2 zTNFR14×3 mRNA expression results seen in the test samples.

Real-Time Quantitative RT-PCR

Relative levels of human zTNFR14×1, zTNFR14×2 zTNFR14×3 mRNA were determined by analysis of total RNA samples using RT-PCR. The total RNA samples were analyzed in triplicate for transcript levels of each human zTNFR14 mRNA splice variant, zTNFR14×1, zTNFR14×2, and zTNFR14×3 and for levels of hGUS as an endogenous control. In a total volume of 10 μl, each RNA sample was subjected to an RT-PCR reaction containing: approximately 70 ng of total RNA in ABsolute QPCR dUTP Mix (Abgene, Rochester, N.Y., Product No. AB-1140/B) (a proprietary mix of DNA polymerase, salt and dNTPs) diluted to 1×; the internal standard dye, carboxy-x-rhodamine (ROX)); appropriate primers and probes at concentrations described above; and rMoMuLV reverse transcriptase (0.25 U/μl)(PE Applied Biosystems, Foster City, Calif., Product No. 4311235). PCR thermal cycling conditions were as follows: an initial reverse transcription (RT) step of one cycle at 50° C. for 20 minutes; followed by a DNA polymerase activation step of one cycle at 95° C. for 10 minutes; followed by 40 cycles of amplification at 95° C. for 15 seconds and 60° C. for 1 minute.

TaqMan RT-PCR was used to assess human zTNFR14×1, zTNFR14×2 and zTNFR14×3 mRNA expression in unstimulated human B cell lines (DOHH-2, Granta519, REH, Ramos, WSU-NHL, CESS, BJAB, RPMI1788, OMP-2, HS Sultan, 697, L363, RPMI8226, U266, ARH77, Raji), in unstimulated human T cell lines (HUT78, CCRF-CEM), a transformed bone marrow endothelial cell line (TRBMEC), in unstimulated human monocyte lines (K652, KG-1, HEL 92.1.7, MV4-11), unstimulated dendritic cells (DC), in a mixed lymphocyte reaction (two donors, one irradiated) (MLR), both with and without interferon gamma (IFNg) and fibroblasts. Expression was also assessed in resting and activated human monocyte lines (HL-60, THP-1, U937). Activation was achieved by various standard means including addition of stimulating factors such as dimethyl sulfoxide (DMSO, with RNA from various sources, abbreviated CGAT and MKMA), 12-myristate 13-acetate (PMA with and without ionomycin), vitamin $D_3$, retinoic acid, butyric acid, lipolysaccharide (LPS, with or without WNg), as is well known in the art.

Figure 5:
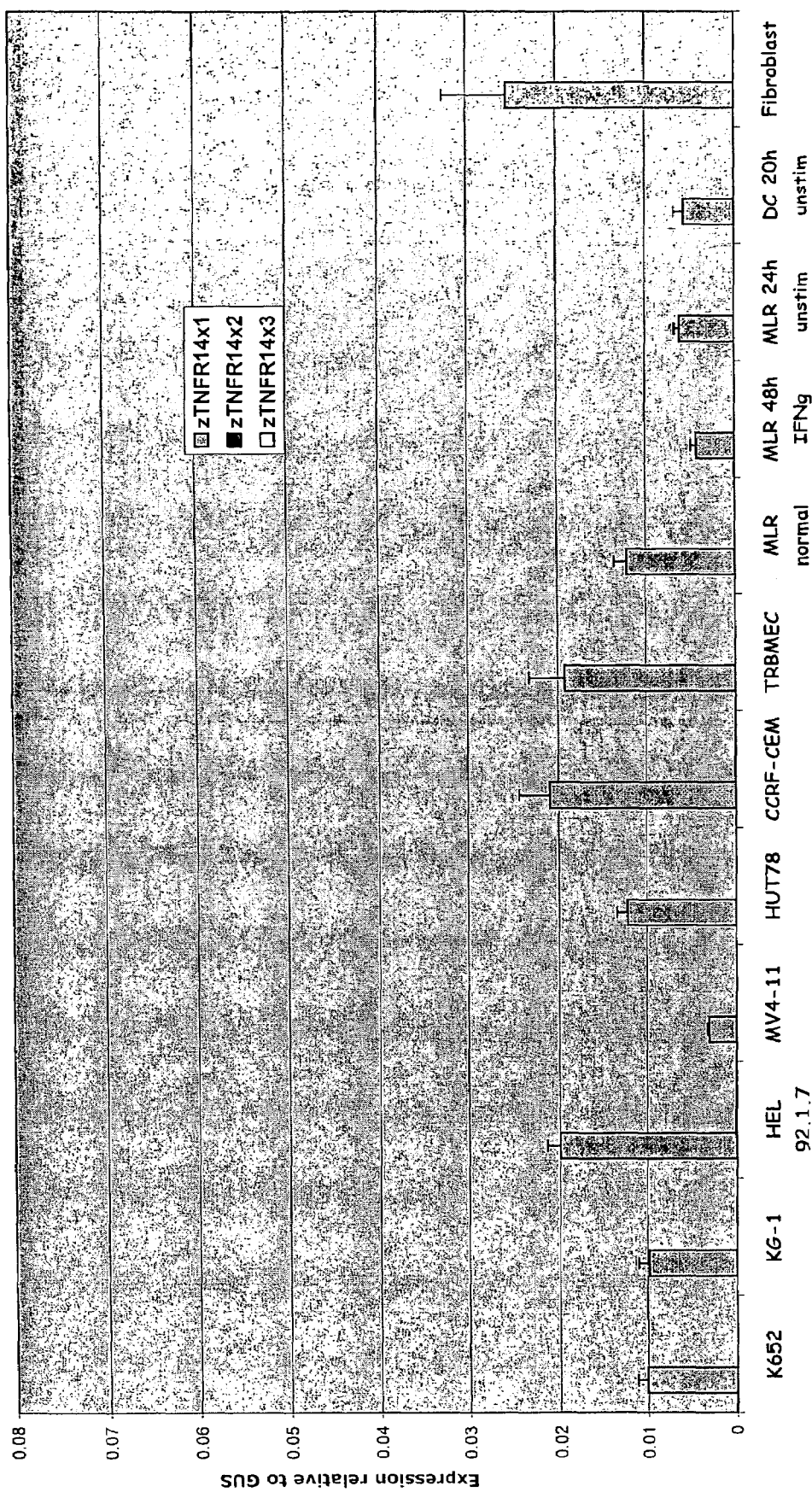
FIG. 5 is a graphic representation of the results of real time PCR analysis to access the expression of ztnrfl4×1, ztnfr14×2, and ztnfr14×3 in various unstimulated monocyte, T cell lines, as well as a transformed bone marrow endothelial cell line (TRBMEC), (MLR) and fibroblast lines.
Figure 6:
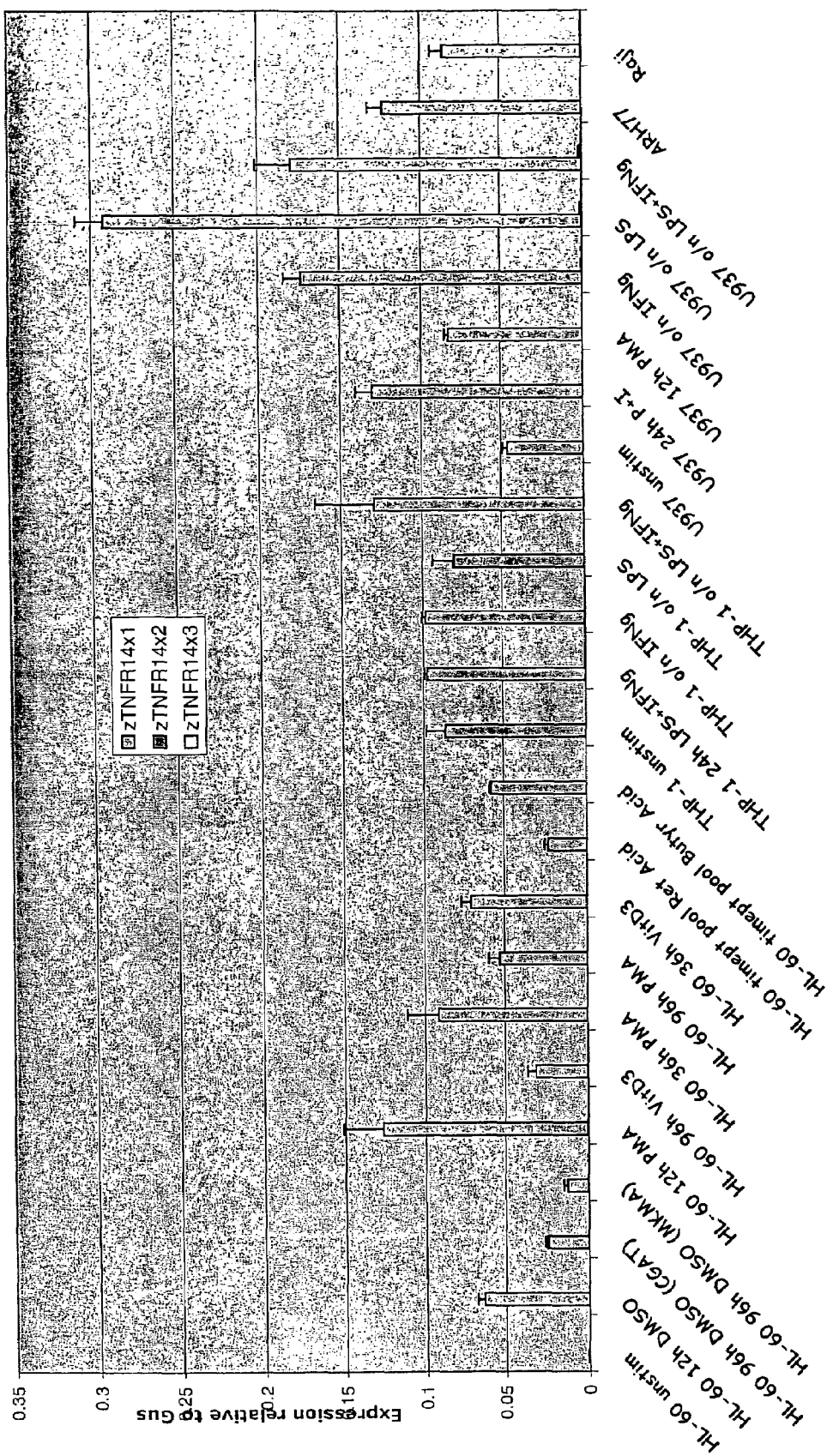
FIG. 6 is a graphic representation of the results of real time PCR analysis to access the expression of ztnrfl4×1, ztnfr14×2, and ztnfr14×3 in various resting and stimulated human monocyte lines.

The results of these experiments are graphically represented in FIGS. 4, 5, and 6. These results indicate that the human zTNFR14×1 appears to be the mRNA splice variant that is predominantly expressed in these cells types. ARH-77, Granta519 and LPS-activated U937 cells appear to have the greatest expression of zTNFR14×1 relative to hGUS and compared to the other lines examined. In general, ztnfr14 appears to increase in expression as cells from monocyte cell lines go from a resting to a stimulated state, allowing for differentiation between resting and stimulated cells. Also, this receptor is transcribed at a significant level in B cell, T cell, monocyte and various other immune cell lines.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide consisting of residues 1 to 108 of SEQ ID NO:2.

2. An isolated polypeptide consisting of residues 1 to 131 of SEQ ID NO:2.

3. An isolated polypeptide consisting of residues 18 to 131 of SEQ ID NO:2.

4. An isolated polypeptide consisting of residues 18 to 198 of SEQ ID NO:2.

5. An isolated polynucleotide that encodes the polypeptide according to claim 1.

6. An isolated polynucleotide that encodes the polypeptide according to claim 2.

7. An isolated polynucleotide that encodes the polypeptide according to claim 3.

8. An isolated polynucleotide that encodes the polypeptide according to claim 4.

9. An expression vector comprising the following operably linked elements:

a) a transcription promoter;
b) a DNA segment wherein the DNA segment is a polynucleotide molecule encoding the polypeptide molecule of claim 1; and
c) a transcription terminator.

10. The expression vector according to claim 9 wherein the DNA segment further contains an affinity tag.

11. A cultured cell into which has been introduced an expression vector according to claim 9, wherein said cell expresses the polypeptide encoded by the DNA segment.

12. A method of producing a polypeptide comprising culturing a cell according to claim 11, whereby said cell expresses the polypeptide encoded by the DNA segment; and recovering the polypeptide.

13. The polypeptide of claim 1 which is a soluble receptor.

* * * * *